US009163231B2

(12) United States Patent
Wilson et al.

(10) Patent No.: US 9,163,231 B2
(45) Date of Patent: Oct. 20, 2015

(54) RANDOM RNAI LIBRARIES, METHODS OF GENERATING SAME, AND SCREENING METHODS UTILIZING SAME

(75) Inventors: Robert B. Wilson, Wynnewood, PA (US); Yongping Wang, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 774 days.

(21) Appl. No.: 12/281,752

(22) PCT Filed: Mar. 6, 2007

(86) PCT No.: PCT/US2007/005682
§ 371 (c)(1),
(2), (4) Date: Jan. 6, 2009

(87) PCT Pub. No.: WO2007/103365
PCT Pub. Date: Sep. 13, 2007

(65) Prior Publication Data
US 2009/0285788 A1    Nov. 19, 2009

(51) Int. Cl.
C12N 15/10    (2006.01)
C12N 15/11    (2006.01)
C12N 15/65    (2006.01)
C12N 15/66    (2006.01)

(52) U.S. Cl.
CPC .......... *C12N 15/1086* (2013.01); *C12N 15/111* (2013.01); *C12N 15/65* (2013.01); *C12N 15/66* (2013.01); *C12N 2310/14* (2013.01); *C12N 2310/53* (2013.01); *C12N 2320/11* (2013.01); *C12N 2330/31* (2013.01)

(58) Field of Classification Search
USPC ............... 435/6.1, 6.11, 6.12, 375, 455, 6.16, 435/91.21, 91.4; 514/44; 536/23.1, 23.2, 536/24.5; 424/93.21
See application file for complete search history.

(56) References Cited

U.S. PATENT DOCUMENTS

| 8,013,143 B2 * | 9/2011 | McSwiggen et al. ........ 536/24.5 |
| 2004/0002056 A1 | 1/2004 | Lorens et al. |
| 2004/0053876 A1 * | 3/2004 | Turner et al. ................... 514/44 |
| 2005/0079160 A1 | 4/2005 | Solomon et al. |
| 2005/0261218 A1 * | 11/2005 | Esau et al. ...................... 514/44 |
| 2006/0035344 A1 * | 2/2006 | Pachuk et al. ................ 435/91.1 |

FOREIGN PATENT DOCUMENTS

| WO | WO 03/020931 | 3/2003 |
| WO | WO 03/070966 | 8/2003 |
| WO | WO03076592 | * 9/2003 |
| WO | WO 2004/009796 | 1/2004 |
| WO | WO 2004/026227 | 4/2004 |
| WO | WO 2004/101788 | 11/2004 |
| WO | WO 2004/108897 | 12/2004 |
| WO | WO 2015/020993 A2 | 2/2015 |

OTHER PUBLICATIONS

Elbashir et al., "Duplexes of 21-.nucleotide RNAs mediate RNA Interference in cultured mammalian cells", Nature 411:494-498 (2001).*
Chen Meihong et al., "A universal plasmid library encoding all permutations of small interfering RNA", Proceedings of the National Academy of SCiences of the United States of America, 2005, vol. 102, No. 7, pp. 2356-2361.
Luo Biao et al., "Small interfering RNA production by enzymatic engineering of DNA (speed)", Proceedings of the National Academy of SCiences of the United States of America, 2004, vol. 101, No. 15, pp. 5494-5499.
Shirane Daisuke et al., "Enzymatic production of RNAi libraries from cDNAs", Nature Genetics 2004, vol. 36, No. 2, pp. 190-196.
Sen George et al., "Restriction enzyme generated siRNA (REGS) vectors and libraries", Nature Genetics, 2004, vol. 36, No. 2, pp. 183-189.
Kaykas Ajamete et al., "A plasmid-based system for expressing small interfering RNA libraries in mammalian cells", BMC Cell Biology, 2004, vol. 5, p. 16.
Auf Der Maur et al., "Direct in-vivo screening of intrabody libraries constructed on a highly stable single-chain framework", Journal of Biological Chemistry, American Society for Biochemistry and Molecular Biology, vol. 277, No. 47, Nov. 2002, pp. 45075-45085.
Kim et al., "Receptor inhibition oh pheromone signaling is mediated by the STE4p GI2 subunit", Molecular and Cellular Biology, vol. 19, No. 1, Jan. 1999, p. 441.
Enright AJ, John B, Gaul U, Tuschl T, Sander C, Marks DS. MicroRNA targets in Drosophila. Genome Biol 2003;5(1):R1.
M. Megraw, P. Sethupathy, B. Corda, and A.G. Hatzigeorgiou (2006). Nucleic Acids Res, 35: D149-D155.
Lewis BP, Burge CB, Bartel DP. "Conserved seed pairing, often flanked by adenosines, indicates that thousands of human genes are microRNA targets" Cell, 120:15-16 (2005).
Lim, LP, Lau, NC, Weinstein, E, Abdelhakim, A, Yekta, S, Rhoades, MW, Burge, CB and Bartel, DP (2003). The microRNAs of Caenorhabditis elegans. Genes & Dev. 17, 991.
Krek et al, Nature Genetics 37:495-500 (2005).
Rusinov V, Baev V, Minkov IN, Tabler M. "MicroInspector: a web tool for detection of miRNA binding sites in an RNA sequence" Nucleic Acids Res 2005;33: W696-700.
Palliser D et al (An sRNA-based microbicide protects mice from lethal herpes simplex virus 2 infection. Nature. Jan. 5, 2006;439(7072):89-94.

(Continued)

*Primary Examiner* — Jane Zara
(74) *Attorney, Agent, or Firm* — Mark S. Cohen; Pearl Cohen; Zedek Latzer Baratz LLP

(57) ABSTRACT

This invention provides expression vectors for a ribonucleic acid (RNA) molecule comprising a double-stranded region of random sequence, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

27 Claims, 14 Drawing Sheets

(56) References Cited

OTHER PUBLICATIONS

Wadhwa R et al (Vectors for RNA interference. Curr Opin Mol Ther. Aug. 2004;6(4):367-72.
Griffiths-Jones S, Grocock RJ, van Dongen S, Bateman A, Enright AJ. Nucl Acids Res, 2006, 34: D140-D144.
Griffiths-Jones S (Nucl Acids Res, 2004, 32: D109-D111.
Jaronczyk K et al (Exploring the functions of RNA interference pathway proteins: some functions are more RISCy than others. Biochem J. May 1, 2005;387(Pt 3):561-71.
Banan M et al (The ins and outs of RNAi in mammalian cells. Curr Pharm Biotechnol. Oct. 2004;5(5):441-50).
Jauslin et al. "A cellular model for Friedreich Ataxia reveals small-molecule glutathione peroxidase mimetics as novel treatment strategy", Hum Molec Gen 11: 3055, 2002.
Chambers et al (Functional expression cloning of Nanog, a pluripotency sustaining factor in embryonic stem (ES) cells. Cell 113, 643-55 (2003).
Nishikawa & Sugiyama, "A shRNA library constructed through the generation of loop-stem-loop DNA J Gene Med 2010", *J Gene Med* 2010, 12: 927-933.
Nichols & Steinman,"A recombinase-based palindrome generator capable of producing randomized shRNA libraries" *J Biotech* 2009 143: 79-84.
Guo et al., "A randomized lentivirus shRNA library construction" Biochemical and Biophysical Research Communications 2007 358: 272-76.
Communication under Rule 71(3) EPC mailed Apr. 2, 2015 for EP Application No. 07752388.4.

\* cited by examiner

Random library sequences:

| Clone | N29 | A/T | C/G |
|---|---|---|---|
| 1-7 | AGCTCGTAACGATCTACACATGTGCTGCG | 14 | 15 |
| 1-8 | GGTCGTTTTACGATTAACAGGTTCCCCGG | 14 | 15 |
| 1-24 | CTCATAAGACGGGCCCGTAACAAAAAACG | 15 | 14 |
| 2-3 | TAAAAGACTCTGGCGCCGGTGAATGATTG | 15 | 14 |
| 2-4 | CTTCGATGACAAGTATCTATTGACGAAAG | 18 | 11 |
| 2-5 | GGGGAAAGGGTGTGGGAACACGACTCACG | 11 | 18 |
| 3-10 | TAGACTGGTATGCGAGGGCAGAGTACGCG | 11 | 18 |
| 3-12 | CACAAACCCCCATGATGCATGATGCGCAG | 13 | 16 |
| 4-1 | CTGAGATCGGCAATGGAGTATAACATCAG | 16 | 13 |
| 4-2 | CTAAGCGGGTGGAATAGGGGATGAGAGGG | 12 | 17 |
| 5-1 | CCCTTATGTAAACGTGATCCTCCAACATG | 16 | 13 |
| 5-3 | GTATAACCATTTCCGGGCTTATGATTAGG | 17 | 12 |
| 5-4 | AATGACCCTTTGCATAAAGATATTCCTAG | 19 | 10 |
| 5-11 | CTCGCCTTATGGAGCTTTTGAACAACAGG | 15 | 14 |
| | avg | 14.7 | 14.3 |

Figure 10

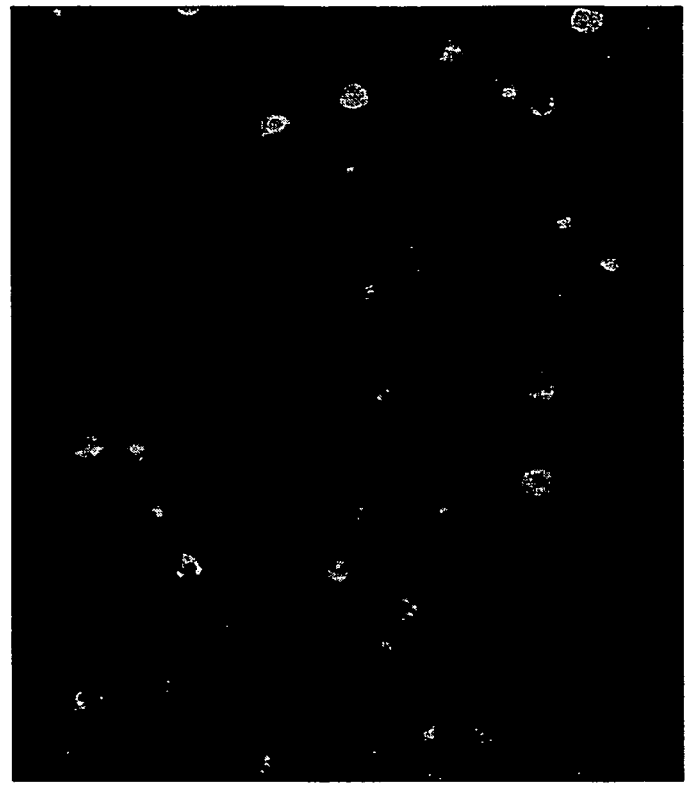
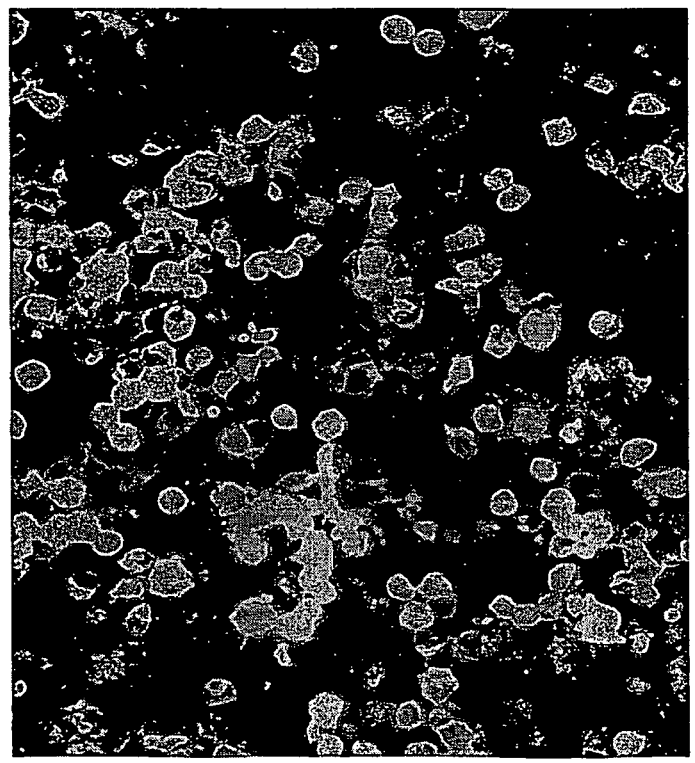
FIGURE 13 ional Filing Date Mar. 6, 2007, claiming priority to U.S.

SEQUENCE LISTING

<160> NUMBER OF SEQ ID NOS: 69

<210> SEQ ID NO 1
<211> LENGTH: 29
<212> TYPE: DNA
<213> ORGANISM: Artificial

```
<220> FEATURE:
<223> OTHER INFORMATION: chemically synthesized

<400> SEQUENCE: 1
gggtagctac atttgcatat gtggatatg                                29

<210> SEQ ID NO 2
<211> LENGTH: 29
<212> TYPE: DNA
<213> ORGANISM: Artificial
<220> FEATURE:
<223> OTHER INFORMATION: chemically synthesized

<400> SEQUENCE: 2
gtggatcagt gtgttatagc tcgggcagg                                29

<210> SEQ ID NO 3
<211> LENGTH: 19
<212> TYPE: DNA
<213> ORGANISM: Artificial
<220> FEATURE:
<223> OTHER INFORMATION: chemically synthesized

<400> SEQUENCE: 3
acctcccgta ggtgatgca                                           19

<210> SEQ ID NO 4
<211> LENGTH: 15
<212> TYPE: DNA
<213> ORGANISM: Artificial
<220> FEATURE:
<223> OTHER INFORMATION: chemically synthesized

<400> SEQUENCE: 4
tcacctgcgg gagct                                               15

<210> SEQ ID NO 5
<211> LENGTH: 20
<212> TYPE: DNA
<213> ORGANISM: Artificial
<220> FEATURE:
<223> OTHER INFORMATION: chemically synthesized

<400> SEQUENCE: 5
acctcccgta ggtgatgcag                                          20

<210> SEQ ID NO 6
<211> LENGTH: 20
<212> TYPE: DNA
<213> ORGANISM: Artificial
<220> FEATURE:
<223> OTHER INFORMATION: chemically synthesized

<400> SEQUENCE: 6
ctgcatcacc tgcgggagct                                          20

<210> SEQ ID NO 7
<211> LENGTH: 20
<212> TYPE: DNA
<213> ORGANISM: Artificial
<220> FEATURE:
<223> OTHER INFORMATION: chemically synthesized

<400> SEQUENCE: 7
ctgcatcacc tacgggaggt                                          20
```

<210> SEQ ID NO 8
<211> LENGTH: 19
<212> TYPE: DNA
<213> ORGANISM: Artificial
<220> FEATURE:
<223> OTHER INFORMATION: chemically synthesized

<400> SEQUENCE: 8
agctcccgca ggtgatgca                                          19

<210> SEQ ID NO 9
<211> LENGTH: 21
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (21)..(21)
<223> OTHER INFORMATION: n is a, c, g, or t

<400> SEQUENCE: 9
ctgcatcacc tgcgggagct n                                       21

<210> SEQ ID NO 10
<211> LENGTH: 20
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (1)..(1)
<223> OTHER INFORMATION: n is a, c, g, or t

<400> SEQUENCE: 10
nagctcccgc aggtgatgca                                         20

<210> SEQ ID NO 11
<211> LENGTH: 10
<212> TYPE: DNA
<213> ORGANISM: Artificial
<220> FEATURE:
<223> OTHER INFORMATION: chemically synthesized

<400> SEQUENCE: 11
acctcccgct                                                    10

<210> SEQ ID NO 12
<211> LENGTH: 10
<212> TYPE: DNA
<213> ORGANISM: Artificial
<220> FEATURE:
<223> OTHER INFORMATION: chemically synthesized

<400> SEQUENCE: 12
agcgggaggt                                                    10

<210> SEQ ID NO 13
<211> LENGTH: 73
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (27)..(54)
<223> OTHER INFORMATION: n is a, c, g, or t

```
<400> SEQUENCE: 13
tctccgtaga gcgatgacct gaaaaannnn nnnnnnnnnn nnnnnnnnnn nnnnggttta      60
aacaggtggt cga                                                       73

<210> SEQ ID NO 14
<211> LENGTH: 15
<212> TYPE: DNA
<213> ORGANISM: Artificial
<220> FEATURE:
<223> OTHER INFORMATION: chemically synthesized

<400> SEQUENCE: 14
ccacctgctt aaagc                                                     15

<210> SEQ ID NO 15
<211> LENGTH: 80
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (27)..(54)
<223> OTHER INFORMATION: n is a, c, g, or t

<400> SEQUENCE: 15
tctccgtaga gcgatgacct gaaaaannnn nnnnnnnnnn nnnnnnnnnn nnnnttttttc     60 aggtcatcgc tctacggaga                                                80

<210> SEQ ID NO 16
<211> LENGTH: 44
<212> TYPE: DNA
<213> ORGANISM: Artificial
<220> FEATURE:
<223> OTHER INFORMATION: chemically synthesized

<400> SEQUENCE: 16
ggaagcatgc cgcagcttca gtcagctgcg gcatgcttcc tcga                     44

<210> SEQ ID NO 17
<211> LENGTH: 186
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (27)..(54)
<223> OTHER INFORMATION: n is a, c, g, or t
<220> FEATURE:
<221> NAME/KEY: misc_feature
<222> LOCATION: (133)..(160)
<223> OTHER INFORMATION: n is a, c, g, or t

<400> SEQUENCE: 17
tctccgtaga gcgatgacct gaaaaannnn nnnnnnnnnn nnnnnnnnnn nnnnggttta      60
aacaggtggt cgaggaagca tgccgcagct tcagtcagct gcggcatgct tcctcgacca    120
cctgcttaaa gcnnnnnnnn nnnnnnnnnn nnnnnnnnnn tttttcaggt catcgctcta    180
cggaga                                                              186

<210> SEQ ID NO 18
<211> LENGTH: 55
<212> TYPE: DNA
<213> ORGANISM: Artificial
```

```
<220> FEATURE:
<223> OTHER INFORMATION: chemically synthesized
<220> FEATURE:
<221> NAME/KEY: misc_feature
<222> LOCATION: (27)..(54)
<223> OTHER INFORMATION: n is a, c, g, or t

<400> SEQUENCE: 18
tctccgtaga gcgatgacct gaaaaannnn nnnnnnnnnn nnnnnnnnnn nnnng            55

<210> SEQ ID NO 19
<211> LENGTH: 55
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 19
cnnnnnnnnn nnnnnnnnnn nnnnnnnnnt ttttcaggtc atcgctctac ggaga            55

<210> SEQ ID NO 20
<211> LENGTH: 18
<212> TYPE: DNA
<213> ORGANISM: Artificial
<220> FEATURE:
<223> OTHER INFORMATION: chemically synthesized

<400> SEQUENCE: 20
ccgtagaccg atgacctg                                                     18

<210> SEQ ID NO 21
<211> LENGTH: 52
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (24)..(51)
<223> OTHER INFORMATION: n is a, c, g, or t

<400> SEQUENCE: 21
ccgtagaccg atgacctgaa aaannnnnnn nnnnnnnnnn nnnnnnnnnn ng               52

<210> SEQ ID NO 22
<211> LENGTH: 55
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 22
cnnnnnnnnn nnnnnnnnnn nnnnnnnnnt ttttcaggtc atcgcactac ggaga            55

<210> SEQ ID NO 23
<211> LENGTH: 52
<212> TYPE: DNA
<213> ORGANISM: Artificial
<220> FEATURE:
<223> OTHER INFORMATION: chemically synthesized
```

```
<220> FEATURE:
<221> NAME/KEY: misc_feature
<222> LOCATION: (24)..(51)
<223> OTHER INFORMATION: n is a, c, g, or t

<400> SEQUENCE: 23
ccgtagaccg atgacctgaa aaannnnnnn nnnnnnnnnn nnnnnnnnnn ng          52

<210> SEQ ID NO 24
<211> LENGTH: 37
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (9)..(36)
<223> OTHER INFORMATION: n is a, c, g, or t

<400> SEQUENCE: 24
ccagctttnn nnnnnnnnn nnnnnnnnnn nnnnnng                            37

<210> SEQ ID NO 25
<211> LENGTH: 60
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 25
cnnnnnnnnn nnnnnnnnnn nnnnnnnnnt ttttcaggtc atcgctctac ggagatggcc  60

<210> SEQ ID NO 26
<211> LENGTH: 60
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (32)..(59)
<223> OTHER INFORMATION: n is a, c, g, or t

<400> SEQUENCE: 26
ggccatctcc gtagaccgat gacctgaaaa annnnnnnnn nnnnnnnnnn nnnnnnnnng  60

<210> SEQ ID NO 27
<211> LENGTH: 37
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 27
cnnnnnnnnn nnnnnnnnnn nnnnnnnnna aagctgg                           37

<210> SEQ ID NO 28
<211> LENGTH: 134
<212> TYPE: DNA
<213> ORGANISM: Artificial
```

```
<220> FEATURE:
<223> OTHER INFORMATION: chemically synthesized
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (107)..(134)
<223> OTHER INFORMATION: n is a, c, g, or t

<400> SEQUENCE: 28
nnnnnnnnnn nnnnnnnnnn nnnnnnnngg tttaaacagg tggtcgagga agcatgccgc      60
agcttcagtc agctgcggca tgcttcctcg accacctgct taaagcnnnn nnnnnnnnnn     120
nnnnnnnnnn nnnn                                                      134

<210> SEQ ID NO 29
<211> LENGTH: 134
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (107)..(134)
<223> OTHER INFORMATION: n is a, c, g, or t

<400> SEQUENCE: 29
nnnnnnnnnn nnnnnnnnnn nnnnnnnngc tttaagcagg aggacgagga agcatgccgc      60
agctgactga agctgcggca tgcttcctcg accacctgtt taaaccnnnn nnnnnnnnnn     120
nnnnnnnnnn nnnn                                                      134

<210> SEQ ID NO 30
<211> LENGTH: 33
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (1)..(28)
<223> OTHER INFORMATION: n is a, c, g, or t

<400> SEQUENCE: 30
nnnnnnnnnn nnnnnnnnnn nnnnnnnngg ttt                                   33

<210> SEQ ID NO 31
<211> LENGTH: 33
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (6)..(33)
<223> OTHER INFORMATION: n is a, c, g, or t

<400> SEQUENCE: 31
aaaccnnnnn nnnnnnnnnn nnnnnnnnnn nnn                                   33
```

```
<210> SEQ ID NO 32
<211> LENGTH: 103
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (9)..(36)
<223> OTHER INFORMATION: n is a, c, g, or t
<220> FEATURE:
<221> NAME/KEY: misc_feature
<222> LOCATION: (45)..(72)
<223> OTHER INFORMATION: n is a, c, g, or t

<400> SEQUENCE: 32
ccagctttnn nnnnnnnnnn nnnnnnnnnn nnnnnnggtt tagcnnnnnn nnnnnnnnnn    60
nnnnnnnnnn nnttttttcag gtcatctcac tacggagatg gcc                    103

<210> SEQ ID NO 33
<211> LENGTH: 103
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (32)..(59)
<223> OTHER INFORMATION: n is a, c, g, or t
<220> FEATURE:
<221> NAME/KEY: misc_feature
<222> LOCATION: (68)..(95)
<223> OTHER INFORMATION: n is a, c, g, or t

<400> SEQUENCE: 33
ggccatctcc gtagtgagat gacctgaaaa annnnnnnnn nnnnnnnnnn nnnnnnnnng    60
ctaaaccnnn nnnnnnnnnn nnnnnnnnnn nnnnnaaagc tgg                     103

<210> SEQ ID NO 34
<211> LENGTH: 96
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (47)..(51)
<223> OTHER INFORMATION: phosphorothioate
<220> FEATURE:
<221> NAME/KEY: misc_feature
<222> LOCATION: (52)..(77)
<223> OTHER INFORMATION: n is a, c, g, or t

<400> SEQUENCE: 34
cccttatgca tgctgaggaa gaattcagcg gccgcgatga cctgaaaaan nnnnnnnnn     60 nnnnnnnnnn nnnnnnggt ttaaacaggt ggtcga                              96

<210> SEQ ID NO 35
<211> LENGTH: 92
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (16)..(43)
<223> OTHER INFORMATION: n is a, c, g, or t
```

```
<400> SEQUENCE: 35
ccacctgctt aaagcnnnnn nnnnnnnnnn nnnnnnnnnn nnnttttttca ggtcatcgcg      60 gccgctgaat tcttcctcag catgcataag gg                                     92

<210> SEQ ID NO 36
<211> LENGTH: 44
<212> TYPE: DNA
<213> ORGANISM: Artificial
<220> FEATURE:
<223> OTHER INFORMATION: chemically synthesized

<400> SEQUENCE: 36
ggaagcatga attctattca gtcatagaat tcatgcttcc tcga                        44

<210> SEQ ID NO 37
<211> LENGTH: 232
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (47)..(51)
<223> OTHER INFORMATION: phosphorothioate
<220> FEATURE:
<221> NAME/KEY: misc_feature
<222> LOCATION: (52)..(77)
<223> OTHER INFORMATION: n is a, c, g, or t
<220> FEATURE:
<221> NAME/KEY: misc_feature
<222> LOCATION: (156)..(183)
<223> OTHER INFORMATION: n is a, c, g, or t

<400> SEQUENCE: 37
cccttatgca tgctgaggaa gaattcagcg gccgcgatga cctgaaaaan nnnnnnnnn        60 nnnnnnnnnn nnnnnnnggt ttaaacaggt ggtcgaggaa gcatgaattc tattcagtca      120
tagaattcat gcttcctcga ccacctgctt aaagcnnnnn nnnnnnnnnn nnnnnnnnnn      180 nnnttttttca ggtcatcgcg gccgctgaat tcttcctcag catgcataag gg             232

<210> SEQ ID NO 38
<211> LENGTH: 45
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (17)..(44)
<223> OTHER INFORMATION: n is a, c, g, or t

<400> SEQUENCE: 38
gcgatgacct gaaaaannnn nnnnnnnnnn nnnnnnnnnn nnnng                       45

<210> SEQ ID NO 39
<211> LENGTH: 65
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t
```

```
<400> SEQUENCE: 39
cnnnnnnnnn nnnnnnnnnn nnnnnnnnnt ttttcaggtc atcgcggccg ctgaattctt    60
cctca                                                                65

<210> SEQ ID NO 40
<211> LENGTH: 65
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (34)..(48)
<223> OTHER INFORMATION: phosphorothioate
<220> FEATURE:
<221> NAME/KEY: misc_feature
<222> LOCATION: (49)..(64)
<223> OTHER INFORMATION: n is a, c, g, or t

<400> SEQUENCE: 40
tgaggaagaa ttcagcggcc gcgatgacct gaaaaannnn nnnnnnnnnn nnnnnnnnnn    60 nnnng                                                                65

<210> SEQ ID NO 41
<211> LENGTH: 45
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 41
cnnnnnnnnn nnnnnnnnnn nnnnnnnnnt ttttcaggtc atcgc                    45

<210> SEQ ID NO 42
<211> LENGTH: 65
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 42
cnnnnnnnnn nnnnnnnnnn nnnnnnnnnt ttttcaggtc atcgcggccg ctgaattctt    60
cctca                                                                65

<210> SEQ ID NO 43
<211> LENGTH: 65
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (37)..(64)
<223> OTHER INFORMATION: n is a, c, g, or t

<400> SEQUENCE: 43
tgaggaagaa ttcagcggcc gcgatgacct gaaaaannnn nnnnnnnnnn nnnnnnnnnn    60 nnnng                                                                65
```

```
<210> SEQ ID NO 44
<211> LENGTH: 45
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 44
cnnnnnnnnn nnnnnnnnnn nnnnnnnnnt ttttcaggtc atcgc                45

<210> SEQ ID NO 45
<211> LENGTH: 49
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (21)..(48)
<223> OTHER INFORMATION: n is a, c, g, or t

<400> SEQUENCE: 45
ggccgcgatg acctgaaaaa nnnnnnnnnn nnnnnnnnnn nnnnnnng            49

<210> SEQ ID NO 46
<211> LENGTH: 19
<212> TYPE: DNA
<213> ORGANISM: Artificial
<220> FEATURE:
<223> OTHER INFORMATION: chemically synthesized

<400> SEQUENCE: 46
accacagatc tccggccgc                                             19

<210> SEQ ID NO 47
<211> LENGTH: 15
<212> TYPE: DNA
<213> ORGANISM: Artificial
<220> FEATURE:
<223> OTHER INFORMATION: chemically synthesized

<400> SEQUENCE: 47
gcggagatct gtggt                                                 15

<210> SEQ ID NO 48
<211> LENGTH: 42
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (14)..(41)
<223> OTHER INFORMATION: n is a, c, g, or t

<400> SEQUENCE: 48
accacagatc tccnnnnnnn nnnnnnnnnn nnnnnnnnnn ng                   42

<210> SEQ ID NO 49
<211> LENGTH: 45
<212> TYPE: DNA
<213> ORGANISM: Artificial
<220> FEATURE:
<223> OTHER INFORMATION: chemically synthesized
```

<220> FEATURE:
<221> NAME/KEY: misc_feature
<222> LOCATION: (2)..(29)
<223> OTHER INFORMATION: n is a, c, g, or t

<400> SEQUENCE: 49
cnnnnnnnnn nnnnnnnnnn nnnnnnnnnt ttttcaggtc atcgc                45

<210> SEQ ID NO 50
<211> LENGTH: 51
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (23)..(50)
<223> OTHER INFORMATION: n is a, c, g, or t

<400> SEQUENCE: 50
gcggccgcga tgacctgaaa aannnnnnnn nnnnnnnnnn nnnnnnnnnn g          51

<210> SEQ ID NO 51
<211> LENGTH: 42
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (2)..(29)
<223> OTHER INFORMATION: n is a, c, g, or t

<400> SEQUENCE: 51
cnnnnnnnnn nnnnnnnnnn nnnnnnnnng gagatctgtg gt                    42

<210> SEQ ID NO 52
<211> LENGTH: 99
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (14)..(41)
<223> OTHER INFORMATION: n is a, c, g, or t
<220> FEATURE:
<221> NAME/KEY: misc_feature
<222> LOCATION: (50)..(77)
<223> OTHER INFORMATION: n is a, c, g, or t

<400> SEQUENCE: 52
accacagatc tccnnnnnnn nnnnnnnnnn nnnnnnnnn ngcttaaccn nnnnnnnnn    60 nnnnnnnnnn nnnnnnnttt ttcaggtcat cgcggccgc                        99

<210> SEQ ID NO 53
<211> LENGTH: 99
<212> TYPE: DNA
<213> ORGANISM: Artificial
<220> FEATURE:
<223> OTHER INFORMATION: chemically synthesized
<220> FEATURE:
<221> NAME/KEY: misc_feature
<222> LOCATION: (23)..(50)
<223> OTHER INFORMATION: n is a, c, g, or t
<220> FEATURE:
<221> NAME/KEY: misc_feature
<222> LOCATION: (59)..(86)
<223> OTHER INFORMATION: n is a, c, g, or t -continued

<400> SEQUENCE: 53
gcggccgcga tgacctgaaa aannnnnnnn nnnnnnnnnn nnnnnnnnnn ggttaagcnn    60
nnnnnnnnnn nnnnnnnnnn nnnnnnggag atctgtggt                           99

<210> SEQ ID NO 54
<211> LENGTH: 144
<212> TYPE: DNA
<213> ORGANISM: Artificial
<220> FEATURE:
<223> OTHER INFORMATION: Library intermediate consensus
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (33)..(60)
<223> OTHER INFORMATION: n is a, c, g, or t
<220> FEATURE:
<221> NAME/KEY: misc_feature
<222> LOCATION: (111)..(138)
<223> OTHER INFORMATION: n is a, c, g, or t

<400> SEQUENCE: 54
cttataagtt ctgtatgaga ccacagatct ccnnnnnnnn nnnnnnnnnn nnnnnnnnnn    60
gctttaagca ggtgtatcca gcacagtggc ggccgcgatg acctgaaaaa nnnnnnnnnn   120
nnnnnnnnnn nnnnnnnngg ttta                                         144

<210> SEQ ID NO 55
<211> LENGTH: 29
<212> TYPE: DNA
<213> ORGANISM: Artificial
<220> FEATURE:
<223> OTHER INFORMATION: Random region sequences

<400> SEQUENCE: 55
agctcgtaac gatctacaca tgtgctgcg                                     29

<210> SEQ ID NO 56
<211> LENGTH: 29
<212> TYPE: DNA
<213> ORGANISM: Artificial
<220> FEATURE:
<223> OTHER INFORMATION: Random region sequences

<400> SEQUENCE: 56
ggtcgtttta cgattaacag gttccccgg                                     29

<210> SEQ ID NO 57
<211> LENGTH: 29
<212> TYPE: DNA
<213> ORGANISM: Artificial
<220> FEATURE:
<223> OTHER INFORMATION: Random region sequences

<400> SEQUENCE: 57
ctcataagac gggcccgtaa caaaaaacg                                     29

<210> SEQ ID NO 58
<211> LENGTH: 29
<212> TYPE: DNA
<213> ORGANISM: Artificial
<220> FEATURE:
<223> OTHER INFORMATION: Random region sequences

<400> SEQUENCE: 58
taaaagactc tggcgccggt gaatgattg					29

<210> SEQ ID NO 59
<211> LENGTH: 29
<212> TYPE: DNA
<213> ORGANISM: Artificial
<220> FEATURE:
<223> OTHER INFORMATION: Random region sequences

<400> SEQUENCE: 59
cttcgatgac aagtatctat tgacgaaag					29

<210> SEQ ID NO 60
<211> LENGTH: 29
<212> TYPE: DNA
<213> ORGANISM: Artificial
<220> FEATURE:
<223> OTHER INFORMATION: Random region sequences

<400> SEQUENCE: 60
ggggaaaggg tgtgggaaca cgactcacg					29

<210> SEQ ID NO 61
<211> LENGTH: 29
<212> TYPE: DNA
<213> ORGANISM: Artificial
<220> FEATURE:
<223> OTHER INFORMATION: Random region sequences

<400> SEQUENCE: 61
tagactggta tgcgagggca gagtacgcg					29

<210> SEQ ID NO 62
<211> LENGTH: 29
<212> TYPE: DNA
<213> ORGANISM: Artificial
<220> FEATURE:
<223> OTHER INFORMATION: Random region sequences

<400> SEQUENCE: 62
cacaaacccc catgatgcat gatgcgcag					29

<210> SEQ ID NO 63
<211> LENGTH: 29
<212> TYPE: DNA
<213> ORGANISM: Artificial
<220> FEATURE:
<223> OTHER INFORMATION: Random region sequences

<400> SEQUENCE: 63
ctgagatcgg caatggagta taacatcag					29

<210> SEQ ID NO 64
<211> LENGTH: 29
<212> TYPE: DNA
<213> ORGANISM: Artificial
<220> FEATURE:
<223> OTHER INFORMATION: Random region sequences

<400> SEQUENCE: 64
ctaagcgggt ggaatagggg atgagaggg					29

```
<210> SEQ ID NO 65
<211> LENGTH: 29
<212> TYPE: DNA
<213> ORGANISM: Artificial
<220> FEATURE:
<223> OTHER INFORMATION: Random region sequences

<400> SEQUENCE: 65
cccttatgta aacgtgatcc tccaacatg                                           29

<210> SEQ ID NO 66
<211> LENGTH: 29
<212> TYPE: DNA
<213> ORGANISM: Artificial
<220> FEATURE:
<223> OTHER INFORMATION: Random region sequences

<400> SEQUENCE: 66
gtataaccat ttccgggctt atgattagg                                           29

<210> SEQ ID NO 67
<211> LENGTH: 29
<212> TYPE: DNA
<213> ORGANISM: Artificial
<220> FEATURE:
<223> OTHER INFORMATION: Random region sequences

<400> SEQUENCE: 67
aatgaccctt tgcataaaga tattcctag                                           29

<210> SEQ ID NO 68
<211> LENGTH: 29
<212> TYPE: DNA
<213> ORGANISM: Artificial
<220> FEATURE:
<223> OTHER INFORMATION: Random region sequences

<400> SEQUENCE: 68
ctcgccttat ggagcttttg aacaacagg                                           29

<210> SEQ ID NO 69
<211> LENGTH: 324
<212> TYPE: DNA
<213> ORGANISM: Artificial
<220> FEATURE:
<223> OTHER INFORMATION: Library consensus

<400> SEQUENCE: 69
taagcctttg taacctaagc ctccgcctcc tcttcctcca tccgcccgt ctctccccct          60 tgaacctcct cgttcgaccc cgcctcgatc ctccctttat ccagccctca ctccttctct        120
aggcgccgga attagatcga tctctcgagg tcgacggtat cgataagctt ggtaccgagc        180
tcggatccac tagtccagtg tggtggaatt ctgcagatat ccagcacagt ggcggccgcg        240
atcacctgaa aaaagctcgt aacgatctac acatgtgctg cggtttagcg cagcacatgt        300
gtagatcgtt acgagctgga gatc                                               324
```

RANDOM RNAI LIBRARIES, METHODS OF GENERATING SAME, AND SCREENING METHODS UTILIZING SAME

CROSS-REFERENCE TO RELATED APPLICATIONS

This application is a National Phase Application of PCT International Application No. PCT/US07/05682, International Filing Date Mar. 6, 2007, claiming priority to U.S. Provisional Patent Application 60/779,409, filed Mar. 7, 2006, both of which are incorporated by reference herein in their entirety.

FIELD OF INVENTION

This invention provides expression vectors for a ribonucleic acid (RNA) molecule comprising a double-stranded region of random sequence, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

BACKGROUND OF THE INVENTION

There exists a long-standing need in the art for methods of constructing a random, inhibitory hairpin RNA library. Such a library has important applications in identifying therapeutic RNA molecules and RNA molecules with biological activity, but has been extremely difficult to synthesize because of the limitations of conventional procedures for randomization and generation of RNA libraries. Because of these limitations, libraries containing random ds RNA sequences are fully palindromic, and therefore unsuitable for use in RNAi applications.

SUMMARY OF THE INVENTION

This invention provides expression vectors for a ribonucleic acid (RNA) molecule comprising a double-stranded region of random sequence, sets and libraries of same, methods of generating same, and methods for identifying an RNA therapeutic or RNA molecule that has an ability to affect a biological parameter, for identifying a drug target for a disease or disorder of interest, and for identifying a variant of an RNA molecule that has an altered ability to affect a biological parameter of interest.

In one embodiment, the present invention provides a set or library of recombinant expression vectors, wherein the set or library of recombinant expression vectors expresses a set or library of ribonucleic acid (RNA) molecules. Individual RNA molecules of the set or library of RNA molecules comprise (a) a first region of substantially random sequence; (b) a second, non self-complementary region; and (c) a third region substantially complementary to the first region. In another embodiment, the individual RNA molecules have partial double-stranded secondary structure. In another embodiment, the second, non self-complementary region is situated between the 2 strands of the double-stranded region of random sequence. In another embodiment, the double-stranded region (also referred to herein as "ds region") differs among the set or library of recombinant expression vectors. In another embodiment, the non self-complementary region is common to the set or library of recombinant expression vectors. Each possibility represents a separate embodiment of the present invention.

In another embodiment, the present invention provides a method of generating a set or library of recombinant expression vectors, wherein the set or library of recombinant expression vectors expresses a set or library of ribonucleic acid (RNA) molecules, the method comprising the steps of:
a. obtaining a nucleic acid intermediate II from a single-stranded nucleic acid intermediate I, wherein the single-stranded nucleic acid intermediate I comprises: (i) a first constant region; (ii) a region of random sequence; and (iii) a second constant region;
and wherein the nucleic acid intermediate II, comprises: (i) the single-stranded nucleic acid intermediate I; (ii) an intervening region; and (iii) a region that hybridizes with the single-stranded nucleic acid intermediate I;
b. obtaining a double-stranded intermediate III from the nucleic acid intermediate II, comprising the nucleic acid intermediate II and a nucleic acid molecule that hybridizes with the nucleic acid intermediate II, and wherein the double-stranded intermediate III comprises: (i) a first, double-stranded copy of the first constant region or a fragment thereof; (ii) a first, double-stranded copy of the region of random sequence; (iii) a first, double-stranded copy of the second constant region; (iv) a double-stranded copy of the intervening region; (v) a second, inverted double-stranded copy of the second constant region; (vi) a second, inverted double-stranded copy of the region of random sequence; and (vii) a second, inverted double-stranded copy of the first constant region or a fragment thereof;
wherein the first, double-stranded copy of the second constant region and the second, inverted double-stranded copy of the second constant region have a restriction enzyme site asymmetry, such that:
(i) the first, double-stranded copy of the second constant region, but not the second, inverted double-stranded copy of the second constant region, is a substrate for a first restriction enzyme, and;
(ii) the second, inverted, double-stranded copy of the second constant region, but not the first double-stranded copy of the second constant region, is a substrate for a second restriction enzyme;
thereby generating a set or library of recombinant expression vectors that expresses a set or library of RNA molecules. In another embodiment, the 3 components listed above of the single-stranded nucleic acid intermediate I are ordered in the single-stranded nucleic acid intermediate I in 5' to 3' order as listed. In another embodiment, the 3 components listed above of the nucleic acid intermediate II are ordered in the nucleic acid intermediate II in 5' to 3' order as listed. In another embodiment, the 7 components listed above of the double-stranded intermediate III are ordered in the double-stranded intermediate III in 5' to 3' order as listed. Each possibility represents a separate embodiment of the present invention.

In another embodiment, the present invention provides a method of generating a set or library of recombinant expression vectors, wherein the set or library of recombinant expression vectors is capable of expressing a set or library of RNA molecules, the method comprising the steps of:
(a) synthesizing a nucleotide intermediate I, comprising:
(i) a variable region 6-30 nucleotides in length, wherein either: (1) the sequence of the variable region is substantially random; or (2) the variable region comprises a first sub-region of substantially random sequence and a second sub-region common to the set or library of recombinant expression vectors;

(ii) a constant, non-palindromic region 3-20 nucleotides in length; and (iii) a complementary region, wherein the complementary region is capable of hybridizing with the variable region;

(b) synthesizing a second nucleotide molecule capable of hybridizing with the nucleotide intermediate I; and (c) annealing the nucleotide intermediate I with the second nucleotide molecule, thereby generating a double-stranded product, the double-stranded product comprising double-stranded copies of the variable region, the constant, non-palindromic region, and the complementary region.

thereby generating a set or library of recombinant expression vectors, wherein the set or library of recombinant expression vectors is capable of expressing a set or library of RNA molecules.

In another embodiment, the present invention provides a set or library of recombinant viruses, wherein the recombinant viruses generate RNA molecules comprising a region of random sequence with double-stranded secondary structure, and wherein the set or library of recombinant viruses is generated by a method of the present invention.

In another embodiment, the present invention provides an expression vector for an RNA molecule comprising a double-stranded region of random sequence, wherein the RNA molecule has an ability to affect a biological parameter of interest, and wherein the expression vector is identified by a method of the present invention.

In another embodiment, the present invention provides a method of conferring upon a cell a protection against a viral infection, comprising contacting the cell with an expression vector or RNA molecule of the present invention.

In another embodiment, the present invention provides a method of inhibiting or impeding an ability of a virus to replicate in a subject, comprising contacting the subject with an expression vector of the present invention.

In another embodiment, the present invention provides a method of inducing a differentiation of a cell into a cell type of interest, comprising contacting the cell with an expression vector or RNA molecule of the present invention.

In another embodiment, the present invention provides a method of inducing a long-term proliferation or sustaining a pluripotency of a cell, comprising contacting the cell with an expression vector or RNA molecule of the present invention.

In another embodiment, the present invention provides a set or library of expression vectors, wherein the expression vectors generate RNA molecules comprising a double-stranded region of random sequence, and wherein the set or library of expression vectors is generated by a method of the present invention.

In another embodiment, the present invention provides an expression vector for an RNA molecule comprising a double-stranded region of random sequence, wherein the expression vector is identified by a method of the present invention.

In another embodiment, the present invention provides an RNA molecule that is encoded by an expression vector of the present invention.

In another embodiment, the present invention provides an RNA molecule comprising a double-stranded region of random sequence, wherein the RNA molecule is identified by a method of the present invention.

BRIEF DESCRIPTION OF THE FIGURES

FIG. 10. Sequences of the random (n29) regions of 14 clones from the completed library (SEQ ID NOs: 55-68). Lack of skewing of sequences demonstrated that the method was executed properly and the final product corresponded exactly to the desired product.

FIG. 13. Testing of pQe2, using an anti-GFP shRNA. Left panel: Transfection of 293T cells with pQe2 alone. Right panel: Transfection of 293T cells with pQe2 containing an shRNA construct directed against GFP. Transfection efficiency was confirmed by low-level GFP expression in the cells.

DETAILED DESCRIPTION OF THE INVENTION

Figure 1:
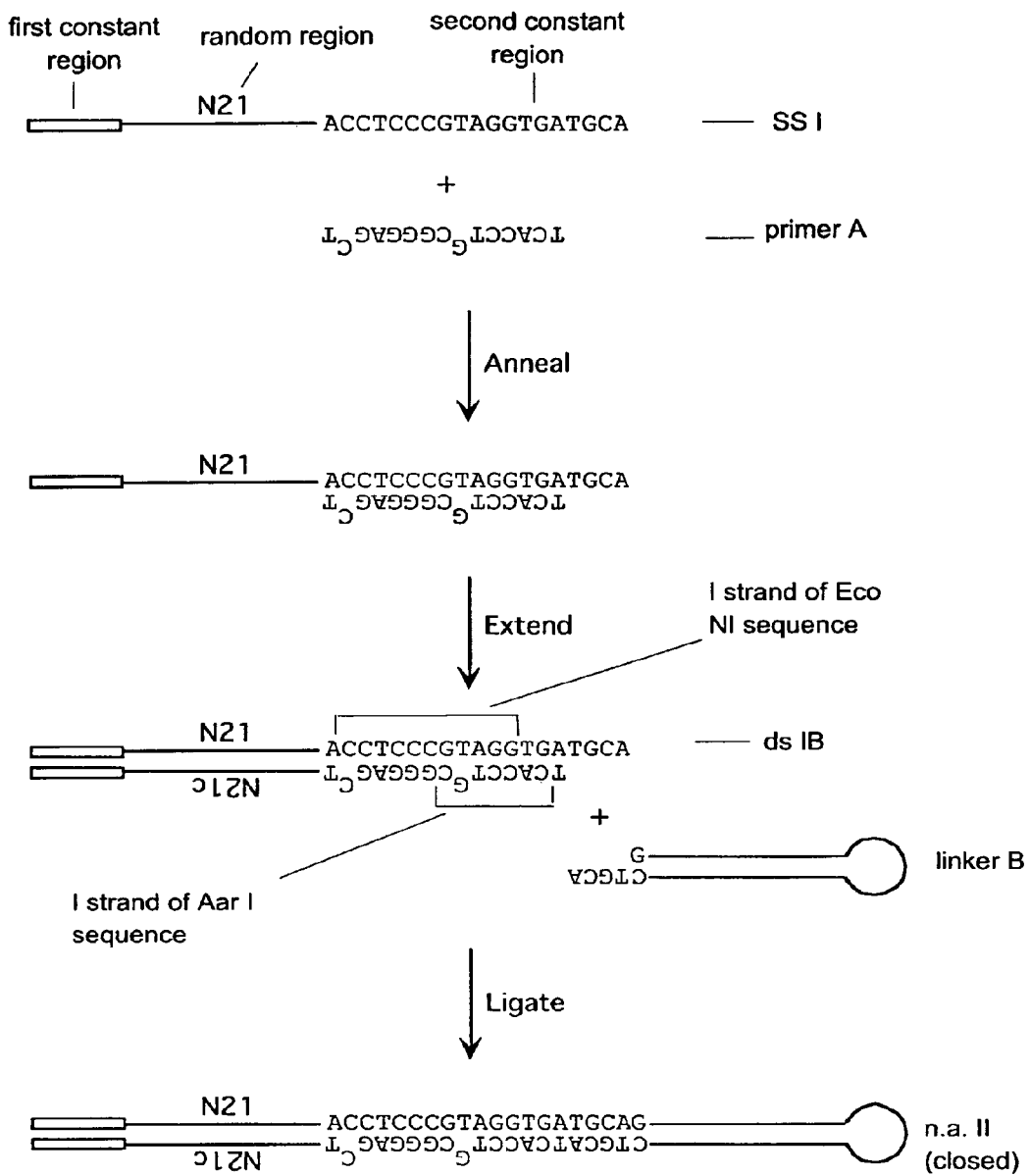
FIG. 1: strategy for creation of a library of expression vectors for partially self-complementary RNA molecules, part I. Described in Example 3. Sequences of 10 or more nt are listed as SEQ ID No: 3-6.

This invention provides expression vectors for a ribonucleic acid (RNA) molecule comprising a double-stranded variable region, sets and libraries of same, methods of generating same, and methods for identifying: an RNA therapeutics or RNA molecules that have an ability to affect a biological parameter; drug targets for a disease or disorder of interest; and variants of an RNA molecule that have an altered ability to affect a biological parameter of interest.

In one embodiment, as exemplified herein in Example 5, the present invention provides a set or library of recombinant expression vectors that expresses a set or library of ribonucleic acid (RNA) molecules. Individual RNA molecules from the set or library each comprise: (a) a first, variable region; (b) a second, non self-complementary region; and (c) third region substantially complementary to the first region. In another embodiment, the second, non self-complementary region is situated between the 2 strands of the double-stranded variable region. In another embodiment, the double-stranded region differs among the set or library of recombinant expression vectors. In another embodiment, the non self-complementary region is common to the set or library of recombinant expression vectors. In another embodiment, individual recombinant expression vectors of the set or library each expresses one type of RNA molecule. In another embodiment, each RNA molecule of set or library comprises the three regions enumerated above. Each possibility represents a separate embodiment of the present invention.

In another embodiment, the sequences of the random or variable regions in the recombinant RNA molecules are generated by adding a mixture of nucleotides to an oligonucleotide synthesizer (Examples 3-5). In another embodiment, the sequences are computer-generated (Example 19). Each possibility represents a separate embodiment of the present invention.

In another embodiment, the variable region of the RNA molecules exhibits substantially random sequence throughout its length. In another embodiment, the variable region comprises a first sub-region of substantially random sequence and a second sub-region common to said set or library of recombinant expression vectors. Each possibility represents a separate embodiment of the present invention.

In another embodiment, the length of the sub-region of substantially random sequence is 27 nt. In another embodiment, the length is 19 nt. In another embodiment, the length is 6 nt. In another embodiment, the length is 7 nt. In another embodiment, the length is 8 nt. In another embodiment, the length is 9 nt. In another embodiment, the length is 10 nt. In another embodiment, the length is 11 nt. In another embodiment, the length is 12 nt. In another embodiment, the length is 13 nt. In another embodiment, the length is 14 nt. In another embodiment, the length is 15 nt. In another embodiment, the length is 16 nt. In another embodiment, the length is 17 nt. In another embodiment, the length is 18 nt. In another embodiment, the length is 20 nt. In another embodiment, the length is 21 nt. In another embodiment, the length is 22 nt. In another embodiment, the length is 23 nt. In another embodiment, the length is 24 nt. In another embodiment, the length is 25 nt. In another embodiment, the length is 26 nt. In another embodiment, the length is 28 nt. In another embodiment, the length is 29 nt. Each possibility represents a separate embodiment of the present invention.

In another embodiment, the length of this sub-region is 6-29 nucleotides. In another embodiment, the length is 7-29 nucleotides. In another embodiment, the length is 8-29 nucleotides. In another embodiment, the length is 9-29 nucleotides. In another embodiment, the length is 10-29 nucleotides. In another embodiment, the length is 11-29 nucleotides. In another embodiment, the length is 12-29 nucleotides. In another embodiment, the length is 13-29 nucleotides. In another embodiment, the length is 14-29 nucleotides. In another embodiment, the length is 15-29 nucleotides. In another embodiment, the length is 7-25 nucleotides. In another embodiment, the length is 8-25 nucleotides. In another embodiment, the length is 9-25 nucleotides. In another embodiment, the length is 10-25 nucleotides. In another embodiment, the length is 11-25 nucleotides. In another embodiment, the length is 12-25 nucleotides. In another embodiment, the length is 13-25 nucleotides. In another embodiment, the length is 14-25 nucleotides. In another embodiment, the length is 15-25 nucleotides. In another embodiment, the length is 7-21 nucleotides. In another embodiment, the length is 8-21 nucleotides. In another embodiment, the length is 9-21 nucleotides. In another embodiment, the length is 10-21 nucleotides. In another embodiment, the length is 11-21 nucleotides. In another embodiment, the length is 12-21 nucleotides. In another embodiment, the length is 13-21 nucleotides. In another embodiment, the length is 14-21 nucleotides. In another embodiment, the length is 15-21 nucleotides. In another embodiment, the length is 7-19 nucleotides. In another embodiment, the length is 8-19 nucleotides. In another embodiment, the length is 9-19 nucleotides. In another embodiment, the length is 10-19 nucleotides. In another embodiment, the length is 11-19 nucleotides. In another embodiment, the length is 12-19 nucleotides. In another embodiment, the length is 13-19 nucleotides. In another embodiment, the length is 14-19 nucleotides. In another embodiment, the length is 15-19 nucleotides. In another embodiment, the length is 7-17 nucleotides. In another embodiment, the length is 8-17 nucleotides. In another embodiment, the length is 9-17 nucleotides. In another embodiment, the length is 10-17 nucleotides. In another embodiment, the length is 11-17 nucleotides. In another embodiment, the length is 12-17 nucleotides. In another embodiment, the length is 13-17 nucleotides. In another embodiment, the length is 14-17 nucleotides. In another embodiment, the length is 7-15 nucleotides. In another embodiment, the length is 8-15 nucleotides. In another embodiment, the length is 9-15 nucleotides. In another embodiment, the length is 10-15 nucleotides. In another embodiment, the length is 11-15 nucleotides. In another embodiment, the length is 7-13 nucleotides. In another embodiment, the length is 8-13 nucleotides. In another embodiment, the length is 9-13 nucleotides. In another embodiment, the length is 10-13 nucleotides. Each possibility represents a separate embodiment of the present invention.

"Substantially random" refers, in another embodiment, to a sequence constructed by a random process, e.g. use of pools of mixed nt in an oligonucleotide synthesizer. In another embodiment, the term refers to a lack of detectable sequence bias. In another embodiment, the term encompasses a minimal sequence bias. Each possibility represents a separate embodiment of the present invention.

"Non self-complementary" refers, in another embodiment, to a sequence that is not palindromic. In another embodiment, the term encompasses a sequence that is partially self-complementary and also contains a non self-complementary region. In another embodiment, the term encompasses a sequence that is partially self-complementary and also contains a (non self-complementary) loop-forming region. Each possibility represents a separate embodiment of the present invention.

"Substantially complementary" refers, in another embodiment, to a sequence that hybridizes with another sequence under the conditions used in a method of present invention. In another embodiment, the term encompasses a sequence complementary to another sequence with the exception of an overhang. In another embodiment, the sequence is complementary to the other sequence with the exception of 1-2 mismatches. In another embodiment, the sequences are complementary except for 1 mismatch. In another embodiment, the sequences are complementary except for 2 mismatches. In another embodiment, the sequences are complementary except for 3 mismatches. In another embodiment, the sequences are complementary except for more than 3 mismatches. Each possibility represents a separate embodiment of the present invention.

In another embodiment, the recombinant expression vectors further comprise a promoter of an RNA polymerase. In another embodiment, each of the recombinant expression vectors further comprises a promoter of an RNA polymerase. Each possibility represents another embodiment of the present invention.

In another embodiment, the recombinant expression vectors of methods and compositions of the present invention are capable of expressing a set or library of RNA molecules. In another embodiment, the recombinant expression vectors are capable of expressing the set or library of RNA molecules when a cell population is contacted with them or transduced with them. Each possibility represents a separate embodiment of the present invention.

In another embodiment, the recombinant expression vectors further comprise a gene encoding an inhibitory RNA (RNAi) molecule of known function. In another embodiment, each of the recombinant expression vectors further comprises a gene encoding an RNAi molecule of known function. In another embodiment, a majority of the set or library of recombinant expression vectors further comprises a gene encoding an RNAi molecule of known function. Each possibility represents another embodiment of the present invention.

In another embodiment, the RNA molecules produced by the set or library of recombinant expression vectors comprise a loop-forming region, wherein the loop-forming region connects the two strands of the double-stranded region of random sequence. In another embodiment, the loop-forming region is not palindromic. Each possibility represents another embodiment of the present invention.

"Palindromic," in one embodiment, refers to a single-stranded nucleic acid molecule having a sequence that is the same sequence as the reverse complement of itself. The sequence AAGGCCTT is an example of a palindrome.

In another embodiment, as exemplified herein in Example 5, the present invention provides a method of generating a set or library of recombinant expression vectors, wherein the set or library of recombinant expression vectors expresses a set or library of ribonucleic acid (RNA) molecules, the method comprising the steps of:

a. obtaining a nucleic acid intermediate II from a single-stranded nucleic acid intermediate I, wherein the single-stranded nucleic acid intermediate I comprises: (i) a first constant region; (ii) a variable region; and (iii) a second constant region;

and wherein the nucleic acid intermediate II, comprises: (i) the single-stranded nucleic acid intermediate I; (ii) an intervening region; and (iii) a region that hybridizes with the single-stranded nucleic acid intermediate I; and b. obtaining a double-stranded intermediate III from the nucleic acid intermediate II, comprising the nucleic acid intermediate II and a nucleic acid molecule that hybridizes with the nucleic acid intermediate II, and wherein the double-stranded intermediate III comprises the following double-stranded regions: (i) a first copy of the first constant region or a fragment thereof; (ii) a first copy of the variable region; (iii) a first copy of the second constant region; (iv) a copy of the intervening region; (v) a second, inverted copy of the second constant region; (vi) a second, inverted copy of the variable region; and (vii) a second, inverted copy of the first constant region or a fragment thereof;

wherein the first, double-stranded copy of the second constant region and the second, inverted double-stranded copy of the second constant region have a restriction enzyme site asymmetry, such that:

(ii) the first copy of the second constant region, but not the second, inverted copy of the second constant region, is a substrate for a first restriction enzyme, and;

(iii) the second, inverted copy of the second constant region, but not the first copy of the second constant region, is a substrate for a second restriction enzyme;

thereby generating a set or library of recombinant expression vectors, wherein the set or library of recombinant expression vectors expresses a set or library of RNA molecules. In another embodiment, the 3 components listed above of the single-stranded nucleic acid intermediate I are ordered in the single-stranded nucleic acid intermediate I in 5' to 3' order as listed. In another embodiment, the 3 components listed above of the nucleic acid intermediate II are ordered in the nucleic acid intermediate II in 5' to 3' order as listed. In another embodiment, the 7 components listed above of the double-stranded intermediate III are ordered in the double-stranded intermediate III in order as listed. Each possibility represents another embodiment of the present invention.

In another embodiment, as exemplified herein in Example 5, the present invention provides a method of generating a set or library of recombinant expression vectors, wherein the set or library of recombinant expression vectors is capable of expressing a set or library of RNA molecules, the method comprising the steps of:

(a) synthesizing a nucleotide intermediate I, comprising:
  (i) a variable region 6-30 nucleotides in length, wherein either: (1) the sequence of the variable region is substantially random; or (2) the variable region comprises a first sub-region of substantially random sequence and a second sub-region common to the set or library of recombinant expression vectors;
  (ii) a constant, non-palindromic region 3-20 nucleotides in length; and
  (iii) a complementary region, wherein the complementary region is capable of hybridizing with the variable region;

(b) synthesizing a second nucleotide molecule capable of hybridizing with the nucleotide intermediate I; and (c) annealing the nucleotide intermediate I with the second nucleotide molecule, thereby generating a double-stranded product, the double-stranded product comprising double-stranded copies of the variable region, the constant, non-palindromic region, and the complementary region, thereby generating a set or library of recombinant expression vectors, wherein the set or library of recombinant expression vectors is capable of expressing a set or library of RNA molecules. In another embodiment, the sequences of nucleotide intermediate I and the second nucleotide molecule are generated using a computer. In another embodiment, the sequences are generated using any other method known in the art. Each possibility represents a separate embodiment of the present invention.

In another embodiment, each end of the double-stranded product further comprises a feature independently selected from a restriction enzyme recognition site and a sticky end. In another embodiment, the features flank the double-stranded copies of the variable region, the constant, non-palindromic region, and the complementary region. End, in another embodiment, refers to a position within about 10 nucleotides of the absolute end. In another embodiment, the term refers to a position at the absolute end. In another embodiment, the term encompasses any positions flanking the double-stranded copies of the variable region, the constant, non-palindromic region, and the complementary region. Each possibility represents a separate embodiment of the present invention.

In another embodiment, the variable region of an RNA molecule of the present invention exhibits substantially random sequence throughout its length. In another embodiment, the variable region comprises a first sub-region of substantially random sequence and a second sub-region common to said set or library of recombinant expression vectors. Each possibility represents a separate embodiment of the present invention.

The nucleic acid intermediate II of methods and compositions of the present invention is, in another embodiment, single-stranded. In another embodiment, the nucleic acid intermediate II has partial double-stranded structure. In another embodiment, the nucleic acid intermediate II has a hairpin structure. In another embodiment, a method of the present invention comprises the step of opening a partial double-stranded structure of nucleic acid intermediate II, to facilitate a subsequent step. Each possibility represents a separate embodiment of the present invention.

An example of a first and a second restriction enzyme are PmeI and AarI, respectively, in the method described in Example 5. It will be understood to those skilled in the art that a variety of restriction enzymes are suitable for this method.

In another embodiment, the present invention provides a method of generating a set or library of recombinant expression vectors, wherein the set or library of recombinant expression vectors expresses a set or library of RNA molecules, the method comprising the steps of:

a. obtaining a nucleic acid intermediate II from a single-stranded nucleic acid intermediate I, wherein the single-stranded nucleic acid intermediate I comprises: (i) a first constant region; (ii) a region of random sequence; and (iii) a second constant region;

and wherein the nucleic acid intermediate II, comprises: (i) the single-stranded nucleic acid intermediate I; (ii) an intervening region; and (iii) a region that hybridizes with the single-stranded nucleic acid intermediate I;

b. obtaining a double-stranded intermediate III from the nucleic acid intermediate II, comprising the nucleic acid intermediate II and a nucleic acid molecule that hybridizes with the nucleic acid intermediate II, and wherein the double-stranded intermediate III comprises: (i) a first, double-stranded copy of the first constant region or a fragment thereof; (ii) a first, double-stranded copy of the region of random sequence; (iii) a first, double-stranded copy of the second constant region; (iv) a double-stranded copy of the intervening region; (v) a second, inverted double-stranded copy of the second constant region; (vi) a second, inverted double-stranded copy of the region of random sequence; and (vii) a second, inverted double-stranded copy of the first constant region or a fragment thereof;

wherein the first, double-stranded copy of the second constant region and the second, inverted double-stranded copy of the second constant region have a restriction enzyme site asymmetry, such that:

(i) the first, double-stranded copy of the second constant region, but not the second, inverted double-stranded copy of the second constant region, is a substrate for a first restriction enzyme, and;

(ii) the second, inverted, double-stranded copy of the second constant region, but not the first double-stranded copy of the second constant region, is a substrate for a second restriction enzyme; and c. engineering a set or library of recombinant expression vectors to contain the double-stranded intermediate III or a fragment thereof, thereby generating a set or library of recombinant expression vectors, wherein the set or library of recombinant expression vectors expresses a set or library of RNA molecules. In another embodiment, the 3 components listed above of the single-stranded nucleic acid intermediate I are ordered in the single-stranded nucleic acid intermediate I in 5' to 3' order as listed. In another embodiment, the 3 components listed above of the nucleic acid intermediate II are ordered in the nucleic acid intermediate II in 5' to 3' order as listed. In another embodiment, the 7 components listed above of the double-stranded intermediate III are ordered in the double-stranded intermediate III in order as listed. Each possibility represents another embodiment of the present invention.

In another embodiment, each RNA molecule in the set or library comprises a double-stranded region of random sequence.

Figure 6:
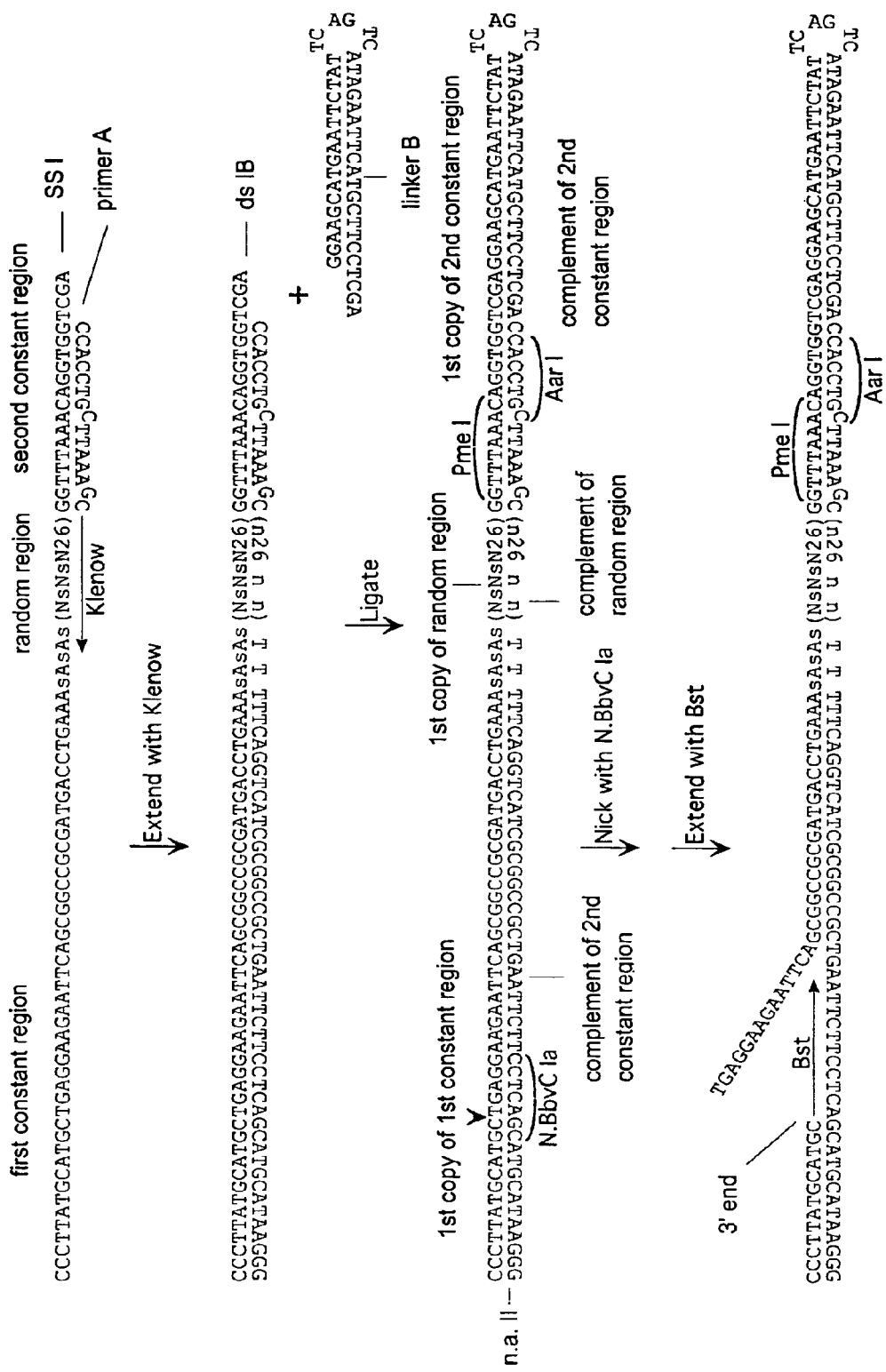
FIG. 6. Third approach for creation of a library of partially self-complementary RNA molecules, part I. Described in Example 5. Sequences of 10 or more nt and not previously assigned a SEQ ID No are listed as SEQ ID No: 34-37.
Figure 7:
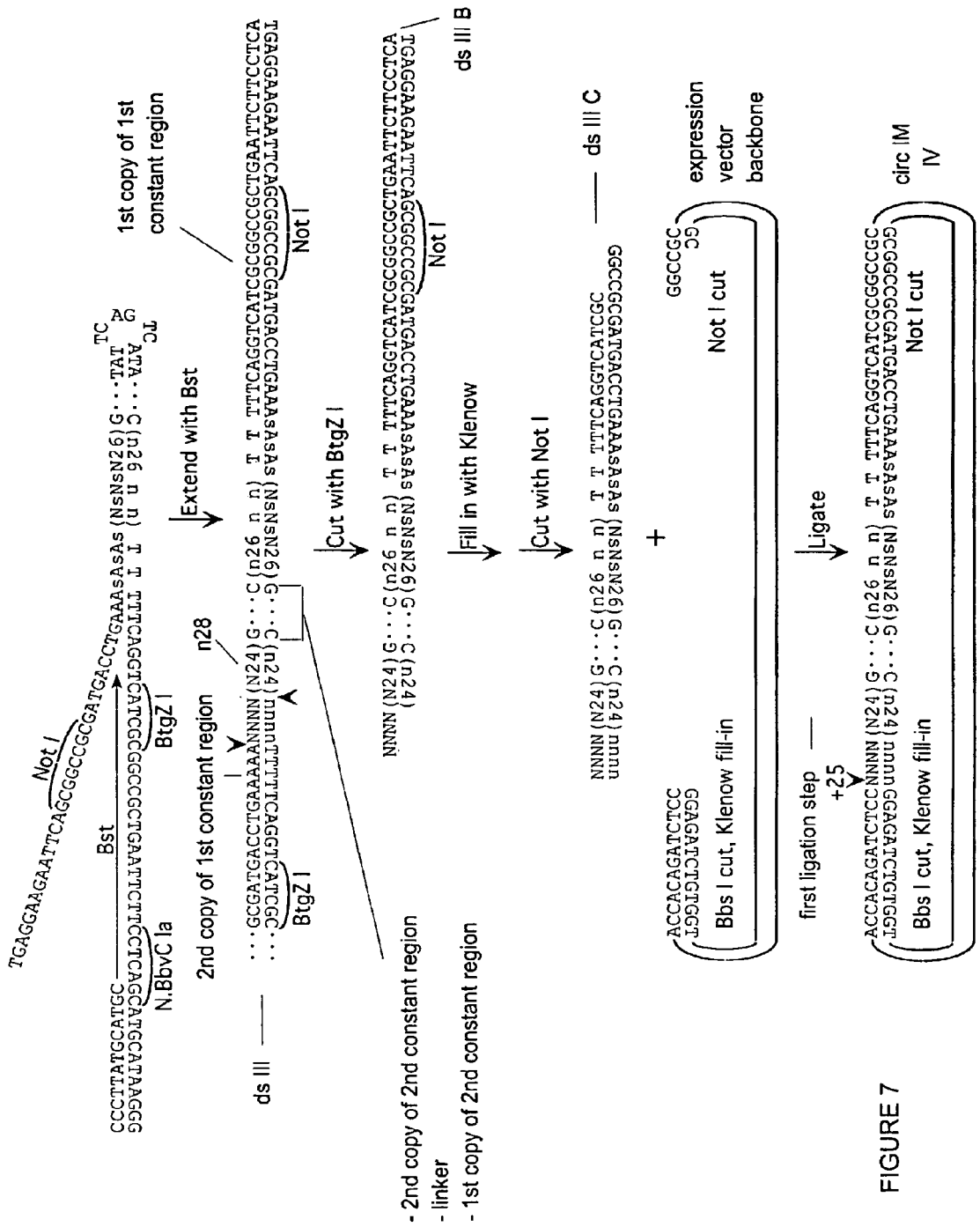
FIG. 7. Third approach for creation of a library of partially self-complementary RNA molecules, part II. Described in Example 5. Sequences of 10 or more nt and not previously assigned a SEQ ID No are listed as SEQ ID No: 38-51.
Figure 8:
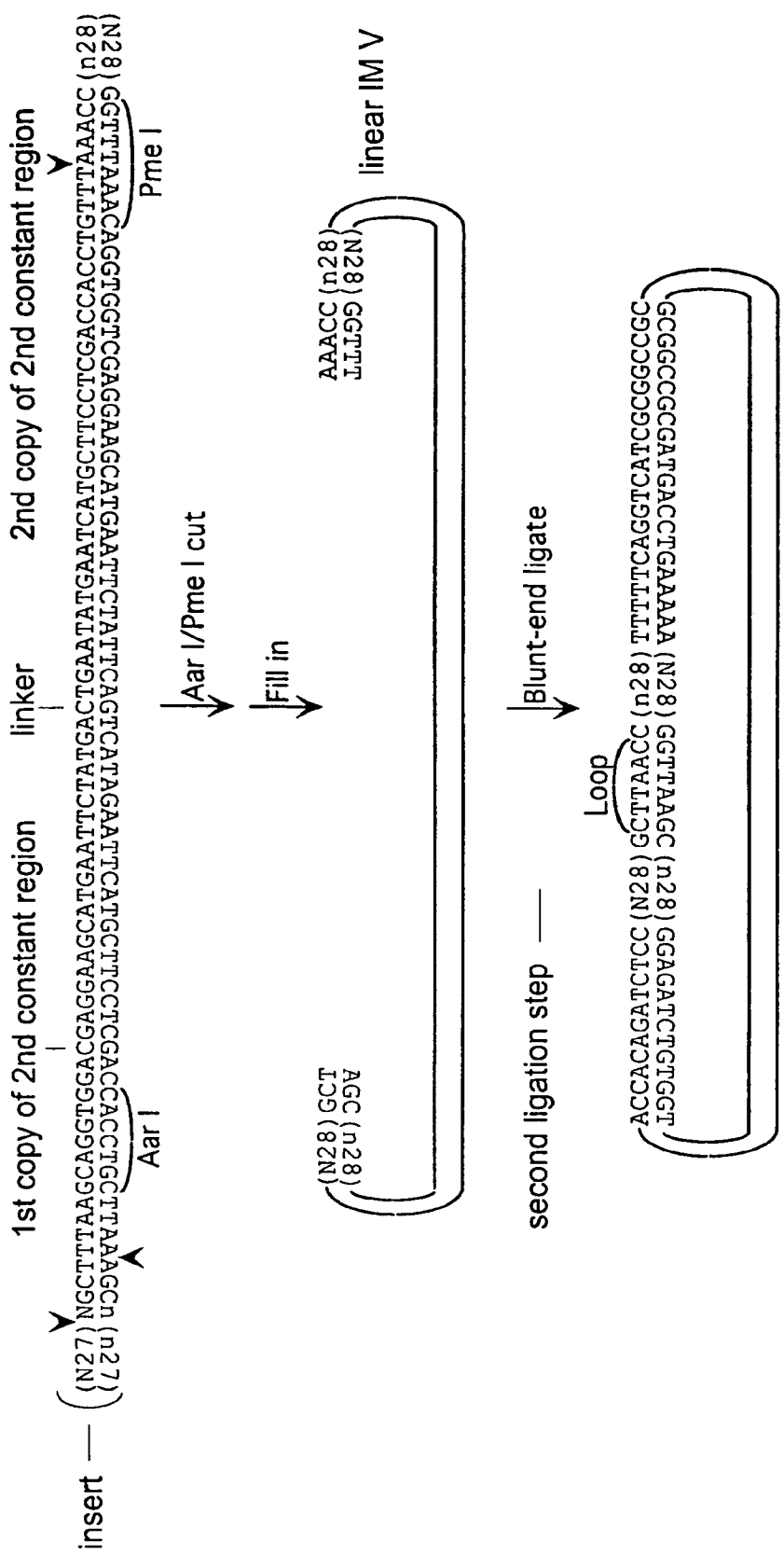
FIG. 8. Third approach for creation of a library of partially self-complementary RNA molecules, part III. Described in Example 5. Sequences of 10 or more nt and not previously assigned a SEQ ID No are listed as SEQ ID No: 52-53.

In another embodiment, one of the above methods is performed as depicted in FIGS. 6-8. In another embodiment, not all the steps depicted in FIGS. 6-8 are performed in a method of the present invention. Each possibility represents a separate embodiment of the present invention.

"Single-stranded," in another embodiment, refers to a nucleic acid molecule wherein all the nucleotide bases are connected to one another by covalent bonds. The term includes, in another embodiment, nucleic acid molecules with partial double stranded character. In another embodiment, the term includes nucleic acid molecules that are mostly double stranded. In another embodiment, the term includes nucleic acid molecules comprising a double-stranded region. Each possibility represents another embodiment of the present invention.

In another embodiment of methods and compositions of the present invention, the terms "first copy [/copies]," "second copy [/copies]," refer to identical copies of a region, nucleotide molecule, etc. In another embodiment, "copy" refers to an approximate copy. In another embodiment, a second copy of a sequence contains a mismatch with respect to the first copy of the sequence. In another embodiment, the second copy contains 2 mismatches relative to the first copy. In another embodiment, the second copy contains more than 1 mismatch relative to the first copy. In another embodiment, the second copy contains more than 2 mismatches relative to the first copy. In another embodiment, the first and second copies are at least 60% homologous to one another. In another embodiment, the copies are at least 70% homologous to one another. In another embodiment, the copies are at least 80% homologous to one another. In another embodiment, the copies are at least 90% homologous to one another. In another embodiment, the copies are 100% homologous to one another. Each possibility represents a separate embodiment of the present invention.

In another embodiment of methods and compositions of the present invention, the second, inverted double-stranded copy of the second constant region is an exact copy of the first copy of the second constant region. In another embodiment, the second, inverted double-stranded copy is an approximate copy of the first copy. Each possibility represents a separate embodiment of the present invention.

In another embodiment of methods and compositions of the present invention, the second, inverted double-stranded copy of the region of random sequence is an exact copy of the first copy of the region of random sequence. In another embodiment, the second, inverted double-stranded copy is an approximate copy of the first copy. Each possibility represents a separate embodiment of the present invention.

In another embodiment of methods and compositions of the present invention, the second, inverted double-stranded copy of the first constant region or fragment thereof is an exact copy of the first copy of the first constant region or fragment thereof. In another embodiment, the second, inverted double-stranded copy is an approximate copy of the first copy. Each possibility represents a separate embodiment of the present invention.

In another embodiment, as exemplified herein in Examples 3-5, the step of obtaining a nucleic acid intermediate I comprises the steps of:
a. obtaining a double-stranded intermediate I B from the single-stranded nucleic acid intermediate I, the double-stranded intermediate I B comprising the single-stranded nucleic acid intermediate I and an additional single-stranded nucleic acid molecule, wherein the additional single-stranded nucleic acid molecule hybridizes with the single-stranded nucleic acid intermediate I; and
b. obtaining the nucleic acid intermediate II from the double-stranded intermediate I B.

In another embodiment, the nucleic acid intermediate II is obtained without utilizing a double-stranded intermediate I B. (e.g. by using a 2nd constant region that is hairpin shaped).

In another embodiment, the nucleic acid intermediate II is obtained from the single-stranded nucleic acid intermediate I by any other method known in the art. Each method of obtaining the nucleic acid intermediate II represents a separate embodiment of the present invention.

In another embodiment, the step of obtaining the double-stranded intermediate I B comprises the steps of (a) annealing a primer to the second constant region of the single-stranded nucleic acid intermediate I and (b) extending the primer. In another embodiment, the primer contains one or more mismatched residues with respect to the second constant region. In another embodiment, the 5' end of the primer does not align precisely with the 3' end of the single-stranded nucleic acid intermediate I. Each possibility represents another embodiment of the present invention.

In another embodiment, the step of obtaining the nucleic acid intermediate II from the double-stranded intermediate I B comprises ligating a linker nucleic acid molecule to the 3' end of the single-stranded nucleic acid intermediate I and the 5' end of the additional single-stranded nucleic acid molecule. In another embodiment, the linker nucleic acid molecule is hairpin-shaped. In another embodiment, the linker nucleic acid molecule is not hairpin-shaped. Each possibility represents another embodiment of the present invention.

In another embodiment of methods of the present invention, the double-stranded intermediate I B and linker nucleic acid molecule each contain half sites of different restriction enzymes, having different consensus sequences, with blunt ends or with compatible sticky ends; thus, the properly ligated product is not a substrate for either of the enzymes, while homodimers of either the extended primer or the hairpin loop linker are cut; then size separation is used to purify properly ligated products. Each possibility represents a separate embodiment of the present invention. A sticky end was used in Examples 3-5 for convenience only and is not critical to methods of present invention.

The nucleic acid intermediate II of methods and compositions of the present invention has, in another embodiment, a hairpin structure. In another embodiment, the nucleic acid intermediate II has a double-stranded structure. In another embodiment, the nucleic acid intermediate II has a single-stranded structure. In another embodiment, the nucleic acid intermediate II is single stranded, but has double-stranded secondary structure (Example 5). In another embodiment, the nucleic acid intermediate II initially has a double-stranded structure, but is opened into a single-stranded structure in the course of a method of the present invention (Examples 3 and 4). Each possibility represents another embodiment of the present invention.

In another embodiment of methods and compositions of the present invention, a circular intermediate IV is obtained from the double-stranded (ds) intermediate III, the circular intermediate IV comprising an expression vector backbone and, as an insert, either: (a) the ds intermediate III; or (b) a fragment of the ds intermediate III, wherein the fragment comprises the first, ds copy of the region of random sequence and the second, inverted ds copy of the region of random sequence. In another embodiment, the fragment of ds intermediate III further comprises all the sequence of ds intermediate III between the first and second ds copies of the region of random sequence. In another embodiment, the circular intermediate IV comprises (a) the first, ds copy of the region of random sequence; (b) the second, inverted ds copy of the region of random sequence; and (c) a fragment of the sequence of ds intermediate III therebetween. In another embodiment, the circular intermediate IV is obtained from the ds intermediate III by ligation. Each possibility represents a separate embodiment of the present invention.

In another embodiment of methods and compositions of the present invention, a circular product is obtained from the ds intermediate III, the circular product comprising an expression vector backbone and, as an insert, either: (a) the ds intermediate III; or (b) a fragment of the ds intermediate III, wherein the fragment comprises the first, ds copy of the region of random sequence and the second, inverted ds copy of the region of random sequence. In another embodiment, the fragment of ds intermediate III further comprises all the sequence of ds intermediate III between the first and second ds copies of the region of random sequence. In another embodiment, the circular product comprises (a) the first, ds copy of the region of random sequence; (b) the second, inverted ds copy of the region of random sequence; and (c) a fragment of the sequence of ds intermediate III therebetween. In another embodiment, the circular product is obtained from the ds intermediate III by ligation. Each possibility represents a separate embodiment of the present invention.

In another embodiment of methods and compositions of the present invention, the circular intermediate IV is digested with the first restriction enzyme and the second restriction enzyme described hereinabove, thereby-generating a linear intermediate V.

In another embodiment of methods and compositions of the present invention, the linear intermediate V is intra-molecularly ligated, thereby generating a circular product VI. In another embodiment, as exemplified herein in Example 5, the intra-molecular ligation generates an expression vector that expresses a transcript comprising: (i) the region of random sequence of single-stranded nucleic acid intermediate I; (ii) a non-palindromic intervening region; and (iii) a region that hybridizes with the region of random sequence. In another embodiment, the non-palindromic intervening region is a fragment of the intervening region of nucleic acid intermediate II. In another embodiment, the non-palindromic intervening region is capable of forming a loop. In another embodiment, the 3 components listed above of the linear intermediate V are ordered in the transcript in 5' to 3' order as listed. Each possibility represents a separate embodiment of the present invention.

Each possible additional step represents another embodiment of the present invention.

In another embodiment, as exemplified herein in Example 5, the present invention provides a method of generating a set or library of recombinant expression vectors, wherein the set or library of recombinant expression vectors expresses a set or library of RNA molecules, the method comprising the steps of:
(a) obtaining a double-stranded intermediate I B from a single-stranded nucleic acid intermediate I, wherein the single-stranded nucleic acid intermediate I comprises, in 5' to 3' order: (i) a first constant region; (ii) a region of random sequence; and (iii) a second constant region,
  wherein the double-stranded intermediate I B comprises the single-stranded nucleic acid intermediate I and an additional single-stranded nucleic acid molecule, wherein the additional single-stranded nucleic acid molecule hybridizes with the single-stranded nucleic acid intermediate I;
(b) obtaining a nucleic acid intermediate II from the double-stranded intermediate I B, the nucleic acid intermediate II comprising: (i) the single-stranded nucleic acid intermediate I; (ii) an intervening region; and (iii) the additional single-stranded nucleic acid molecule;
(c) obtaining a double-stranded intermediate III from the nucleic acid intermediate II, the double-stranded intermediate m comprising the nucleic acid intermediate II and a third single-stranded nucleic acid molecule, wherein the third single-stranded nucleic acid molecule hybridizes with the nucleic acid intermediate II, and wherein the double-stranded intermediate III comprises:
  (i) a first, double-stranded copy of the first constant region or a fragment thereof; (ii) a first, double-stranded copy of the region of random sequence; (iii) a first, double-stranded copy of the second constant region; (iv) a double-stranded copy of the intervening region; (v) a second, inverted double-stranded copy of the second constant region; (vi) a second, inverted double-stranded copy of the region of random sequence; and (vii) a second, inverted double-stranded copy of the first constant region or a fragment thereof;
  wherein the first, double-stranded copy of the second constant region and the second, inverted double-stranded copy of the second constant region have a restriction enzyme site asymmetry, such that:
    (i) the first, double-stranded copy of the second constant region, but not the second, inverted double-stranded copy of the second constant region, is a substrate for a first restriction enzyme, and;
    (ii) the second, inverted, double-stranded copy of the second constant region, but not the first double-stranded copy of the second constant region, is a substrate for a second restriction enzyme;
(d) obtaining a circular intermediate IV from the double-stranded intermediate III, the circular intermediate IV comprising an expression vector backbone and, as an insert, the double-stranded intermediate III or a fragment thereof;
(e) digesting the circular intermediate IV with the first restriction enzyme and the second restriction enzyme, thereby generating a linear intermediate V; and
(f) intra-molecularly ligating the linear intermediate V, thereby generating an expression vector that expresses a transcript comprising, in 5' to 3' order: (i) the first, double-stranded copy of the second constant region; (ii) a loop-forming region; (iii) the second, inverted double-stranded copy of the second constant region,
thereby generating a set or library of recombinant expression vectors, wherein the set or library of recombinant expression vectors expresses a set or library of RNA molecules. In another embodiment, the 3 components listed above of the single-stranded (ss) nucleic acid intermediate I are ordered in ss nucleic acid intermediate I in 5' to 3' order as listed. In another embodiment, the 3 components listed above of the nucleic acid intermediate II are ordered in the nucleic acid intermediate II in 5' to 3' order as listed. In another embodiment, the 7 components listed above of the double-stranded intermediate III are ordered in ds intermediate III in order as listed. Each possibility represents another embodiment of the present invention.

In another embodiment, individual RNA molecules encoded by the set or library comprise a double-stranded region of random sequence and a loop forming region between the 2 complementary strands of the region of random sequence. In another embodiment, each RNA molecule in the set or library comprises a double-stranded region of random sequence and a loop forming region between the 2 complementary strands of the region of random sequence. Each possibility represents a separate embodiment of the present invention.

In another embodiment, the above method is performed as depicted in FIGS. 6-8. In another embodiment, not all the steps depicted in FIGS. 6-8 are performed in a method of the present invention. Each possibility represents a separate embodiment of the present invention.

In another embodiment of methods and compositions of the present invention, the single-stranded nucleic acid intermediate I is generated by programming a nucleotide synthesizer to synthesize the following: 1) the sequence of the first constant region, 2) the random region, using a mixture of nucleotides at each position, 3) and the sequence of the second constant region. In another embodiment, ss n.a. intermediate I is generated by any other method known in the art. Each method represents a separate embodiment of the present invention.

In another embodiment of methods and compositions of the present invention, as exemplified herein in Examples 3-5, each of the nucleic acid molecules and intermediates utilized in a method of the present invention is composed of DNA or of a version of DNA with an altered backbone or base composition (in another embodiment, a phosphorothioate bond)

along part or all of its length. Each possibility represents a separate embodiment of the present invention.

"Constant" refers, in another embodiment, to a region that is unchanged or invariant within a library or set of nucleic acid molecules. In another embodiment, "constant" refers to a region that is unchanged or invariant within a subset of a library of nucleic acid molecules. For example, the starting nucleotide molecule in the methods depicted in FIGS. 1-8 each has 2 constant regions, one 5' to the random region and one 3' to the random region. In another embodiment, the term encompasses slight variations that occur between otherwise constant regions within a library. In another embodiment, the first constant region and second constant region of a nucleotide molecule of the present invention each have different, constant sequences. In another embodiment, the first constant region and/or second constant region are substantially constant within the library. Each possibility represents a separate embodiment of the present invention.

In another embodiment, the present invention provides a method for generating an expression vector for an RNA molecule comprising a double-stranded region of random sequence, similar to the above method, but wherein the double-stranded intermediate III is digested or otherwise treated to remove most of the intervening sequence between the 2 copies of the region of random sequence, prior to insertion into the expression vector backbone. All embodiments enumerated hereinabove apply to this method as well.

In another embodiment of the methods mentioned above, the fragment of ds intermediate III that is used to form circular intermediate IV comprises the first, ds copy of the region of random sequence and the second, inverted ds copy of the region of random sequence. In another embodiment, the fragment comprises the 5 middle parts of ds intermediate III (e.g. (ii) a first, ds copy of the region of random sequence; (iii) a first, ds copy of the second constant region; (iv) a ds copy of the intervening region; (v) a second, inverted ds copy of the second constant region; and (vi) a second, inverted ds copy of the region of random sequence). In another embodiment, the fragment comprises all 7 of the parts of ds intermediate III (e.g. (i) a first, ds copy of the first constant region or a fragment thereof; (ii) a first, ds copy of the region of random sequence; (iii) a first, ds copy of the second constant region; (iv) a ds copy of the intervening region; (v) a second, inverted ds copy of the second constant region; (vi) a second, inverted ds copy of the region of random sequence; and (vii) a second, inverted ds copy of the first constant region or a fragment thereof). In another embodiment, as exemplified herein in Example 5, the fragment comprises 6 of the 7 parts of ds intermediate III (e.g. (ii) a first, ds copy of the region of random sequence; (iii) a first, ds copy of the second constant region; (iv) a ds copy of the intervening region; (v) a second, inverted ds copy of the second constant region; (vi) a second, inverted ds copy of the region of random sequence; and (vii) a fragment of a second, inverted ds copy of the first constant region. Each possibility represents a separate embodiment of the present invention.

"Hybridizes," in another embodiment of methods and compositions of the present invention, refers to a molecule that hybridizes with the target molecule under the conditions wherein the method of the invention is carried out. For example, as exemplified herein in Examples 3-5, each of the double-stranded intermediates utilized comprises a new strand that hybridizes with the previous intermediate. In another embodiment, the term refers to hybridization under stringent conditions. In another embodiment, the term refers to hybridization under moderate conditions. In another embodiment, the term "hybridizes under stringent conditions" refers to conditions for hybridization and washing under which a double-stranded nucleotide molecule 18 residues in length and 60% self-complementary typically remains hybridized. In another embodiment, a double-stranded nucleotide molecule 18 residues in length and 70% self-complementary is utilized. In another embodiment, a double-stranded nucleotide molecule 18 residues in length and 80% self-complementary is utilized. In another embodiment, the term is defined according to any other definition thereof known in the art. Each possibility represents a separate embodiment of the present invention.

In another embodiment, the first constant region of the methods mentioned above or a corresponding constant region of an analogous method of the present invention, when in double-stranded form, is a substrate for a nicking endonuclease. In another embodiment, the nicking endonuclease is a DNA nicking endonuclease. In another embodiment, the nicking endonuclease is Nb.BbvC I. In another embodiment, as exemplified herein in Example 5, the step of obtaining the double-stranded intermediate III comprises contacting the nucleic acid intermediate II with the nicking endonuclease, thereby generating a 3' end suitable for use as primer; and extending the primer. In another embodiment, the nucleic acid intermediate II is digested with the nicking endonuclease. Each possibility represents a separate embodiment of the present invention.

In another embodiment of methods and compositions of the present invention, as exemplified herein in Example 5, the step of extending is performed by a polymerase that has a strand displacement activity. In another embodiment, the polymerase has a high strand displacement activity. In another embodiment, the polymerase with strand displacement activity is a DNA polymerase. In another embodiment, the polymerase is phi29. In another embodiment, the polymerase is Bst. In another embodiment, the polymerase is Vent. In another embodiment, the Vent is exo-. In another embodiment, the polymerase is 9 oNm. In another embodiment, the polymerase is any other polymerase known in the art with strand displacement activity. In another embodiment, the polymerase is a highly processive polymerase. In another embodiment, a DNA polymerase that can perform strand displacement replication in the presence of a strand displacement factor is suitable for use in the method, even if the DNA polymerase does not perform strand displacement replication in the absence of such a factor. Each possibility represents a separate embodiment of the present invention.

"Strand displacement activity" refers, in another embodiment, to an ability to displace downstream DNA encountered during synthesis.

"Highly processive" refers, in another embodiment, to a polymerase capable of continuous synthesis of long stretches of DNA under the conditions utilized. In another embodiment, the polymerase is capable of continuous synthesis of over 1 kilobase of DNA. Each possibility represents a separate embodiment of the present invention.

In another embodiment, the nicking endonuclease utilized in methods and compositions of the present invention is Nb.Bsm I. In another embodiment, the nicking endonuclease is Nt.Alw I. In another embodiment, the nicking endonuclease is Nt.BbvC I. In another embodiment, the nicking endonuclease is Nt.BstNB I. In another embodiment, the nicking endonuclease is Nb.BsrDI. In another embodiment, the nicking endonuclease is Nb.BtsI. In another embodiment, the nicking endonuclease is any other nicking endonuclease known in the art. Each possibility represents a separate embodiment of the present invention.

In another embodiment of methods and compositions of the present invention, the step of obtaining the double-stranded intermediate I B comprises the steps of (a) annealing a primer to the second constant region of the single-stranded nucleic acid intermediate I and (b) extending the primer. In another embodiment, the primer contains one or more mismatches with respect to the second constant region. Each possibility represents a separate embodiment of the present invention.

In another embodiment, as exemplified herein in Examples 3-5, the 5' end of a primer used in methods and compositions of the present invention does not align precisely with the 3' end of its target nucleic acid molecule. In another embodiment, this intentional mis-alignment generates a double stranded (ds) nucleic acid molecule that contains a "sticky end" that is useful in sub-cloning. Each possibility represents a separate embodiment of the present invention. "Sticky end" refers, in one embodiment, to an end with an overhang. "Blunt end" refers, in one embodiment, to an end without an overhang. Each possibility represents a separate embodiment of the present invention.

In another embodiment, as exemplified herein in Examples 3-5, the step of obtaining the nucleic acid intermediate II of the methods mentioned above or a corresponding intermediate of an analogous method of the present invention comprises ligating a linker nucleic acid molecule to the 3' end of the single-stranded nucleic acid intermediate I and the 5' end of the additional single-stranded nucleic acid molecule. In another embodiment, the linker nucleic acid molecule is hairpin-shaped. In another embodiment, the linker nucleic acid molecule is single-stranded. In another embodiment, the linker nucleic acid molecule, together with the single-stranded nucleic acid intermediate I and additional single-stranded nucleic acid molecule, forms a larger hairpin-shaped structure. Each possibility represents a separate embodiment of the present invention.

In other embodiments, if homo-dimers of the hairpin-loop linker anneal inter-molecularly and extend, this occurrence is minimized by pre-heating them to melting temperature, cooling them, and then bringing them up to ligation temperature.

In another embodiment, as exemplified herein in Example 3, the step of obtaining the ds intermediate III of the methods mentioned above or a corresponding intermediate of an analogous method of the present invention comprises annealing a primer to the nucleic acid intermediate II and extending the primer, thereby synthesizing a third single-stranded nucleic acid molecule. In another embodiment, the step of extending is performed with a strand displacing polymerase. Each possibility represents a separate embodiment of the present invention.

In another embodiment, the primer contains one or more mismatches with respect to nucleic acid intermediate II. In another embodiment, the mismatch(es) creates a restriction enzyme site asymmetry between nucleic acid intermediate II and the third ss nucleic acid molecule. Each possibility represents a separate embodiment of the present invention.

As an example of restriction site asymmetry, as exemplified herein in Example 5, the circular intermediate IV has a restriction site asymmetry, such that the first copy of the second constant region is a substrate for Aar I (but not Pme I), and the second copy of the second constant region is a substrate for Pme I (but not Aar I). In this case, the asymmetry was created by the mismatched primer used to generate ss I B. It will be understood to those skilled in the art that a variety of restriction enzymes are suitable for this method.

In another embodiment of methods and compositions of the present invention, restriction enzyme site asymmetry is generated by incorporating a mismatched residue(s) between 2 otherwise complementary nucleotide molecules utilized in methods and compositions of the present invention, in a region that will correspond to a recognition site or a cutting site of a restriction enzyme, such that the product of subsequently copying each strand has an asymmetric sequence. For example, in another embodiment, in the methods mentioned above, a mismatched residue(s) is incorporated between the ss nucleic acid intermediate I and it complementary strand. Consequently, in ds intermediate III, the first, double-stranded copy of the second constant region has a different sequence from the second, inverted double-stranded copy of the second constant region.

In another embodiment of methods and compositions of the present invention, restriction enzyme site asymmetry is generated by incorporating a residue with an altered backbone or base composition into a nucleotide molecule of the present invention, in a region that will correspond to a recognition site or a cutting site of a restriction enzyme. An example of an altered backbone is the phosphorothioate linkages of single-stranded nucleic acid intermediate I, as exemplified herein in Example 5. It will be understood to those skilled in the art that a variety of types of altered backbones are suitable for this method.

In another embodiment a residue with an altered backbone or base composition is incorporated into ss nucleic acid intermediate I. In another embodiment, a residue with an altered backbone or base composition is incorporated into the complement of ss nucleic acid intermediate I. Consequently, in ds intermediate III, either (i) the first, double-stranded copy of the second constant region or (ii) the second, inverted double-stranded copy of the second constant region comprises the residue with an altered backbone or base composition. In another embodiment, 1 bond of the backbone is altered. In another embodiment, 2 bonds of the backbone are altered. In another embodiment, more than 2 bonds of the backbone are altered. Each possibility represents a separate embodiment of the present invention.

The altered backbone utilized in methods and compositions of the present invention is, in one embodiment, a phosphorothioate backbone. In another embodiment, the altered backbone is a methyl phosphonate linkage. In another embodiment, the altered backbone is any other type of altered backbone known in the art that impedes restriction enzyme cutting. The altered base is, in another embodiment, any type of modified nucleoside, nucleoside analogue, or nucleic acid modification known in the art that impedes restriction enzyme cutting. Each possibility represents a separate embodiment of the present invention.

In another embodiment of methods and compositions of the present invention, restriction enzyme site asymmetry is generated by a combination of incorporation of a mismatched residue(s) and incorporation of a residue(s) with an altered backbone or base composition into a nucleotide molecule of the present invention. It will apparent to those skilled in the art that either or both methods can be used in methods of the present invention.

In another embodiment of methods and compositions of the present invention, restriction enzyme site asymmetry is generated by any other method known in the art of generating restriction enzyme site asymmetry. Each possibility represents a separate embodiment of the present invention.

In another embodiment, an intermediate utilized in methods and compositions of the present invention comprises an additional restriction enzyme site asymmetry between the first and second ds copies of the first constant region. In another embodiment, in the case of ds intermediate III, the first, ds copy of the first constant region or fragment thereof, but not the second, inverted ds copy of the first constant region or fragment thereof, is a substrate for a third restriction enzyme. In another embodiment, the additional restriction enzyme site asymmetry causes the second, double-stranded copy of the first constant region or fragment thereof ds intermediate III, but not the first, inverted double-stranded copy of the first constant region or fragment thereof, is a substrate for the third restriction enzyme.

Figure 4:
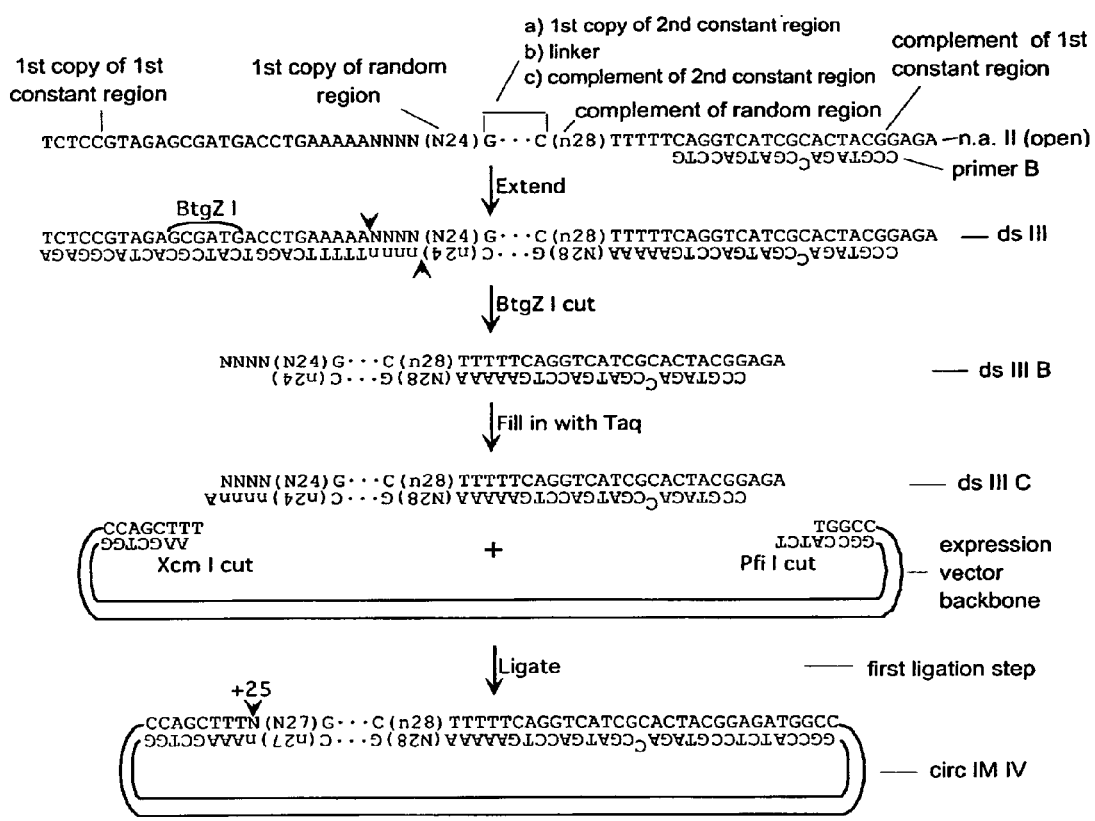
FIG. 4. Additional approach for creation of a library of partially self-complementary RNA molecules, part II. Described in Example 4. Sequences of 10 or more nt and not previously assigned a SEQ ID No are listed as SEQ ID No: 18-27.

For example, as exemplified herein in Example 5, the double-stranded intermediate III (ds III) has a restriction site asymmetry, such that the first copy of the first constant region is a substrate for BtgZ I (and, initially, Not I as well), and the second copy of the first constant region is a substrate for Not I (but not BtgZ I). In this case, the BtgZ I asymmetry was created by incorporation of phosphorothioated residues on ss nucleic acid intermediate I. Following asymmetric digestion of ds III with BtgZ I (generating ds IIIB), the Not I site was eliminated from the first copy of the first constant region, thus enabling asymmetric digestion of ds IIIB with Not I (FIG. 7). dsIII of the method described in Example 4 has an additional restriction enzyme site asymmetry, in this case generated by a mismatch in primer B (FIG. 4).

In another embodiment, a method of the present invention further comprises contacting the double-stranded intermediate III of the methods mentioned above or a corresponding intermediate of an analogous method of the present invention with the third restriction enzyme described above. In another embodiment, the step of contacting is performed prior to the step of obtaining the circular intermediate IV or a corresponding intermediate of an analogous method. In another embodiment, the double-stranded intermediate III is digested with the third restriction enzyme. In another embodiment, the step of contacting or digesting eliminates from the double-stranded intermediate III a fragment thereof or residue that is unfavorable for accurate transcription initiation from the expression vector. In another embodiment, the unfavorable fragment is a stretch of one or more consecutive purines (e.g. adenine) residues. In another embodiment, the stretch has 2 consecutive adenines. In another embodiment, the stretch has 3 consecutive adenines. In another embodiment, the stretch has 4 consecutive adenines. In another embodiment, the stretch has 5 consecutive adenines. In another embodiment, the stretch has 6 consecutive adenines. In another embodiment, the unfavorable fragment is an adenine-enriched region. In another embodiment of methods of the present invention, the promoter on the vector backbone is a promoter for transcription from the strand that formerly contained the adenine or 5 consecutive adenines. In another embodiment, the promoter in the vector initiates transcription from the strand that corresponds to the first single-stranded DNA molecule. Each possibility represents a separate embodiment of the present invention.

In another embodiment, as exemplified herein in Example 5, a stretch of 5 thymidines (e.g. produced by copying the 5 adenines in the first ss DNA molecule) follows the reverse complement of the region of random sequence in the gene encoding an RNA molecule of the present invention, enabling termination immediately following same. In another embodiment, the stretch of thymidines immediately follows the reverse complement of the region of random sequence. Thymidine residues in the coding strand of the DNA correspond to uridine residues in the transcribed RNA; thus, in this embodiment, the RNA contains a stretch of uridine residues. In another embodiment, transcription termination after the $2^{nd}$ uridine of a uridine stretch results in a 2-nt overhang on the RNA molecule. Each possibility represents a separate embodiment of the present invention.

In another embodiment, the additional restriction enzyme site asymmetry is generated by incorporating a residue with an altered backbone or base composition in the single-stranded nucleic acid intermediate I or the additional single-stranded nucleic acid molecule, whereby, in the double-stranded intermediate III, (i) the first, double-stranded copy of the first constant region or fragment thereof, or (ii) the second, inverted double-stranded copy of the first constant region or fragment thereof comprises the residue with an altered backbone or base composition. In another embodiment, the additional restriction enzyme site asymmetry is generated by a combination of incorporation of a mismatched residue(s) and incorporation of a residue(s) with an altered backbone or base composition into a nucleotide molecule of the present invention. In another embodiment, the additional restriction enzyme site asymmetry is generated by any other suitable method known in the art. Each possibility represents a separate embodiment of the present invention.

In another embodiment, as exemplified herein in Example 5, an expression vector of methods and compositions of the present invention further comprises a promoter of an RNA polymerase. In another embodiment, the expression vectors or set or library thereof are contacted with an RNA polymerase, thereby generating the RNA molecule or set or library thereof. In another embodiment, the expression vector or set or library thereof are introduced into a population of cells, wherein it is transcribed by an endogenous RNA polymerase. Each possibility represents a separate embodiment of the present invention.

In another embodiment, an expression vector of methods and compositions of the present invention further comprises a gene encoding an RNAi molecule of known function.

In another embodiment, the set or library of the expression vectors is a set or library of recombinant viruses. In another embodiment, the set of expression vectors is packaged as a recombinant virus. In another embodiment, copies of each of the set or library of the expression vectors are packaged as a set or library of recombinant viruses. Each possibility represents a separate embodiment of the present invention.

Each type of expression vector represents a separate embodiment of the present invention.

In another embodiment, an RNA molecule obtained by methods and compositions of the present invention is digested, wherein the digestion generates a short hairpin RNA (shRNA) molecule.

In another embodiment, the digestion occurs inside a target cell. In another embodiment, the digestion utilizes an endonuclease. Each possibility represents another embodiment of the present invention.

In another embodiment, as exemplified herein in Examples 6-7 and 10-16, the present invention provides a method for identifying an RNA molecule that has an ability to affect a biological parameter of interest, comprising the steps of (a) contacting a cell population with a set or library of the expression vectors of the present invention, wherein the set or library of the expression vectors, or a fraction thereof, is taken up by the cell population; and (b) determining or measuring the biological parameter of interest or a readout thereof in the cell population; whereby, if a cell in the cell population exhibits an alteration of the biological parameter of interest or readout thereof, then the cell carries a particular expression vector that encodes a particular RNA molecule that affects the biological parameter of interest.

In another embodiment of methods and compositions of the present invention, the RNA molecule functions via a known or understood mechanism of action. In another embodiment, the RNA molecule functions via a mechanism that is understood only following discovery of the RNA molecule. In another embodiment, the RNA molecule functions via an unknown mechanism. In another embodiment, screening methods of the present invention do not require knowledge or understanding of the mechanism of the RNA molecule, and thus enable entirely function-based screening, substantially eliminating or reducing bias from the sequences screened. Each possibility represents a separate embodiment of the present invention.

In another embodiment of methods and compositions of the present invention, a particular expression vector found to have biological activity or a fragment thereof is isolated or amplified, then the vector or a fragment thereof is sequenced. In another embodiment, the fragment comprises the coding sequence for the particular RNA molecule. Each possibility represents a separate embodiment of the present invention.

In another embodiment of methods and compositions of the present invention, as exemplified herein in Example 8, an additional cell is contacted with the particular expression vector, then the biological parameter of interest or readout thereof is determined or measured in the additional cell.

In another embodiment of methods and compositions of the present invention, a copy of the particular RNA molecule found to have biological activity is generated, an additional cell is contacted with the copy of the particular RNA molecule, then the biological parameter of interest or readout thereof is determined or measured in the additional cell.

In another embodiment of methods and compositions of the present invention, as exemplified herein in Example 8, a sequence that encodes the particular RNA molecule found to have biological activity, or a fragment thereof, is inserted or subcloned into a second expression vector backbone, thereby generating a second expression vector, wherein the second expression vector encodes either (i) the particular RNA molecule; or (ii) an altered version of the particular RNA molecule. In another embodiment, an additional cell is contacted with the second expression vector, and then the biological parameter of interest or readout thereof is determined or measured in the additional cell.

In another embodiment, the altered version of the particular RNA molecule comprises a region that shares homology with the region of random sequence of the particular RNA molecule. In another embodiment, the homology-sharing region of the altered version of the particular RNA molecule is double stranded. In another embodiment, the homology-sharing region is single stranded. Each possibility represents another embodiment of the present invention.

In another embodiment, the ds regions of the particular RNA molecule and the altered version of same share at least 70% homology. In another embodiment, the 2 regions share at least 75% homology. In another embodiment, the 2 regions share at least 80% homology. In another embodiment, the 2 regions share at least 85% homology. In another embodiment, the 2 regions share at least 90% homology. In another embodiment, the 2 regions share at least 95% homology. In another embodiment, the 2 regions share at least 97% homology. In another embodiment, the altered version of the particular RNA molecule comprises a ds region that is identical with the ds region of the particular RNA molecule. In another embodiment, the second expression vector backbone is different from the expression vector backbone utilized in the first round of screening. Each possibility represents a separate embodiment of the present invention.

In another embodiment, as exemplified herein in Example 17, a method of the present invention further comprises the steps of a. isolating or amplifying a particular expression vector found to have biological activity, its insert, or a fragment thereof (the "first round of selection"); b. mutagenizing a fragment of the particular expression vector, wherein the fragment comprises a region encoding the double-stranded region of random sequence contained in the expression vector, thereby generating a sub-library of nucleotide molecules, the nucleotide molecules comprising variants of the region of random sequence; c. inserting or subcloning the sub-library into an expression vector backbone, thereby generating a sub-library of expression vectors; d. contacting a second cell population with the sub-library of expression vectors (the "second round of selection"), wherein the sub-library of expression vectors, or a fraction thereof, is taken up by the second cell population; and e. determining or measuring the biological parameter of interest or a readout thereof in the second cell population. In this embodiment, if the biological parameter of interest or readout thereof is further altered in a particular cell in the second cell population, then the particular cell carries an improved expression vector. In another embodiment of this method, some of the RNA molecules in the sub-library contain one or more mismatches between the 2 complementary strands of the region of random sequence. Each possibility represents a separate embodiment of the present invention.

In another embodiment, the step of mutagenizing comprises the step of copying a fragment of the particular expression vector by a low-fidelity method. In another embodiment, the mutagenized sequences are generated by a computer. Each possibility represents a separate embodiment of the present invention.

In another embodiment, the mutagenesis is performed using a computational method. In another embodiment, the computational method comprises generating each possible single mutation of the RNAi molecule identified. In another embodiment, double mutations are also generated. In another embodiment, triple mutations are also generated. Each possibility represents a separate embodiment of the present invention.

In another embodiment, wherein a mutation is introduced into a residue in the ds portion of the RNAi, a corresponding mutation is introduced in the complementary residue, to maintain base pairing. In another embodiment, a corresponding mutation is not introduced. Each possibility represents a separate embodiment of the present invention.

In another embodiment, the entire sequence encoding the RNA molecule is mutagenized. In another embodiment, both strands of the double-stranded region are mutagenized. In another embodiment, 1 strand (a "half-book") of the double-stranded region is mutagenized. In another embodiment, a portion of 1 strand of the double-stranded region is mutagenized. Each possibility represents a separate embodiment of the present invention.

In another embodiment, a method of the present invention further comprises the step of identifying 1 or more putative target mRNAs of an RNAi molecule with biological activity, and creating a sub-library of sequences predicted to bind more strongly to the targets. In another embodiment, the sub-library comprises sequences predicted to bind more strongly to 1 of the predicted targets. In another embodiment, the sub-library comprises sequences predicted to bind more strongly to a subset of the predicted targets. In another embodiment, the sub-library comprises sequences predicted to bind more strongly to most of the predicted targets. In another embodiment, the sub-library comprises sequences predicted to exhibit greater preferential binding to 1 or a subset of the predicted targets, relative to a different subset of the predicted targets. In another embodiment, binding of RNAi molecules in the sub-library to targets is tested directly in an in vitro RNAi assay, using a method known in the art. Each possibility represents a separate embodiment of the present invention.

Methods for putative target mRNAs of an RNAi molecule are well known in the art, and include, in another embodiment, a computer program. In another embodiment, the program is miRanda (Enright A J, John B, Gaul U, Tuschl T, Sander C, Marks D S. MicroRNA targets in *Drosophila*. Genome Biol 2003; 5(1):R1). In another embodiment, the program is miRGen (M. Megraw, P. Sethupathy, B. Corda, and A. G. Hatzigeorgiou (2006). Nucleic Acids Res, 35: D149-D155). In another embodiment, the program is TargetScan (Lewis B P, Burge C B, Bartel D P. Cell, 120:15-16 (2005). In another embodiment, the program is MiRscan (Lim, L P, Lau, N C, Weinstein, E, Abdelhakim, A, Yekta, S, Rhoades, M W, Burge, C B and Bartel, D P (2003). The microRNAs of *Caenorhabditis elegans*. Genes & Dev. 17, 991). In another embodiment, the program is PicTar (Krek et al, Nature Genetics 37:495-500 (2005)). In another embodiment, the program is MicroInspector (Rusinov V, Baev V, Minkov I N, Tabler M. Nucleic Acids Res 2005; 33: W696-700). In another embodiment, the computer program is any another suitable computer program known in the art. Each possibility represents a separate embodiment of the present invention.

In another embodiment, a method of present invention further comprises contacting an additional cell or cell population with a particular expression vector found to exhibit biological activity in the above method and determining or measuring the biological parameter of interest or readout thereof in the additional cell, whereby, if the biological parameter of interest or readout thereof is altered in the additional cell, then the efficacy of the RNA molecule encoded by the expression vector is confirmed. In another embodiment, the insert sequences are isolated from the cell population. In another embodiment, a fragment comprising the coding sequence for the RNA molecule found to exhibit biological activity in the first round of selection is excised or amplified from the expression vector, or synthesized de novo after sequencing, subcloned into the same expression vector or a different expression vector, then used to contact an additional cell(s), for which the biological parameter of interest or readout thereof is determined or measured. Each possibility represents a separate embodiment of the present invention.

Methods for (1) modifying an RNA molecule containing a double-stranded region, and for (2) expressing an RNA molecule containing a double-stranded region in various types of vectors, are well known in the art, and are described, for example, in Palliser D et al (An siRNA-based microbicide protects mice from lethal herpes simplex virus 2 infection. Nature. 2006 Jan. 5; 439(7072):89-94). Each method represents a separate embodiment of the present invention.

In another embodiment, one or more additional rounds of enrichment are performed after the second round. In another embodiment, the use of 2 or more rounds of enrichment increases the fraction of true positive clones. In another embodiment, the use of multiple rounds of enrichment increases the fraction of true positive clones. Each possibility represents a separate embodiment of the present invention.

In another embodiment, the expression vector used in the first round of selection is an integrating vector. In another embodiment, an integrating vector facilitates identification of true positives because of the irreversible nature of its effects.

In another embodiment, the different expression vector used in the second or a subsequent round of selection produces a different form of the RNA molecule (in other embodiments, RNAi, siRNA, microRNA, or shRNA) identified in the first round of selection (having essentially the same double-stranded region of random sequence), after which the different form of the RNA molecule itself (in another embodiment, an siRNA) is brought into contact with an additional cell(s), for which the biological parameter of interest or readout thereof is determined or measured. In another embodiment, contacting the additional cell(s) with the RNA molecule itself facilitates observation of the phenotype conferred by the RNA molecule in a majority (in another embodiment, in a high percentage) of the target cells. In another embodiment, the phenotype is observed in over 60% of the cells in the second or subsequent round of enrichment. In another embodiment, the phenotype is observed in over 70% of the cells. In another embodiment, the phenotype is observed in over 80% of the cells. In another embodiment, the phenotype is observed in over 90% of the cells. In another embodiment, the phenotype is observed in over 95% of the cells. In another embodiment, the phenotype is observed in over 97% of the cells. In another embodiment, the phenotype is observed in over 99% of the cells. Each possibility represents a separate embodiment of the present invention.

In another embodiment, the different form of the RNA molecule used in the second or a subsequent round of selection exerts its effects in a reversible manner. In another embodiment, use of a reversible form of inhibitory RNA in a method of the present invention enables further experimental study of the effects of the RNA molecule (in other embodiments, a temporal study of its effects, or an observation of reversing or halting its effects by removing the RNA molecule). In another embodiment, an expression vector with an inducible or repressible promoter is used as an alternative to a reversible form of RNAi. Each possibility represents a separate embodiment of the present invention.

In another embodiment, as exemplified herein in Example 17, only the first half of the region encoding the double-stranded region of random sequence (i.e. the region encoding one strand of the double-stranded region of random sequence; or "half-book") is placed between the first and second constant regions used for the original single-stranded DNA template and copied by a low-fidelity method, thereby generating a sub-library of half books that is used to create an shRNA-expressing sub-library by the one of the methods described herein. Then the sub-library is tested for a biological parameter by a method of the present invention.

In another embodiment, one of the above methods of mutagenesis and/or low-fidelity copying is practiced without the preceding steps described in one of the above methods of generating a library. In this embodiment, the above method represents a separate embodiment of the present invention.

In another embodiment, the improved expression vector encodes an improved RNA molecule that affects the biological parameter of interest more than the particular RNA molecule originally identified. In another embodiment, the improved expression vector exhibits greater tissue specificity than the originally identified RNA molecule. In another embodiment, a lower dosage is required of the improved expression vector or the corresponding RNA molecule encoded thereby, than the originally identified RNA molecule. In another embodiment, the improved expression vector exhibits any other improved property known in the art, relative to the originally identified RNA molecule. Each possibility represents a separate embodiment of the present invention.

In another embodiment of methods and compositions of the present invention, an improved expression vector identified by the above method, its insert, or a fragment thereof is isolated or amplified. In another embodiment, either the improved expression vector is sequenced or a fragment thereof is sequenced, wherein the fragment comprises the coding sequence for the improved RNA molecule. In another embodiment, an additional cell is contacted with the improved expression vector its encoded RNA, or another type of RNA molecule having the same or a homologous double-stranded region, and the biological parameter of interest or readout thereof is determined or measured in the additional cell. Each possibility represents a separate embodiment of the present invention.

The method of low-fidelity copying utilized in methods of the present invention is, in another embodiment, random mutagenesis by PCR (e.g. error-prone PCR). In another embodiment, the method is mutagenesis with degenerate oligonucleotides. In another embodiment, the method is linker-scanning mutagenesis. In another embodiment, the method is any other mutagenesis method known in the art. Each possibility represents a separate embodiment of the present invention.

In another embodiment, as exemplified herein in Example 18, the present invention provides a method of identifying a drug target for a disease or disorder of interest, comprising the steps of (a) identifying an RNA molecule that affects a biological parameter of interest by a method of the present invention, wherein the biological parameter of interest is altered in the disease or disorder of interest; and (b) identifying a cellular RNA molecule whose expression is altered by the RNA molecule, whereby the cellular RNA molecule is identified as a drug target for the disease or disorder of interest.

In another embodiment, as exemplified herein in Example 17, the present invention provides a method of identifying a variant of an RNA molecule that affects a biological parameter of interest, wherein the variant has an altered ability to affect the biological parameter of interest, comprising the steps of:
a. copying a nucleic acid molecule encoding the RNA molecule by a low-fidelity method, thereby generating a sub-library of nucleotide molecules, the nucleotide molecules comprising variants of the RNA molecule;
b. subcloning the sub-library into an expression vector backbone, thereby generating a sub-library of expression vectors;
c. contacting a cell population with the sub-library of expression vectors, wherein the sub-library of expression vectors, or a fraction thereof, is taken up by the cell population; and
d. determining or measuring the biological parameter of interest or a readout thereof in the cell population.

By this method, in another embodiment, if a cell in the cell population exhibits an alteration of the biological parameter of interest or readout thereof, then the cell carries a particular expression vector that encodes a particular variant of the RNA molecule that has an altered ability to affect the biological parameter of interest. In another embodiment, the 2 strands of the double-stranded region in the variant are complementary to one another. In another embodiment, the 2 strands contain one or more mismatches relative to one another. Each possibility represents a separate embodiment of the present invention.

In another embodiment, the present invention provides an altered RNA molecule that has an ability to affect a biological parameter of interest, wherein the altered RNA molecule is identified by the method of the present invention.

In another embodiment of methods of the present invention, the altered ability to affect a biological parameter of interest is altered relative to the original RNA molecule.

"Altered" refers, in one embodiment, to an increased potency. In another embodiment, the term refers to a decreased potency. In another embodiment, the term refers to an increased tissue specificity. In another embodiment, the variant exhibits an increased biological half-life. In another embodiment, the variant exhibits a decreased biological half-life. In another embodiment, the variant exhibits an increased bioavailability. In another embodiment, the variant is altered, relative to the initial RNA molecule, in any other biological or therapeutic parameter of interest. Each possibility represents another embodiment of the present invention.

In another embodiment, a library of RNA molecules comprising a double-stranded region of random sequence, not inserted into an expression vector backbone, is generated by a method of the present invention. In another embodiment, all the embodiments enumerated herein for generating a set of recombinant expression vectors apply to this method, where appropriate. The library is then used, in another embodiment, to screen for RNA molecules. In another embodiment, the present invention provides a library of RNA molecules generated by this method. Each possibility represents a separate embodiment of the present invention.

In another embodiment, the present invention provides an expression vector for an RNA molecule comprising a double-stranded region of random sequence, wherein the expression vector is generated by a method of the present invention.

In another embodiment, the present invention provides an expression vector for an RNA molecule comprising a double-stranded region of random sequence, wherein the expression vector is identified by a method of the present invention.

In another embodiment, the present invention provides an RNA molecule that is encoded by an expression vector of the present invention.

In another embodiment, the present invention provides an RNA molecule that is produced by an expression vector of the present invention.

In another embodiment, the present invention provides an RNA molecule comprising a double-stranded region of random sequence, wherein the RNA molecule is identified by a method of the present invention.

In another embodiment, the present invention provides a method of conferring upon a cell a protection against a viral infection, comprising contacting the cell with an expression vector or RNA molecule of the present invention, thereby conferring upon a cell a protection against a viral infection.

In another embodiment, the present invention provides a method of inhibiting or impeding an ability of a virus to replicate in a subject, comprising contacting the subject with an expression vector or RNA molecule of the present invention, thereby inhibiting or impeding an ability of a virus to replicate in a subject. In another embodiment, the present invention provides a method of inhibiting or impeding viral entry into a cell, comprising contacting the cell with an expression vector or RNA molecule of the present invention. In another embodiment, the expression vector or RNA molecule down-regulates a viral receptor(s) in the cell. In another embodiment, the expression vector or RNA molecule down-regulates a protein required for viral replication. Each possibility represents a separate embodiment of the present invention.

In another embodiment, the present invention provides a method of inducing a differentiation of a cell into a cell type of interest, comprising contacting the cell with an expression vector or RNA molecule of the present invention, thereby inducing a differentiation of a cell into a cell type of interest.

"Differentiation of a cell into a cell type of interest" refers, in another embodiment, to a full differentiation. In another embodiment, the term refers to a partial differentiation. "Cell type of interest" refers, in another embodiment, to a cell type that is required for a therapeutic or research application. In another embodiment, the term refers to an intermediate, or partially differentiated cell type that is a precursor to the cell type required for a therapeutic or research application. Each possibility represents a separate embodiment of the present invention.

In another embodiment, the present invention provides a method of inducing a long-term proliferation of a cell, comprising contacting the cell with an expression vector or RNA molecule of the present invention, thereby inducing a long-term proliferation of a cell. In another embodiment, the present invention provides a method of sustaining a pluripotency of a cell, comprising contacting the cell with an expression vector or RNA molecule of the present invention, thereby sustaining a pluripotency of a cell.

Each therapeutic or prophylactic method represents a separate embodiment of the present invention.

In another embodiment, a method of the present invention utilizes a particular recombinant expression vector or an RNA molecule encoded thereby, wherein the particular recombinant expression vector has been selected by a method of the present invention. Each possibility represents a separate embodiment of the present invention.

In another embodiment, the present invention provides a set or library of expression vectors, wherein the expression vectors generate RNA molecules comprising a double-stranded region of random sequence, and wherein the set or library of expression vectors is generated by a method of the present invention.

In another embodiment, the present invention provides a set or library of recombinant viruses, wherein the recombinant viruses generate RNA molecules comprising a double-stranded region of random sequence, and wherein the set or library of recombinant viruses is generated by a method of the present invention.

In another embodiment, the present invention provides an expression vector for an RNA molecule comprising a double-stranded region of random sequence, wherein the RNA molecule has an ability to affect a biological parameter of interest, and wherein the expression vector is identified by a method of the present invention.

In another embodiment, a method of the present invention utilizes an improved vector identified by a second screening, following generating copies of an insert of a vector or a fragment of the insert by a low-fidelity improvement method, as described herein.

The particular restriction enzymes, restriction sites, vectors, etc. utilized in the Examples herein are merely exemplary embodiments of the present invention. Any suitable restriction enzyme, restriction site, vector, etc. can be utilized in accordance with the methods disclosed herein. Each enzyme, restriction site, vector, etc. represents a separate embodiment of the present invention.

In another embodiment of methods of the present invention, the second and/or third recognition site described above is not derived entirely from the sequence from the first single-stranded DNA molecule, but rather takes all or part of its sequence from the hairpin-shaped DNA molecule.

In another embodiment, the present invention provides a method of generating an RNA molecule comprising a double-stranded region of random sequence, the method comprising the steps of:

a. obtaining a first single-stranded DNA molecule, wherein the first single-stranded DNA molecule comprises, in 5' to 3' order,
  (i) a first constant region, wherein the first constant region comprises a first recognition site, which, when in double-stranded form, is a substrate for a first restriction enzyme, wherein the first constant region ends in one or more adenines;
  (ii) a region of random sequence; and
  (iii) a second constant region, wherein the second constant region comprises a second recognition site, which, when in double-stranded form, is a substrate for a second restriction enzyme;
b. annealing a first primer to the second constant region, wherein
  (i) the first primer contains mismatch(es) with respect to the second constant region;
  (ii) the first primer, when in double-stranded form, is not a substrate for the second restriction enzyme;
  (iii) the first primer, when in double-stranded form, is a substrate for a third restriction enzyme; and
  (iv) the second constant region, when in double-stranded form, is not a substrate for the third restriction enzyme;
c. extending the first primer, thereby generating a double-stranded intermediate I B, comprising the first single-stranded DNA molecule and a second single-stranded DNA molecule, wherein the second single-stranded DNA molecule comprises a reverse complement of the region of random sequence and the first constant region;
d. ligating a hairpin-shaped DNA molecule to the 3' end of the first single stranded DNA molecule and the 5' end of the second single-stranded DNA molecule, thereby converting the double-stranded intermediate I B into a hairpin-shaped intermediate II;
e. annealing a second primer to the reverse complement of the first constant region, wherein:
  (i) the second primer contains mismatches with respect to the reverse complement of the first constant region; and
  (ii) the second primer, when in double-stranded form, is not a substrate for the first restriction enzyme;
f. extending the second primer, thereby generating a double-stranded intermediate III, comprising the hairpin-shaped intermediate II and a third single-stranded DNA molecule;
g. digesting the double-stranded intermediate III with the first restriction enzyme, thereby generating a double-stranded intermediate IV, whereby the double-stranded intermediate IV does not comprise the one or more adenines on its strand that corresponds to the first single-stranded DNA molecule;
h. ligating the double-stranded intermediate IV into a linearized vector backbone, wherein the linearized vector backbone comprises an RNA polymerase promoter, thereby generating a circular intermediate V;
i. digesting the circular intermediate V with the second restriction enzyme and the third restriction enzyme, thereby generating a linear intermediate VI; and
j. intra-molecularly ligating the linear intermediate VI, thereby generating an expression vector for an RNA molecule comprising a double-stranded region of random sequence.

Figure 3:
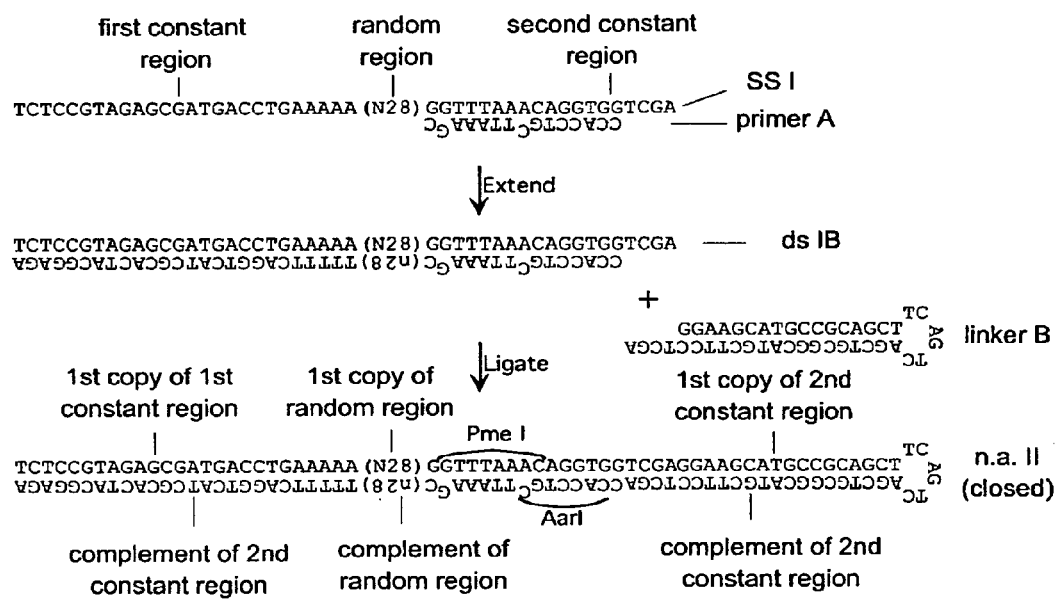
FIG. 3. Additional approach for creation of a library of expression vectors for partially self-complementary RNA molecules, part I. Described in Example 4. Sequences of 10 or more nt and not previously assigned a SEQ ID No are listed as SEQ ID No: 13-17.
Figure 5:
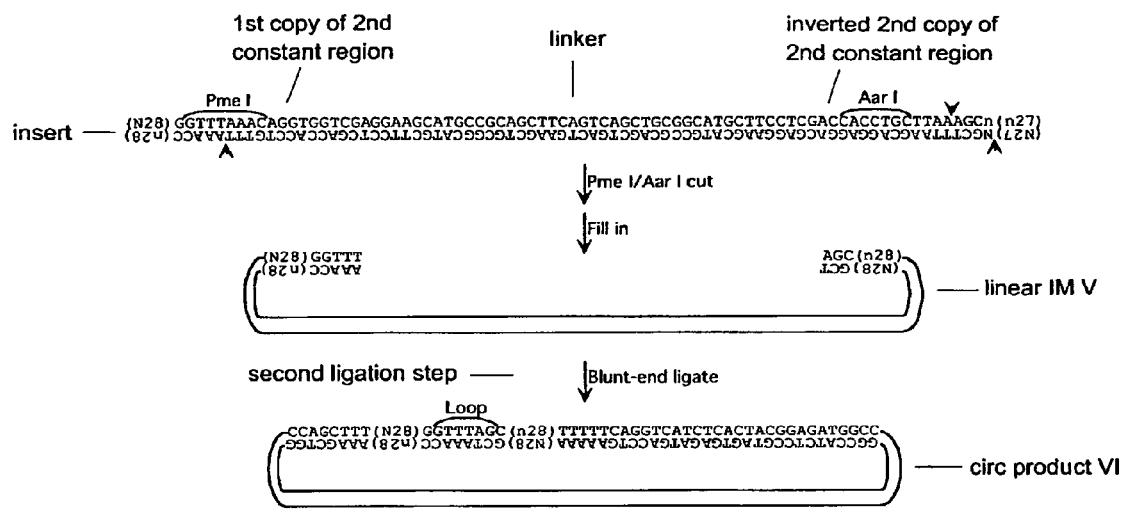
FIG. 5. Additional approach for creation of a library of partially self-complementary RNA molecules, part II- creation of the non-complementary loop sequence. Described in Example 4. Sequences of 10 or more nt and not previously assigned a SEQ ID No are listed as SEQ ID No: 28-33.

In another embodiment, the above method is performed as depicted in FIGS. 3-5.

In another embodiment, the RNA molecule expressed by a vector of the present invention is self-complementary along part of its length. In another embodiment, the RNA molecule is self-complementary along its entire length. Each possibility represents another embodiment of the present invention.

"Self-complementary along part of its length" refers, in another embodiment, to an RNA molecule with a region that hybridizes to another region of the molecule. In another embodiment, the region is perfectly complementary to the other region of the molecule. In another embodiment, the first region has a mismatch with respect to the other region. In another embodiment, the first region has more than one mismatch with respect to the other region. In another embodiment, the first region has a deletion with respect to the other region. In another embodiment, the deletion causes an internal loop that is recognized by a cellular enzyme. In another embodiment, the first region has an overhang or sticky end with respect to the other region. In another embodiment, the first region and other (complementary) region are separated by a non-complementary linker or intervening region. In another embodiment, the non-complementary linker region forms a loop structure. Each possibility represents a separate embodiment of the present invention.

"Self-complementary along its entire length" refers, in another embodiment, to a double-stranded RNA molecule lacking an overhang or linker/intervening region. In another embodiment, the double-stranded RNA molecule is perfectly self-complementary. In another embodiment, the double-stranded RNA molecule has a mismatch. In another embodiment, the double-stranded RNA molecule has more than one mismatch. Each possibility represents a separate embodiment of the present invention.

Partially self-complementary RNA molecules of the present invention comprise, in another embodiment, a self-complementary region ("stem") with an intervening loop-forming region ("loop"), as depicted at the bottom of FIG. 1.

In another embodiment, the intervening sequence of partially self-complementary RNA molecules of the present invention forms a loop structure when the random sequence and the complementary sequence are annealed to one another. In another embodiment of methods of present invention, the loop-forming region is not palindromic. In another embodiment, the loop-forming region is not self-complementary. Each possibility represents a separate embodiment of the present invention.

In another embodiment, the RNA molecule expressed by a vector of the present invention is a short hairpin RNA (shRNA). In another embodiment, the RNA molecule is a small inhibitory RNA (siRNA). In another embodiment, the RNA molecule is an inhibitory RNA (RNAi). In another embodiment, the RNA molecule is an agRNA (antigenic RNA). "agRNA" refers, in another embodiment, to a double stranded RNA capable of interacting with mRNA and silencing gene transcription. In another embodiment, the RNA molecule is a microRNA (miRNA). In another embodiment, the RNA molecule is an anti-sense locked-nucleic acid (LNA) oligonucleotide. In another embodiment, the RNA molecule is any type of inhibitory RNA enumerated or described in Banan M et al (The ins and outs of RNAi in mammalian cells. Curr Pharm Biotechnol. 2004 October; 5(5):441-50. In another embodiment, the RNA molecule is any type of RNAi known in the art. Each possibility represents a separate embodiment of the present invention.

In another embodiment, the first residue of the second constant region of ss intermediate I determines the identity of the complementary nucleotide pair flanking the loop sequence in a ds RNA produced by a recombinant expression vector of the present invention. In another embodiment, a method of the present invention is repeated with 4 sets of first single-stranded DNA molecule, wherein the second constant region begins with 4 different nucleotides in the four groups. In another embodiment, the 4 pools are combined to generate a library wherein every residue of the "stem" is randomized. Each possibility represents a separate embodiment of the present invention.

In another embodiment of methods of the present invention, the mismatched residue in the primer (or, if more than one, the mismatch closest to the 3' end) is 1 nucleotide (nt) away from the 3' end of the primer. In another embodiment, the distance is 2 nt or less. In another embodiment, the distance is 3 nt or less. In another embodiment, the distance is 4 nt or less. In another embodiment, minimizing this distance reduces the amount of sequence in the stem of the RNA molecules that is derived from the primer (and that, is therefore constant). Each possibility represents a separate embodiment of the present invention.

"Expression vector" refers, in another embodiment, to a means of expressing an RNA molecule of the present invention. In another embodiment, the expression vector is a plasmid. In another embodiment, the vector is a recombinant viral vector. In another embodiment, the vector is a recombinant bacterial vector. In another embodiment, the vector is a naked DNA vector. In another embodiment, the vector is a self-replicating nucleic molecule, or virus comprising same, that is capable of expressing the RNA molecule of the present invention. In another embodiment, the vector is any other vector known in the art. Each possibility represents a separate embodiment of the present invention.

Methods for constructing and utilizing recombinant vectors are well known in the art and are described, for example, in Sambrook et al. (2001, Molecular Cloning: A Laboratory Manual, Cold Spring Harbor Laboratory, New York), and in Brent et al. (2003, Current Protocols in Molecular Biology, John Wiley & Sons, New York).

In another embodiment of methods of present invention, the expression vector of methods and compositions of the present invention is a recombinant virus. In another embodiment of methods of present invention, the expression vector, or a copy thereof, is capable of being packaged as a recombinant virus. In another embodiment, a recombinant RNA molecule of the present invention is capable of being packaged in a recombinant virus. In another embodiment, the packaging utilizes a packaging cell line. In another embodiment, a library of expression vectors, encoding RNA molecules that contain a number of regions of random sequence, is generated by a method of the present invention or a method that comprises a method of the present invention. In another embodiment, the library is in retrovirus form (e.g. in the form of RNA that is reverse-transcribed upon transduction to generate the DNA form of the vector). Each possibility represents a separate embodiment of the present invention.

In another embodiment of methods of present invention, the expression vectors integrate into the genome of cells in the cell population used to test and/or identify the vectors. In another embodiment, the expression vectors integrate into the genome of the target cells (e.g. for a therapeutic utility). In another embodiment, the expression vectors are carried in cells in the cell population episomally. In another embodiment, the expression vectors are carried in cells in the cell population as extra-chromosomal vectors. In another embodiment, a drug resistance gene is used to select for cells that retain an expression vector. Each possibility represents a separate embodiment of the present invention.

In another embodiment of methods of the present invention, as exemplified herein in Examples 1-2, the expression vector utilized in methods of the present invention further comprises a gene encoding a marker protein; e.g. enhanced green fluorescent protein (eGFP) or enhanced farnesylated green fluorescent protein (eGFPf). In another embodiment, a marker protein is used to detect transfected or transduced cells in subsequent steps (e.g. library screening or selection methods).

In another embodiment, the expression vector further comprises a gene encoding a protein that confers a phenotype of interest. In another embodiment, the gene confers a disease phenotype. In another embodiment, the expression vector is used to identify therapeutic RNA molecules that ameliorate, alleviate, or treat the disease or disease phenotype. Each possibility represents a separate embodiment of the present invention.

In another embodiment of methods of the present invention, the expression vector further comprises a gene encoding an inhibitory RNA molecule (in another embodiment, a short-interfering (siRNA) molecule) of known function. In another embodiment, the inhibitory RNA molecule of known function is used to confer a phenotype (in another embodiment, a phenotype of a disease of interest) on the cells that are being screened with a library. In another embodiment, an siRNA molecule added exogenously is used to confer the phenotype. In another embodiment, the library is used to identify RNA molecules that treat the phenotype or disease of interest conferred by the inhibitory RNA molecule of known function. Each possibility represents a separate embodiment of the present invention.

In another embodiment, the 2 RNAi molecules (the RNAi of known function and the RNA molecule containing a double-stranded region of random sequence) are encoded by 2 H1-promoter cassettes. In another embodiment, the 2 H1-promoter cassettes can be independently subcloned into the vector. In another embodiment, one of the 2 H1-promoter cassettes comprises a double-stranded region of random sequence. In another embodiment, the cassette that comprises a double-stranded region of random sequence is generating using one of the methods described above. In another embodiment, the 2 RNAi molecules are expressed using any other method known in the art. Each possibility represents a separate embodiment of the present invention.

Each type of expression vectors represents a separate embodiment of the present invention.

In another embodiment of methods of the present invention, asymmetric digestion of a circular intermediate results in unequal portions of the first and second copies of the second constant region on the 2 ends of a linear intermediate generated thereby. In another embodiment, the unequal portions enable the loop sequence to be non-self-complementary. Each possibility represents a separate embodiment of the present invention.

In another embodiment of methods of the present invention, the promoter of an RNA polymerase present in the linearized vector backbone is an RNA pol III promoter. In another embodiment, the promoter is an HI promoter. In another embodiment, the promoter is a U6 promoter. In another embodiment, the promoter is a promoter that is suitable for shRNA expression. In another embodiment, the promoter is a promoter for any other RNA pol known in the art. Each possibility represents a separate embodiment of the present invention.

In another embodiment of methods of the present invention, the promoter in the expression vector is 25 nt upstream of the beginning of the region of random sequence in the expression plasmid. In another embodiment, one or more consecutive pyrimidines (e.g. 4) immediately precedes the transcription start site in the expression plasmid. In another embodiment, the string consists of 2 pyrimidines. In another embodiment, the string consists of 4 pyrimidines. In another embodiment, the string consists of 3 pyrimidines. In another embodiment, the string consists of 5 pyrimidines. In another embodiment, the string consists of a different number of pyrimidines. Each possibility represents a separate embodiment of the present invention.

In another embodiment, a method of present invention further comprises contacting the expression vector or set or library of expression vectors with an RNA polymerase, thereby generating the RNA molecule or library thereof. In another embodiment, the step of contacting is performed in the presence of ribonucleotide precursors. Each possibility represents a separate embodiment of the present invention.

In another embodiment, a method of present invention further comprises performing multiple times, with a set of random sequences, a method of generating an expression vector for an RNA molecule of the present invention, thereby generating a set or library of the expression vectors. In another embodiment, a method of present invention further comprises packaging the set or library of expression vectors as a set or library of recombinant viruses. In another embodiment, the set or library of expression vectors is a set or library of recombinant viruses. Each possibility represents a separate embodiment of the present invention.

In another embodiment, the recombinant viruses used to package the set or library of expression vectors are recombinant retroviruses. In another embodiment, the recombinant viruses are recombinant lentiviruses. In another embodiment, the recombinant viruses are recombinant adenoviruses. In another embodiment, the recombinant viruses are derived from a vector enumerated or described in Wadhwa R et al (Vectors for RNA interference. Curr Opin Mol. Ther. 2004 August; 6(4):367-72). In another embodiment, the recombinant viruses comprise a backbone of a vector enumerated or described in Wadhwa R et al. In another embodiment, the recombinant viruses are derived from any other type of virus known in the art that has the ability to infect or transduce a eukaryotic cell. Each possibility represents a separate embodiment of the present invention.

In another embodiment, the biological parameter of interest or readout thereof is a derivation of a cell type with repopulating capacity from a stem cell. In another embodiment, the cell type that is derived from the stem cell is a hematopoietic stem cell. In another embodiment, the cell type that is derived from the stem cell exhibits long-term repopulating capacity. In another embodiment, the cell type that is derived is any other cell type known in the art with repopulating capacity. Each possibility represents a separate embodiment of the present invention.

In another embodiment, the biological parameter of interest or readout thereof is ability of a cell (either the cell used in the assay or a biologically relevant target cell) to survive under a defined set of adverse conditions. In another embodiment, the biological parameter of interest or readout thereof is ability of the cell to maintain growth under a defined set of conditions. In another embodiment, the conditions are not lethal to wild-type cells, but are lethal to cells that are a disease model (e.g. cells comprising a mutation or cells in which expression of a protein or enzyme has been repressed—e.g. by inhibitory RNA).

In another embodiment, the biological parameter of interest or readout thereof is susceptibility of a cell (either the cell used in the assay or a biologically relevant target cell) to a pathogen, toxin or toxic insult. In another embodiment, the toxin or toxic insult is an oxidant. In another embodiment, the toxin or toxic insult is a stress. In another embodiment, the biological parameter of interest or readout thereof is survival of the cell despite the presence of a pathogen. In another embodiment, the biological parameter of interest or readout thereof is ability of a pathogen to replicate in the cell. In another embodiment, the pathogen is an intracellular pathogen. In another embodiment, the intracellular pathogen is a virus. In another embodiment, the intracellular pathogen is an intracellular bacterium. In another embodiment, the intracellular pathogen is any other type of intracellular pathogen known in the art. Each possibility represents a separate embodiment of the present invention In another embodiment, the biological parameter of interest or readout thereof is ability to kill a cancer cell (either the cell used in the assay or a biologically relevant target cell). In another embodiment, the biological parameter of interest or readout thereof is ability to sensitize the cancer cell to a pro-apoptotic or pro-necrotic stimulus. Each possibility represents a separate embodiment of the present invention.

In another embodiment, the biological parameter of interest or readout thereof is an expression or expression level of a protein of interest. In another embodiment, the biological parameter of interest or readout thereof is an expression or expression level of an mRNA of interest.

In another embodiment, the RNA molecule that affects susceptibility to a pathogen or replication of the pathogen hybridizes with nucleic acids specific to the pathogen. In another embodiment, the RNA molecule hybridizes with cellular nucleic acids utilized by the pathogen. In another embodiment, the RNA molecule upregulates cellular defense mechanisms. In another embodiment, the RNA molecule functions via another mechanism. In another embodiment, the RNA molecule functions via an unknown mechanism. Each possibility represents a separate embodiment of the present invention.

In another embodiment, the biological parameter of interest or readout thereof is a differentiation of the cell into a cell type of interest. In another embodiment, the biological parameter of interest or readout thereof is maintenance of a cell or cell type in an undifferentiated state. In another embodiment, the biological parameter of interest or readout thereof is ability to induce long-term proliferation or sustain pluripotency of the cell. In another embodiment, the biological parameter of interest or readout thereof is maintenance of a stem cell in an undifferentiated state.

The cell type of interest is, in other embodiments, a heart muscle cell, neuron, skeletal muscle cell, hepatocyte, skin cell, renal tubule epithelial cell, pancreatic islet cell, glomerular cell, endothelial cell, osteocyte, chondrocyte, B or T lymphocyte, neutrophil, basophil, eosinophil, monocyte, red blood cell, dendritic cell, thyroid cell, adrenal cell, megakaryocyte. In another embodiment, the cell type of interest is any other cell damaged in a disease or disorder. Each possibility represents a separate embodiment of the present invention.

In another embodiment, "biological parameter" refers to any measurable or observable phenotype of a cell, e.g. a morphological characteristic, differentiation state, growth rate, cell cycle characteristic, biochemical characteristic, or another phenotype. Each possibility represents a separate embodiment of the present invention.

In another embodiment, the biological parameter of interest or readout thereof is any other biological parameter known in the art. Each biological parameter represents a separate embodiment of the present invention.

The cell that is the target of methods of the present invention is, in one embodiment, a stem cell. In another embodiment, the cell is an embryonic stem cell. In another embodiment, the cell is any other type of stem cell known in the art. In another embodiment, the cell is a partially differentiated cell type. In another embodiment, the cell is a precursor of a cell type of interest. In another embodiment, the cell is a model for a disease phenotype. In another embodiment, the cell is an adult stem cell. In another embodiment, the cell is a tissue-specific stem cell. In another embodiment, the cell is a cell type that is susceptible to viral infection. In another embodiment, the cell is any other cell type known in the art. Each possibility represents a separate embodiment of the present invention.

In another embodiment, an RNA molecule of the present invention is used to convert one cell type into another.

In another embodiment, differentiation into the cell type of interested is determined morphologically. In another embodiment, differentiation is determined by measuring or assaying expression of one or more marker proteins. In another embodiment, the marker protein(s) are tissue-specific surface marker proteins.

Methods for determining an expression of a protein of interest are well known in the art, and include, for example, Western blot and fluorescence-activated cell sorting (FACS). Methods for determining an expression of an mRNA of interest are well known in the art, and include, for example, Northern blot. Each possibility represents a separate embodiment of the present invention.

"Readout" refers to, in another embodiment, any means known in the art of determining, assessing, measuring, or observing a biological phenotype. In another embodiment, the term includes biochemical assays, morphological observation, cell staining, cell sorting, and the like. In another embodiment, the readout is survival under a defined set of conditions. Each possibility represents a separate embodiment of the present invention.

In another embodiment, a subset or plurality of cells exhibits the alteration in the biological parameter of interest or readout thereof that is measured. In another embodiment, multiple cells exhibit the alteration in the biological parameter of interest or readout thereof that is measured. In another embodiment, the cells contain more than one particular expression vector. In another embodiment, the particular expression vectors contained in the cells, biological activity, their inserts, or fragments thereof are each isolated and/or sequenced, thus identifying more than one RNA molecule that affects the biological parameter of interest or readout thereof.

In another embodiment, a method of the present invention further comprises isolating or amplifying the particular expression vector that mediates the alteration in the biological parameter of interest. In another embodiment, the insert of the particular expression vector is isolated or amplified. In another embodiment, a fragment of the particular expression vector is isolated or amplified. In another embodiment, the expression vector, insert, or fragment is amplified by PCR. In another embodiment, a method of present invention further comprises sequencing the particular expression vector that is isolated or amplified, its insert, or a fragment thereof. In another embodiment, the fragment comprises the coding sequence for the RNA molecule identified to have biological activity (e.g. the RNA molecule that affects the biological parameter of interest). Each possibility represents a separate embodiment of the present invention.

In another embodiment, the step of sequencing comprises amplifying the coding sequence for the RNA molecule with biological activity by PCR. In another embodiment, the PCR utilizes primers from sequences in the vector that flank the coding sequence for the RNA molecule of the present invention. In another embodiment, PCR can be performed on either an integrated- or non-integrated vector. Each possibility represents another embodiment of the present invention.

In another embodiment of methods of the present invention, after sequencing the PCR product, the ends of an aliquot of the product are digested in a PCR tube, subcloned back into the parent vector, and the shRNA construct, or a corresponding RNAi molecule with the same or a homologous double-stranded region, or a construct encoding the corresponding RNAi molecule, (and the control shRNAs) is re-added to the test cells. In this confirmatory testing, populations of cells are compared, rather than small numbers of individual survivors. This method, in another embodiment, reduces the unlikely occurrence of false positives in screening or selection methods of the present invention.

In another embodiment, a restriction enzyme utilized in a method of the present invention cuts its substrate outside of its recognition sequence. In another embodiment, the cut is at least 1 nt away from the end of the recognition sequence. In another embodiment, the distance is at least 2 nt away. In another embodiment, the distance is at least 3 nt away. In another embodiment, the distance is at least 4 nt away. In another embodiment, the distance is at least 5 nt away. In another embodiment, the distance is at least 6 nt away. In another embodiment, the distance is at least 7 nt away. In another embodiment, the distance is at least 8 nt away. In another embodiment, the distance is at least 9 nt away. In another embodiment, the distance is at least 10 nt away. In another embodiment, the cut is a staggered cut whose closer cut is at least one of the above distances away from the end of the recognition sequence. In another embodiment, the distance is $10/14$ nt away (i.e. 10 nt on one strand, and 14 on the other). In another embodiment, the distance is $25/27$ nt away. In another embodiment, the distance is any other distance used by a restriction enzyme. In another embodiment, the use of a restriction enzyme that cuts outside of its recognition sequence enables the removal (on one half of the DNA molecule only) of the 5 or more consecutive adenines on the 3' end of the first constant sequence. In another embodiment, the use of such an enzyme enables the removal (on one half of the DNA molecule) of a portion of the 5 or more consecutive adenines. Each possibility represents a separate embodiment of the present invention.

In another embodiment, a method of the present invention enables the identification of a therapeutic RNA molecule that targets more than one gene. In another embodiment, the therapeutic RNA molecule is not substantially homologous (in other embodiments, not more than 10%, 20%, 30%, 40%, 50%, 60%, or 70% homologous) to known cDNA sequences. In another embodiment, a library generated by a method of the present invention exhibits an advantage over libraries generated by other methods because the stem regions or self-complementary regions of the RNA molecules generated thereby are random. In another embodiment, the advantage is the ability to screen the RNA molecules generated thereby by function, without any other sequence or expectation bias. In another embodiment, the advantage is the lack of self-complementarity in the loop region. In another embodiment, the advantage is the length of the stem region. Each possibility represents another embodiment of the present invention.

In another embodiment, the numbers of random sequences generated and/or of cells screened is designed to cover all possible sequences of the ds region of the RNA or a fragment thereof. For example, to cover all possible seed sequences (approximately residues 1-8 of the ds region), 65,500 sequences need be generated. In another embodiment, the seed sequence is held constant based on the previous RNA molecule obtained in a subsequent round of mutagenesis, while the remainder of the ds region is mutagenized. In other experiments, the seed sequence is varied, while the remainder of the ds region is kept constant. In other experiments, residues 2-8 of the seed sequence are kept constant, while residues 1, and 9 onward are varied. Each possibility represents a separate embodiment of the present invention.

In another embodiment, a method of the present invention avoids use of a high salt solution, such as those found in commercial kits for gel purification of DNA fragments from an agarose gel, during library construction. In another embodiment, electric current is run through the gel piece to elute the DNA into a dialysis membrane bag with pore sizes smaller than the DNA. In another embodiment, the method further comprises ethanol precipitation of the DNA. In another embodiment, all steps in the library purification (excepting enzyme digests) are performed at 0-4° C. In another embodiment, pH buffer is present during all times during the library construction. In another embodiment, use of bromophenol blue is avoided during library construction. In another embodiment, 1 of the above precautions reduces the likelihood of formation of intramolecular hairpins during library construction. In another embodiment, flanking sequences on both sides of the stem loop cassette, as introduced during methods of the present invention, prevent formation of intramolecular hairpins during subsequent steps. Each possibility represents a separate embodiment of the present invention.

In another embodiment, the length of the stem or self-complementary region of an RNA molecule of the present invention is 27 nt. In another embodiment, the length is 19 nt. In another embodiment, the length is 6 nt. In another embodiment, the length is 7 nt. In another embodiment, the length is 8 nt. In another embodiment, the length is 9 nt. In another embodiment, the length is 10 nt. In another embodiment, the length is 11 nt. In another embodiment, the length is 12 nt. In another embodiment, the length is 13 nt. In another embodiment, the length is 14 nt. In another embodiment, the length is 15 nt. In another embodiment, the length is 16 nt. In another embodiment, the length is 17 nt. In another embodiment, the length is 18 nt. In another embodiment, the length is 20 nt. In another embodiment, the length is 21 nt. In another embodiment, the length is 22 nt. In another embodiment, the length is 23 nt. In another embodiment, the length is 24 nt. In another embodiment, the length is 25 nt. In another embodiment, the length is 26 nt. In another embodiment, the length is 28 nt. In another embodiment, the length is 29 nt. In another embodiment, the length is 30 nt. In another embodiment, the length is more than 30 nt. Each possibility represents a separate embodiment of the present invention.

In another embodiment, an RNA molecule of the present invention has a stem or self-complementary region of 29 nt with a 3' overhang. In another embodiment, the overhang is 2 nt. In another embodiment, the RNA molecule has a stem or self-complementary region of 27 nt with a 3' overhang. In another embodiment, the overhang is 2 nt. In another embodiment, the RNA molecule has a stem or self-complementary region of 19 nt with a 3' overhang. In another embodiment, the overhang is 2 nt. In another embodiment, the RNA molecule has another of the lengths enumerated above and has a 3' overhang (in another embodiment, a 2 nt 3' overhang).

In another embodiment, an RNA molecule of the present invention has a stem or self-complementary region of 21-23 nt (in another embodiment, of 22 nt) with an intervening loop sequence of 15-25 nt (in another embodiment, of 19 nt). In another embodiment, the intervening loop sequence is 1-30 nt. In another embodiment, the RNA molecule has a mismatch of one or more base pairs in the self-complementary region. In another embodiment, the RNA molecule has a deletion in one strand of the self-complementary region. In another embodiment, the deletion causes an internal loop that is recognized by a cellular enzyme. Each possibility represents another embodiment of the present invention.

In another embodiment, the length of the loop region of an RNA molecule of the present invention is 3-20 nt. In another embodiment, the length is 4-20 nt. In another embodiment, the length is 5-20 nt. In another embodiment, the length is 6-20 nt. In another embodiment, the length is 7-20 nt. In another embodiment, the length is 8-20 nt. In another embodiment, the length is 9-20 nt. In another embodiment, the length is 10-20 nt. In another embodiment, the length is 3-15 nt. In another embodiment, the length is 4-15 nt. In another embodiment, the length is 5-15 nt. In another embodiment, the length is 6-15 nt. In another embodiment, the length is 7-15 nt. In another embodiment, the length is 8-15 nt. In another embodiment, the length is 10-15 nt. In another embodiment, the length is 3-12 nt. In another embodiment, the length is 4-12 nt. In another embodiment, the length is 5-12 nt. In another embodiment, the length is 6-12 nt. In another embodiment, the length is 7-12 nt. In another embodiment, the length is 8-12 nt. In another embodiment, the length is 10-12 nt. In another embodiment, the length is 3-10 nt. In another embodiment, the length is 4-10 nt. In another embodiment, the length is 5-10 nt. In another embodiment, the length is 6-10 nt. In another embodiment, the length is 7-10 nt. In another embodiment, the length is 8-10 nt.

In another embodiment, the length is about 7 nt. In another embodiment, the length is about 19 nt. In another embodiment, the length is about 6 nt. In another embodiment, the length is about 8 nt. In another embodiment, the length is about 9 nt. In another embodiment, the length is about 10 nt. In another embodiment, the length is about 11 nt. In another embodiment, the length is about 12 nt. In another embodiment, the length is about 13 nt. In another embodiment, the length is about 14 nt. In another embodiment, the length is about 15 nt. In another embodiment, the length is about 16 nt. In another embodiment, the length is about 17 nt. In another embodiment, the length is about 18 nt. In another embodiment, the length is about 20 nt. In another embodiment, the length is about 21 nt. In another embodiment, the length is about 22 nt. In another embodiment, the length is about 23 nt. In another embodiment, the length is about 24 nt. In another embodiment, the length is about 25 nt. In another embodiment, the length is about 26 nt. In another embodiment, the length is about 28 nt. In another embodiment, the length is about 29 nt. In another embodiment, the length is about 30 nt. In another embodiment, the length is about more than 30 nt. Each possibility represents a separate embodiment of the present invention.

The loop region of RNAi molecules of the present invention is taken, in another embodiment, from a known or naturally occurring RNAi molecule. In another embodiment, the loop sequence is not from a known or naturally occurring RNAi molecule. It will be understood to those skilled in the art that a variety of loop sequences, including previously unrecognized ones, are suitable for methods of the present invention.

Naturally occurring RNAi molecules are well known in the art, and are described for example, in Griffiths-Jones et al (Griffiths-Jones S, Grocock R J, van Dongen S, Bateman A, Enright A J. Nucl Acids Res, 2006, 34: D140-D144) and in Griffiths-Jones S (Nucl Acids Res, 2004, 32: D109-D111). Each possibility represents a separate embodiment of the present invention.

In another embodiment, an RNA molecule of the present invention is a substrate for an RNA-induced silencing complex (RISC). In another embodiment, a method of present invention further comprises digesting an RNA molecule of the present invention to obtain a short-interfering (siRNA) molecule. In another embodiment, the RNA molecule is a substrate for an RNase III family enzyme. In another embodiment, the enzyme is a Class I RNase III family enzyme. In another embodiment, the enzyme is a Class II RNase III family enzyme. In another embodiment, the enzyme is a Class III RNase III family enzyme. In another embodiment, the enzyme is Dicer. In another embodiment, the enzyme is Drosha. In another embodiment, the enzyme is any other enzyme that with specificity for double-stranded RNA. In another embodiment, processing by a RISC or RNase III family enzyme converts the RNA molecule to a form with a biological activity. Substrates for RISC and RNase III family enzymes are well known in the art, and are described, for example, in Jaronczyk K et al (Exploring the functions of RNA interference pathway proteins: some functions are more RISCy than others. Biochem J. 2005 May 1; 387(Pt 3):561-71) and in Banan M et al (The ins and outs of RNAi in mammalian cells. Curr Pharm Biotechnol. 2004 October; 5(5):441-50). In another embodiment, an RNA molecule of the present invention is cleaved by one of the above enzymes or complexes into a double-stranded RNA with a stem or self-complementary region of 20 nt and a 3' overhang (in another embodiment, a 2 nt 3' overhang). Each type of substrate represents a separate embodiment of the present invention.

In another embodiment, the digestion occurs inside a target cell. In another embodiment, the RNA molecule is used to generate any other type of RNAi (inhibitory RNA) molecule known in the art. Each type of RNA molecules represents a separate embodiment of the present invention.

In another embodiment, an RNA molecule of the present invention mimics a product of an RNase III family enzyme. In another embodiment, the RNA molecule has a 20 nucleotide ds region and a 2 nucleotides 3' overhang. In another embodiment, the RNA molecule has any other structure known in the art of a product of an RNase III family enzyme. Each possibility represents a separate embodiment of the present invention.

In another embodiment, a biologically active RNA molecule of the present invention binds to a sequence shared by several genes. In another embodiment, the shared sequence is found in the 3' untranslated region (UTR) of the target mRNAs. In another embodiment, the shared sequence is found in the 5' UTR of the target mRNAs. In another embodiment, the shared sequence is found in the coding portion of the target mRNAs. In another embodiment, the shared sequence is found in an intron. In another embodiment, the shared sequence is found in a combination of the above regions. Each possibility represents a separate embodiment of the present invention.

In another embodiment, the target of an RNA molecule of the present invention is an mRNA molecule. In another embodiment, the target is another type of RNA. In other embodiments, the target is ribosomal RNA (rRNA), transfer RNA (tRNA), messenger RNA (mRNA), small nuclear RNA (snRNA), small nucleolar RNA (snoRNA), microRNA (miRNA), or XIST RNA. In another embodiment, the target is a deoxyribonucleotide molecule. In another embodiment, the target is another type of nucleotide molecule. In another embodiment, the target is a protein molecule. In another embodiment, the target is a cofactor. In another embodiment, the target is a lipid. In another embodiment, the target is another type of cellular non-nucleotide molecule. Each possibility represents a separate embodiment of the present invention.

The complementary region between an RNA molecule of the present invention and its target sequence is, in another embodiment, 5 nt in length. In another embodiment, the length of the complementary region is 6 nt. In another embodiment, the length of the complementary region is 7 nt. In another embodiment, the length is 8 nt. In another embodiment, the length is 9 nt. In another embodiment, the length is 10 nt. In another embodiment, the length is 11 nt. In another embodiment, the length is 12 nt. In another embodiment, the length is 13 nt. In another embodiment, the length is 14 nt. In another embodiment, the length is 15 nt. In another embodiment, the length is 16 nt. In another embodiment, the length is 17 nt. In another embodiment, the length is 18 nt. In another embodiment, the length is 19 nt. In another embodiment, the length is 20 nt. In another embodiment, the length is 21 nt. In another embodiment, the length is 22 nt. In another embodiment, the length is 23 nt. In another embodiment, the length is 24 nt. In another embodiment, the length is 25 nt. In another embodiment, the length is 26 nt. In another embodiment, the length is 27 nt. In another embodiment, the length is 28 nt. In another embodiment, the length is 29 nt. In another embodiment, the length is 30 nt. In another embodiment, the length is more than 30 nt. In another embodiment, an RNA molecule of the present invention binds different target sequences on different genes. In another embodiment, the different target sequences are not all the same length. Each possibility represents a separate embodiment of the present invention.

In another embodiment, the RNA molecule expressed by a vector of the present invention is fully complementary to its target sequence. In another embodiment, the RNA molecule is partially complementary to its target sequence. In another embodiment, the RNA molecule is complementary to its target sequence along most of the length of the RNA molecule, with a non-complementary overhang region. In another embodiment, the RNA molecule expressed by a vector of the present invention has one or more mismatched residues with respect to its target sequence. In another embodiment, the RNA molecule hybridizes to its target sequence under physiological conditions. In another embodiment, the RNA hybridizes to its target sequence under stringent conditions. Each possibility represents a separate embodiment of the present invention.

In another embodiment, expression of an RNA molecule of the present invention inside a cell causes translational repression of the target RNA molecule. In another embodiment, expression of the RNA molecule causes cleavage or degradation of the target RNA molecule. In another embodiment, whether translational repression, cleavage or degradation occurs depends on the level of complementarity between the RNA molecule of the present invention and the target RNA molecule, and the length of the complementary region. Each possibility represents another embodiment of the present invention.

In other embodiments, methods of present invention are used to identify sequences that influence cell survival, cell health, cell death, cell differentiation, or any other assayable phenotypic change. In another embodiment, sequences influencing stem-cell differentiation into cell types of medical interest are identified using the library. In another embodiment, the RNA molecules identified have utility as siRNAs for stem-cell therapeutics. Each possibility represents a separate embodiment of the present invention.

EXPERIMENTAL DETAILS SECTION

Example 1

Dual RNAi Expression by a Retroviral Vector

Figure 12:
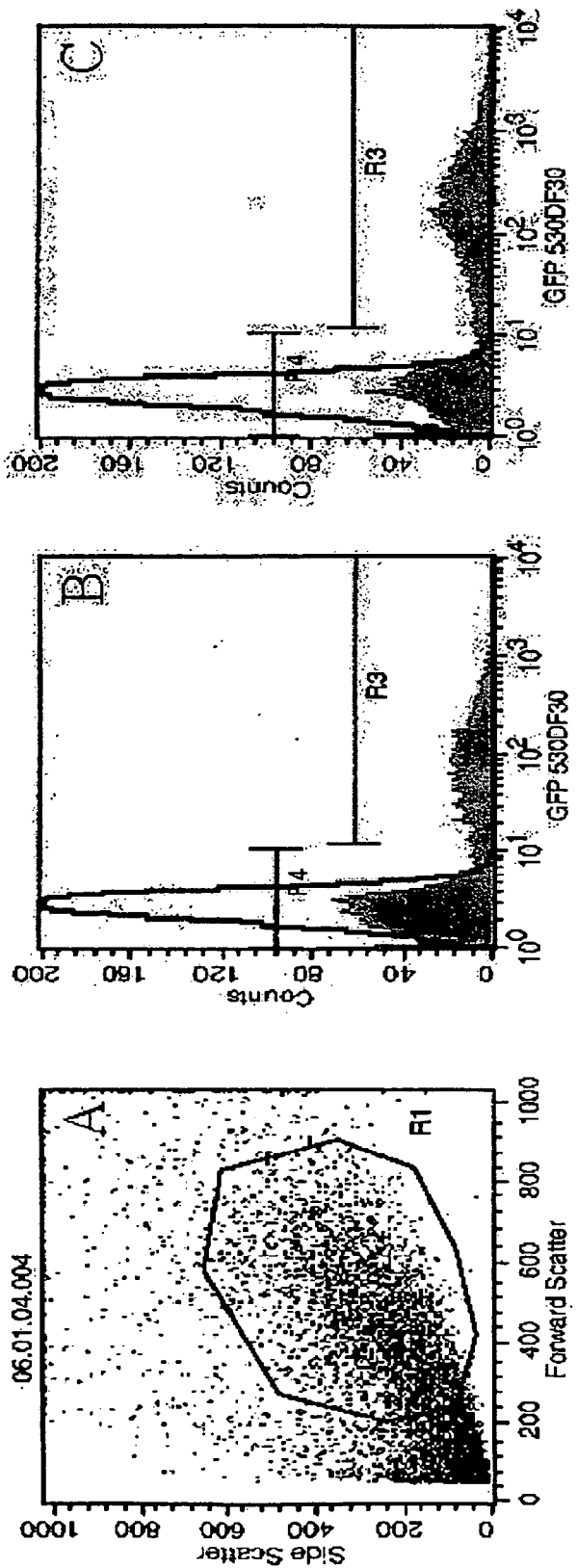
FIG. 12. Flow-cytometric analysis of DLD1 cells infected with pQe2 48 hours previously. A. Forward-scatter versus side-scatter gating for live cells. A second gating (forward-scatter versus forward-scatter-width) to enrich for non-aggregated cells was performed. B. Flow-cytometric analysis of infected cells for eGFP expression. Approximately 30% of the gated cells from panel A express eGFP. C. Flow-cytometric analysis of infected cells for eGFP expression. Approximately 50% of gated cells express eGFP.

A retroviral vector was designed to express simultaneously two shRNAs. The vector contained enhanced, farnesylated green-fluorescent protein (eGFPf), which allows straightforward flow-sorting of infected or transfected cells, and a G418 resistance gene, which facilitates selection of infected or transfected cells. The eGFP gene of the retroviral vector pQCXIX® (Clontech) was replaced with eGFPf, and two copies of a Pol III-dependent H1-promoter cassette (from pSuper-Retro) were cloned into the inactivated long-terminal repeat of pQCXIX, to create the vector pQe2. In each H1-promoter cassette of pQe2, 2 unique restriction enzyme sites were incorporated to allow independent cloning of shRNA constructs into each cassette. pQe2 was used to knock down expression of proteins important in spindle-checkpoint function; both shRNA knockdown (by Western and other analyses) and eGFP expression have been validated. FIG. 12 depicts flow-cytometric analyses of the moderately infectable colon-carcinoma cell line DLD1 infected with pQe2. FIG. 13 depicts effective shRNA knockdown of eGFP itself using pQe2. Thus, expression of target genes can be knocked down by RNA molecules. In addition, expression of both a particular gene of interest (e.g. frataxin) can be suppressed in normal cells to induce a phenotype (or, in another embodiment, a disease phenotype) and one or more random targets can be suppressed as well to alter or reverse the phenotype.

Example 2

Vector Modification pSuper-Retro (Oligoengine®, Seattle, Wash.), which can be packaged as a retrovirus and includes the gene encoding enhanced green fluorescent protein (eGFP) and a G418-resistance gene, was used in the cloning methods below. The Bgl II-Mlu I fragment of the spacer sequence was replaced with a Bgl II-Bbs I-Mlu I fragment. By then cutting with Bbs I, filling in with Klenow, and cutting with Not I, the linearized vector depicted in FIG. 5 was created. Other than Pme I, which was eliminated in creating the spacer sequence, pSuper-Retro lacked all the relevant restriction enzyme sites needed for the procedure shown in FIGS. 6-8, and thus was suitable for the procedure.

In the development of alternate vectors, the Bgl II cloning site and the spacer sequence between Bgl II and Hind III of pSuper-Retro were replaced with Xcm I and Sfi I to eliminate the unique Pme I site. (The region from just before the Bgl II site back to the unique BlpI site was PCR amplified, using a primer with a tail containing the sequences for Xcm I, Sfi I, and Hind III, and the vector's Blp I-Hind III fragment was replaced with the PCR product digested with Blp I and Hind III). A spacer sequence was added between XcmI and SfiI by amplifying the old spacer sequence, up to but not including the PmeI site, using primers with tails containing the sequences for XcmI and SfiI. The rationale for adding back a spacer sequence was, in this experiment, to simplify the elimination of single-cut vector and thereby maximize the efficiency of the library ligation. Other than Pme I, which was eliminated as described above, pSuper-Retro lacked all the relevant restriction enzyme sites needed for the procedure shown in FIGS. 3, 4, and 5, and thus was suitable for the procedure.

Many other vectors could be used and many other restriction enzyme combinations are suitable for the methods in this and the other Examples herein. For example, enzyme pairs that can be used to create non-complementary loop sequences (with the resulting loop sequences in parentheses) include, EcoN I/Aar I (CCTCCCGC), Sma I/Aar I (CCCC), Stu I/Apa I (AGGC), Bsu36 I/Aar I (CCTCAC), Bbv CI/Aar I (CCTCAC), Ear I/Aar I (TCTTCCGC), etc.

Example 3

Creation of a Library of Partially Self-Complementary RNA Molecules

A set of single-stranded (ss) DNA molecules was obtained, comprising, from 5' to 3', a first constant region ("N21"), followed by a region of random sequence, in this embodiment a random sequence of 21 nucleotides (nt), followed by a second constant region containing 1 strand of a site of a first restriction enzyme (in this case EcoNI). A representation of a single ss molecule from the set is depicted in FIG. 1 as "ssI," also referred to herein as "single-stranded nucleic acid intermediate I." A primer mismatched at two positions ("primer A" in FIG. 1) was annealed to the oligo, such that the complementary strand, when in double-stranded form, was a substrate for a second restriction enzyme (in this case AarI), but not the first restriction enzyme, as depicted in FIG. 1. One round of extension generated a complementary strand to most of ssI (bottom strand of ssIB in FIG. 1). After the single extension, a hairpin-loop linker ("linker B" in FIG. 1) was ligated to the staggered, complementary end of the extended oligonucleotide, generating nucleic acid intermediate II ("n.a. II" in FIG. 1). Nucleic acid intermediate II contains, in 5'-3' order, (a) a first copy of the first constant region; (b) a first copy of N21; (c) a first copy of the second constant region; (d) the hairpin-loop linker; (e) the reverse complement of the second constant region ("N21c"); (f) the reverse complement of the region of random sequence; and (g) the reverse complement of the first constant region (depicted in bottom of FIG. 3).

Figure 2:
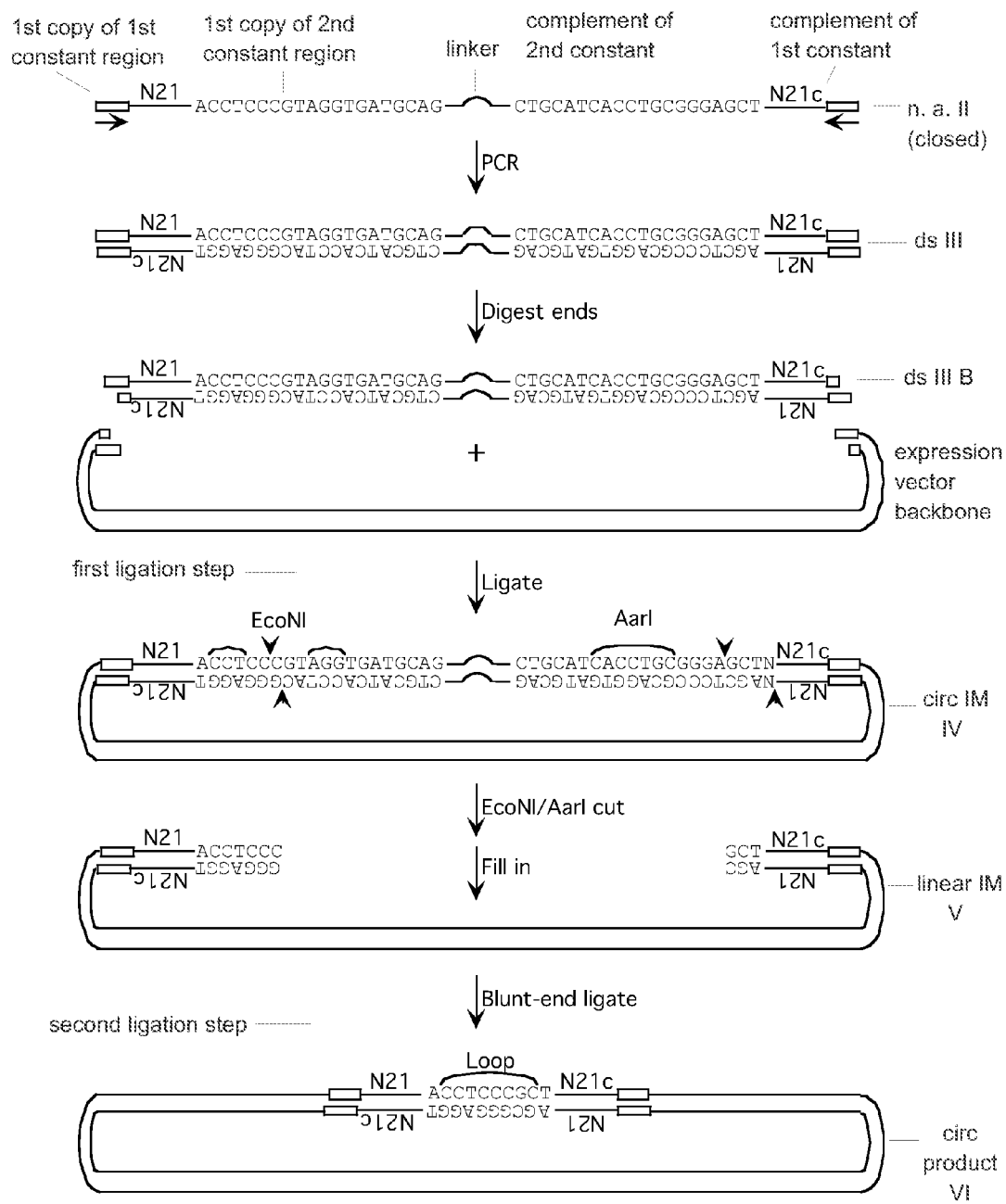
FIG. 2: strategy for creation of a library of expression vectors for partially self-complementary RNA molecules, part II. Described in Example 3. Sequences of 10 or more nt and not previously assigned a SEQ ID No are listed as SEQ ID No: 7-12.

In another embodiment, as depicted in FIG. 2, the single-stranded product depicted at the bottom of FIG. 1 is suitable for amplification by PCR, thereby generating a double-stranded inter-mediate III ("ds III" in FIG. 2). ds III contains, in 5'-3' order with respect to the top strand, (a) a first, double-stranded copy of the first constant region; (b) a first, double-stranded copy of N21; (c) a first, double-stranded copy of the second constant region; (d) a double-stranded copy of the hairpin-loop linker; (e) a second, inverted double-stranded copy of the second constant region; (f) a second, inverted double-stranded copy of N21c; and (g) a second, inverted double-stranded copy of the first constant region.

After PCR, the ends are restriction-enzyme digested, using a restriction enzyme site in the first constant region, and the product is ligated into a vector (first ligation step, FIG. 2), downstream of the polymerase-III H1-RNA promoter, thereby generating circular intermediate IV ("circ intermediate IV"). The resulting plasmid is then restriction digested with EcoNI and AarI. As a result of the original mismatched primer, only 1 of the 2 restriction enzyme sites is found on each side of the plasmid insert. Both enzymes leave overhanging 5' ends. After filling in to create blunt ends, the plasmid is ligated back into a circle in a uni-molecular, blunt-end ligation (second ligation step, FIG. 2), thereby generating a circular product VI ("circ product VI"). The resulting plasmids contain regions of random sequence, each followed by a downstream non-conserved loop sequence, and then followed by a reverse complement of the random sequence, all in the same, coding strand of DNA, and thus expressed a library of shRNA molecules with a 22-base-pair stem containing a random, 21-base-pair region followed by a TA pair, and a non-complementary, 8 nt loop.

In this embodiment, there is a complementary T-A flanking the loop (bottom of FIG. 2). This is necessitated by the need to match the lead base-pair in the original mismatch extension shown at the top of FIG. 1. In additional experiments, by creating 4 libraries, each with a different base at this position, and then mixing them, all possibilities of a random 22-base-pair sequence in the stem are made. These constructs thus express an shRNA with a random, 22-base-pair stem, and a non-complementary, 8 nt loop.

Example 4

An Additional Approach for Creation of a Library of Partially Self-Complementary RNA Molecules FIGS. 3, 4, and 5 illustrate an additional approach for generating the library of expression vectors for RNAi. The DNA oligomer ("oligo") ssI on the top line of FIG. 3 is similar to ssI of FIG. 1; "N28" refers to 28 random nucleotides. ssI contains one strand of a PmeI site in the second constant region, just downstream of the N28 sequence. Simple extension from a primer (with 2 mismatches; "primer A" in FIG. 3) created the reverse complement of most of the first constant region, the region of random sequence ("n28"); and the second constant region of ssI, thereby generating double-stranded intermediate IB ("ds IB"). Ligation of a hairpin-loop linker to I end of the extended oligonucleotide covalently linked the 2 strands of ds Ib containing the N28 and n28 sequences, thereby generating nucleic acid intermediate II ("n.a. II"). (The compatible sticky ends of the extended oligonucleotide and the hairpin-loop linker were from SalI and Xho I sites, respectively; digestion with Sal I and Xho I cut homodimers of the extended oligonucleotide or hairpin-loop linker, respectively, but did not cut the desired, heterodimeric product, thereby allowing gel separation by size.) n.a. II contains, in 5'-3' order, (a) a first copy of the first constant region; (b) a first copy of the region of random sequence "N28"; (c) a first copy of the second constant region; (d) the hairpin-loop linker; (e) the reverse complement of the second constant region; (f) the reverse complement of the region of random sequence "n28"; and (g) the reverse complement of the first constant region.

Use of a mismatched primer created one strand of an Aar I recognition sequence in the reverse complement of the second constant region, just upstream of the n28 sequence; which was not present in the first copy of the second constant region. In addition, the mismatched primer eliminated the Pme I recognition sequence in the reverse complement of the second constant region. This created the asymmetry used to generate a non-complementary loop between N28 and n28 after insertion into the vector (see hereinbelow and FIG. 5).

Creating the Reverse Complement of the Random Stem Sequence and Covalently Linking the Two In another embodiment, as depicted in FIG. 4, n.a. II is suitable for simple extension from mismatched primer B (top of FIG. 4), thereby generating double-stranded intermediate III ("ds III"). The primer is recessed to create a 5' overhang (AGA) in dsIII (see below). The mismatch in the primer eliminates the BtgZ I site at one end of dsIII. ds III contains, in 5'-3' order with respect to the top strand, (a) a first, double-stranded copy of the first constant region; (b) a first, double-stranded copy of N28; (c) a first, double-stranded copy of the second constant region; (d) a double-stranded copy of the hairpin-loop linker; (e) a second, inverted double-stranded copy of the second constant region; (f) a second, inverted double-stranded copy of n28; and (g) a second, inverted double-stranded copy of the first constant region.

As noted above, dsIII contains a 5' overhang (AGA) compatible with the 5' overhang in the expression vector backbone digested with Sfi I (FIG. 4), and contains an BtgZ I site on the other end of the molecule. Digestion of ds III with BtgZ I, which cuts 10 and 14 nt away from the recognition site, cuts the DNA immediately before the first random nt of the original N28, as well as 4 nt further in on the opposite strand, leaving a recessed 3' end (ds IIIB). Filling in with Taq polymerase regenerates the 4 nt in the strand opposite the original N28, plus a 3' adenine overhang (ds IIIC), which is compatible with the 3' thymidine overhang in the expression vector backbone digested with Xcm I. dsIIIC is then ligated into the expression vector backbone (first ligation step, FIG. 4), to generate circular intermediate IV ("circ IM IV"). A variety of expression vector backbones are suitable for this step, e.g. Modified pSuper-Retro (Example 2).

Creating the Vector Insert and Insertion into the Vector

The purpose of the BtgZ I digestion and filling in is to retain the 5 thymidines that serve as the pol III transcription termination signal immediately downstream of the original n28 sequence, while eliminating the adenines upstream of the original N28 sequence and replacing them with pyrimidines (from the vector). Because pol III tends to initiate transcription early when purines are available immediately upstream of the normal start site, pyrimidines immediately upstream favor initiation of transcription at the normal start site, which is 25 nucleotides downstream of the TATA box in the H1 promoter. Thus, in circ IM IV, the normal start site falls on the first nucleotide of the original N28 sequence, which is marked "+25" at the bottom of FIG. 4 (see below).

Creation of the Non-Self-Complementary Loop Sequence

The top of FIG. 5 depicts the vector insert sequence of circ IM IV between the N28 and n28 sequences. The insert sequence contains a PmeI/AarI restriction site asymmetry as a result of the restriction site asymmetry in n.a. II (described hereinabove). Digestion of circ IM IV with Pme I creates a blunt end preceded by GGTTT in the sense strand. Digestion with Aar I cuts the DNA three nt before the first random nucleotide of the original n28, as well as 4 nucleotides further in on the opposite strand, leaving a recessed 3' end. Filling in with Klenow creates a blunt end followed by AGC in the sense strand ("linear intermediate V" in FIG. 5). Uni-molecular, blunt-end ligation of linear IM V (second ligation step, FIG. 4), yields circular product VI ("circ product VI"), containing a non-self-complementary loop region with sequence GTTTAG between N28 and n28.

Use of a matching lead base-pair in the original primer extension shown at the top of FIG. 3 was the reason for the complementary G-C flanking the non-self-complementary loop depicted in FIG. 5. In another embodiment, by repeating the procedure shown in FIGS. 3, 4, and 5, each time with a different base at the lead position for the first primer extension, 4 sub-libraries are created, which, when mixed, constitute an shRNA library with a random 29-base-pair stem and a non-self-complementary loop of GTTTAG. A pol III promoter (H1), ending in 4 pyrimidines, precedes each shRNA construct in the library, with the transcriptional start site falling on the first random nucleotide. Five thymidines immediately downstream of the second half of the 29-base-pair stem serve as the transcription termination signal.

Example 5

A Third Approach for Creation of a Library of Partially Self-Complementary RNA Molecules FIGS. 6-8 illustrate a third approach used for generating the library of expression vectors for RNAi:

Creating the Reverse Complement of the Random Stem Sequence, Covalently Linking the Two, and Starting the Second Extension As in the previous method, a single-stranded DNA molecule "single-stranded nucleic acid intermediate I" with a region of random sequence sandwiched between 2 constant regions ("first constant region" and "second constant region," 5' and 3', respectively, to region of the random sequence) was synthesized (referred to as "ss I" in FIG. 6). The second constant region contains 1 strand of a Pme I recognition site just downstream of the NsNsN26 sequence. In ss I, "NsNsN26" refers to 28 random nt, the first 2 of which are followed by phosphorothioate bonds (to create asymmetric BtgZ I cutting after the second extension, as described hereinbelow and depicted in FIG. 7). ss I also contained 1 strand of Not I and BtgZ I recognition sequences, as depicted for ds Ib in FIG. 6.

Simple extension from a recessed primer, containing 2 mismatches, created ds Ib, containing the reverse complements of: (a) a fragment of the first constant region, (b) the NsNsN26 sequence, and (c) the second constant region.

Use of a mismatched primer created one strand of an Aar I recognition sequence in the reverse complement of the second constant region, just upstream of the n26nn sequence; which was not present in the first copy of the second constant region. In addition, the mismatched primer eliminated the Pme I recognition sequence in the reverse complement of the second constant region. This created the asymmetry used to generate a non-complementary loop between NsNsN26 and n26nn after insertion into the vector (see hereinbelow and FIG. 8).

Ligation of a hairpin-loop linker ("linker B") to the recessed-primer end of ds Ib covalently linked the 2 strands of ds Ib, containing the NsNsN26 and n26nn sequences, and completed the reverse complement of the first constant region, thereby generating nucleic acid intermediate II ("n.a. II"). (The compatible sticky ends of ds Ib and linker B are from Sal I and Xho I sites, respectively; digestion with Sal I and Xho I cut homodimers of ds Ib or linker B, respectively, but did not cut the desired, heterodimeric product, thereby facilitating gel separation by size.) n.a. II contains, in 5'-3' order, (a) a first copy of the first constant region; (b) a first copy of the region of random sequence ("NsNsN26"); (c) a first copy of the second constant region; (d) the hairpin-loop linker; (e) the reverse complement of the second constant region; (f) the reverse complement of the region of random sequence ("n26nn"); and (g) the reverse complement of the first constant region.

To facilitate the second extension (starting at the bottom of FIG. 6 and continuing at the top of FIG. 7), a nick site was created with the nicking enzyme N.BbvC, which cuts only 1 strand of DNA (indicated by arrowhead in FIG. 6), then the resulting 5' fragment was extended with the strand-displacing DNA polymerase Bst (depicted at bottom of FIG. 6 and top of FIG. 7) to create the reverse complement of n.a. II, thereby generating double-stranded intermediate III (ds III). ds III contains, in 5'-3' order with respect to the top strand, the following regions, all double-stranded: (a) a second, inverted copy of the first constant region; (b) a second, inverted copy of the random region (n28); (c) a second, inverted copy of the second constant region; (d) a copy of the hairpin-loop linker; (e) a first copy of the second constant region; (f) a first copy of the random region (N28); and (g) a first copy of the first constant region. In ds III of this embodiment, the regions are synthesized in the reverse order from the previous Example, and thus are depicted in the reverse order from the previous Example.

The phosphorothioate bonds originally appearing in ssI (top of FIG. 6) created a restriction site asymmetry in ds III, wherein BtgZ I only cuts 1 end of ds III. Digestion of ds III with BtgZ I cut the DNA immediately before the first random nucleotide of the newly synthesized N28, as well as 4 nucleotides further in on the opposite strand, leaving a recessed 3' end (FIG. 7; ds IIIB). Filling in with Klenow regenerated the four nucleotides in the strand opposite the newly synthesized N28, creating a blunt end. As described for the above Example, the asymmetric BtgZI digestion enabled inclusion of a TTTTT termination sequence after the last random nucleotide while changing the complementary AAAAA to 5 pyrimidines just upstream of the H1 transcription start site at the first random nucleotide.

Finishing the Second Extension to Create the Vector Insert, and Insertion into the Vector The asymmetric BtgZ I digestion also eliminated 1 of the 2 Not I sites. Digestion with Not I created the library insert (ds IIIC), which was ligated into the vector backbone (first ligation step, FIG. 7), thereby generating circular intermediate IV. The top of FIG. 8 depicts the vector insert sequence between the N28 and n28 sequences. As a result of the mismatch in primer A (FIG. 6), a unique Aar I site was present at 1 end of the insert and a unique Pme I site at the other end. Digestion with Pme I created a blunt end followed by AAACC in the sense strand. Digestion with Aar I cut the DNA 3 nucleotides before the first random nucleotide of the original n28, as well as 4 nucleotides further in on the opposite strand, leaving a recessed 3' end. Filling in with Klenow fragment created a blunt end with GCT in the transcribed strand immediately following N28 ("linear intermediate V"). Uni-molecular, blunt-end ligation of linear intermediate V (second ligation step, FIG. 8), generated circular product VI, containing a non-complementary CTAAAC loop sequence between N28 and n28.

The transcribed strands of the inserts contained 5 pyrimidines upstream of the transcription start site (to increase the efficiency of starting transcription at +1, which pol III prefers to be a purine), followed by a 29-nt stem containing a 28-nt random sequence, followed by a non-complementary loop sequence, followed by the reverse complement of the 29-nt random sequence, followed by 5 thymidines (to terminate pol III transcription, which occurs after the second thymidine). Thus, the vectors encoded shRNAs with 29-nt stems and 2-nt overhangs.

Figure 9:
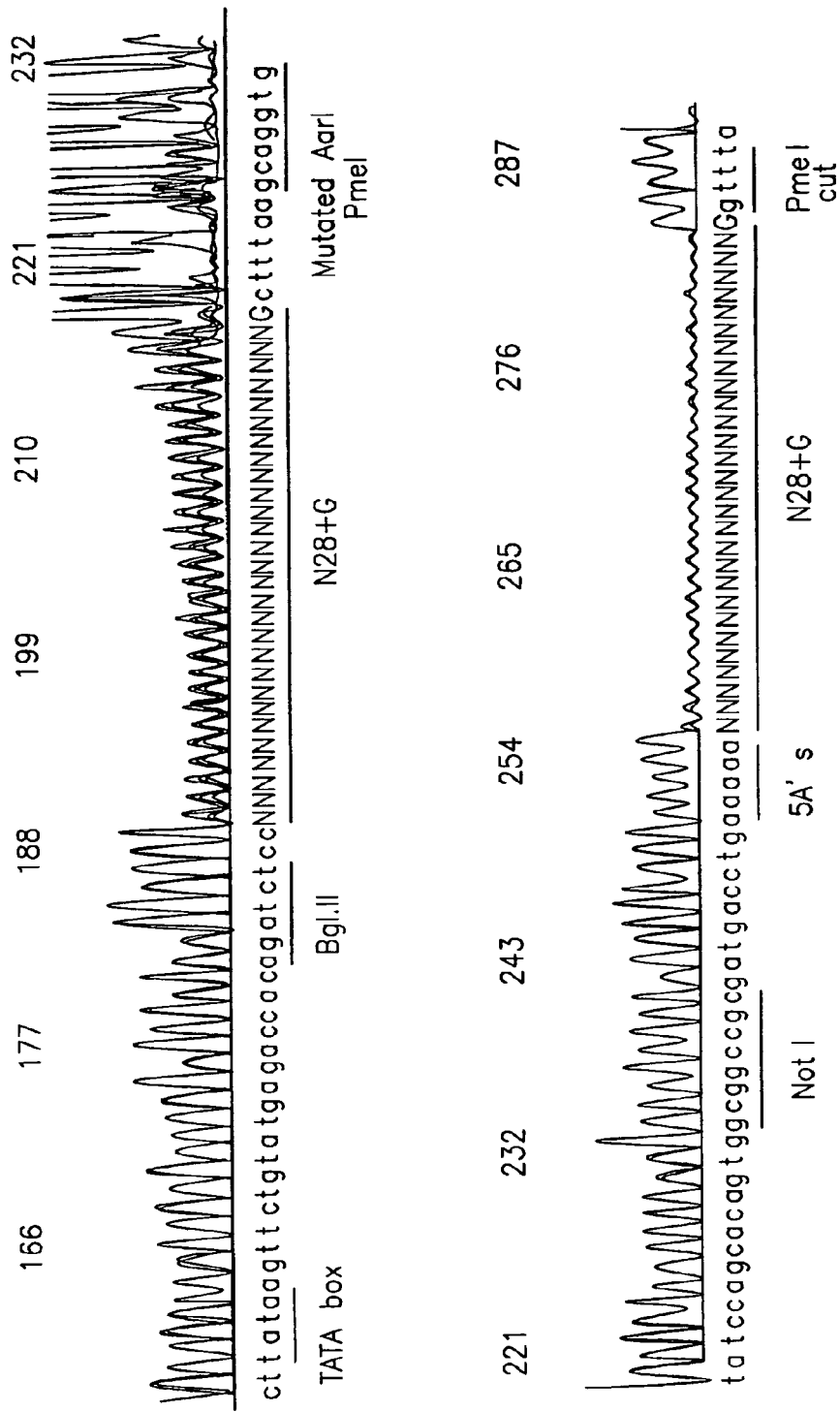
FIG. 9. Sequencing data from intermediates of the library created according to the method described in Example 5, prior to the Aar I/Pme I digestion (bottom of FIG. 7); since sequences of all clones are superimposed, each residue in the random region of the depiction depicts the presence of all 4 bases, demonstrating random character of these regions (SEQ ID NO: 54). Sequence confirms the presence of the expected constant sequences, and lack of bias in the random regions.

To test the efficacy of the method, E. coli were transfected with circular IM IV, and 300,000 colonies were plated out. Plasmid DNA from 15 of these colonies was isolated, and inserts were sequenced. The sequences of all 15 inserts contained random sequences and their reverse complements separated by the Aar I-Pme I fragment depicted in the top of FIG. 8, exactly as predicted. In addition, the pool of intermediates was sequenced. As depicted in FIG. 9, the sequence data confirmed the presence of the expected constant sequences, and lack of bias in the random region, verifying the efficacy of the method. The base usage of the random sequences was 50.9% A/T and 49.1% G/C, demonstrating that the random region exhibits random character.

DNA was prepared from the remaining (~300,000) colonies, digested sequentially with Aar I and Pme I. and re-ligated. The ligation mix was used to transfect E. coli, and 1,000,000 colonies were plated out. Plasmid DNA was isolated from 5 of these colonies; all 5 had inserts of the proper size.

Following completion of the method, the random (n29) regions of 14 clones were sequenced. As depicted in FIG. 10, the sequences exhibited no detectable skewing, demonstrating that the method was efficacious, and the final product corresponded exactly to the desired product.

Figure 11:
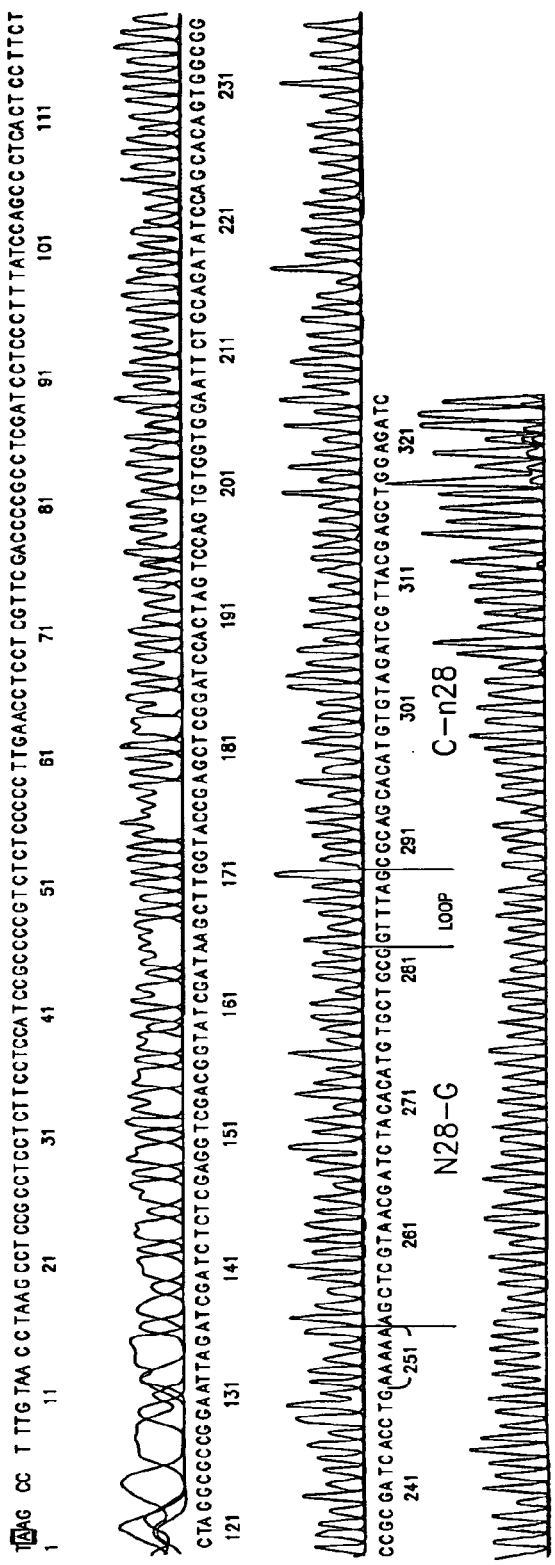
FIG. 11. The sequence of a single "clone" from the final library. Depicted are the random sequence of N28, followed by a "G" residue (supplied by the 5' end of the second constant region of the original single-stranded (ss) DNA molecule), followed by the loop sequence, a "C" residue, and the reverse complement of N28, (depicted as "n28.") The sequence corresponds to the bottom (upside-down) strand at the bottom of FIG. 8, confirming that the final product corresponded exactly to the desired product. (SEQ ID NO: 69).

In addition, inserts from individual "clones" from the completed library were sequenced in their entirety. FIG. 11 depicts the sequence from a representative clone. The clone contains the N28 random sequence, followed by a "G" residue (supplied by the 3' constant region of the original ss DNA molecule), followed by the loop sequence, followed by a "C" residue, followed by the reverse complement of N28, (depicted as "n28.") The sequence corresponds to the bottom (upside-down) strand at the bottom of FIG. 8. Thus, the final product corresponded exactly to the desired product, re-confirming that the method was efficacious.

Example 6

Establishment of Apoptosis-Inhibiting Assays for Screening the shRNA Library 293T cells (a human, embryonic kidney cell line) were treated overnight (16 hours) with 2, 4, 6, and 8 µM of the synthetic triterpenoid, CDDO. After replacement with medium without CDDO, plates treated with 4, 6, or 8 µM had no remaining adherent cells, while the plate treated with 2 µM CDDO did have some adherent cells. The experiment was repeated with 4 µM; even after five days of post-treatment culture in medium without CDDO, no adherent colonies were evident.

In other experiments, the medium of 293T cells was replaced with 50%, 20%, 10%, 5%, 2%, and 0% serum-free medium in phosphate buffered saline (PBS) for 24 hours, after which the cells were cultured in normal medium for 5 days. There were no remaining cells in the plates treated with 5%, 2%, or 0% serum-free medium; while plates treated with 50% and 20% serum-free medium in PBS were mostly viable. Out of ~750,000 cells treated with 10% serum-free medium in PBS, there were two colonies visible on the plate. Thus, treatment for 24 hours with 5-10% serum-free medium in PBS induces ~100% viability loss of 293T cells.

In additional experiments, 293T cells are treated with 3 µM CDDO and/or 6%, 7%, 8%, or 9% serum-free medium in PBS, in order to establish the minimum conditions under which 100% of the cells die, thereby further facilitating rescue by the shRNA library.

In other experiments, apoptosis is induced in 293T cells using the glucose/glucose oxidase (G/GO) technique. Glucose oxidase catalyzes the formation of hydrogen peroxide at an essentially continuous rate. Various glucose oxidase concentrations were tested, doubling at first from 2 mU/ml to 128 mU/ml, as well as extended times of incubation, followed by microscopic examination of the cells, to determine the best concentrations and times to be used. By washing the cells, adding back normal medium, and looking for colony formation, the minimum conditions under which 100% of the cells die were confirmed.

Example 7

Use of the shRNA Library to Identify RNA Molecules with Ability to Inhibit Apoptosis Materials and Experimental Methods Cells FL5.12 cells were obtained from Dr. Craig Thompson.
Generation of High-Titer Retrovirus High-titer retrovirus was generated by co-transfecting 293T cells with retroviral vector and pCL-Eco, which encodes both ecotropic envelope and gag-pol proteins, using an Effectene® transfection kit (Qiagen). Culture supernatant was harvested each day from 24-72 hours after transfection and used either to infect FL5.12 cells or frozen at −80° C. for future use. 1-2 million cells were seeded in each well of a 24-well plate and were centrifuged at 2500×g for 1 hour with viral supernatant, 5 µg/ml polybrene, and 0.3 ng/ml interleukin-3 (IL-3). Cells were stored in the incubator for 2 hours. Viral supernatant was replaced with fresh batches, and the spin/incubation process was repeated 2 more times. Infection efficiency was determined 24-48 hours later by flow cytometric analysis of GFP expression.

Results

The murine pro-B cell line FL5.12 is IL-3 dependent; 100% of the cells die by apoptosis after IL-3 withdrawal for 3 days, and >90% of cells can be rescued by expression of Bcl-xL59. To define a protocol for identification of RNA molecules that rescued the cells from apoptosis, FL5.12 cells were cultured in medium with IL-3 and switched to medium without IL-3 for 12, 24, 48, or 72 hours, after which the cells were returned to medium with IL-3. Both trypan blue exclusion and re-culturing for several days after switching back to medium with IL-3 demonstrated that either 48 or 72 hours was sufficient to ensure 100% loss of viability.

High-titer retroviral infection was calibrated to 30% GFP-positive FL5.12 cells using pSiren, pCL-Eco in a 2:1 molar ratio as a positive control, indicating that 30% of the cells were transduced with a recombinant RNA-expressing retroviral vector.

30% GFP-positive cells was chosen to avoid saturating the RISC complex. Because there is a finite amount of RISC complex per cell, more than 2 or 3 RNAi constructs present simultaneously may be less effective, unless the RNAi sequences are particularly potent. To maximize the chances of identifying effective shRNA sequences with even weak effects, interrogation of primarily 1 random shRNA per cell was thus performed. From the Poisson distribution, multiplicities of infection of 0.3 and 0.4 are associated with approximately 26% and 33% GFP positive cells, respectively, and associated with approximately 85% and 80% of GFP-positive cells being infected with only 1 shRNA-encoding construct, respectively.

Figure 14:
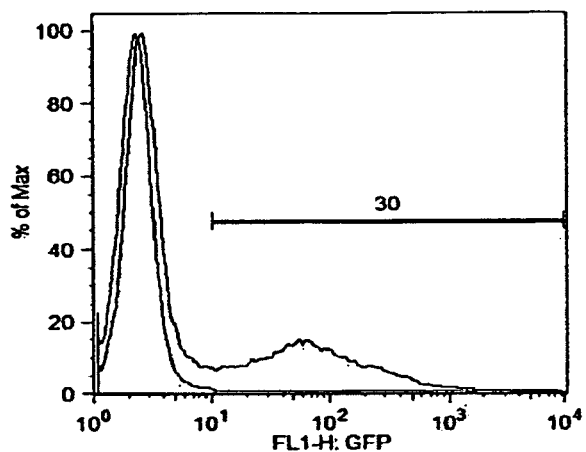
FIG. 14. Retroviral infection of 30% of FL5.12 cells.
Figure 15:
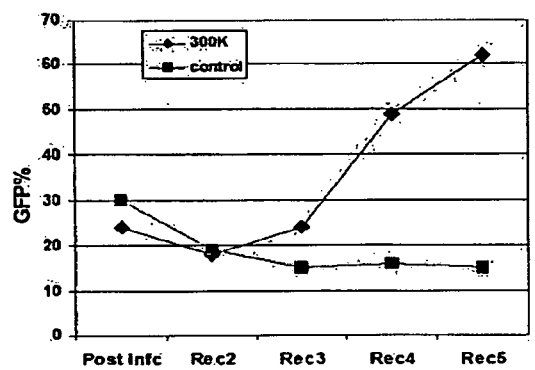
FIG. 15. Enrichment of GFP positive cells infected with the 300K library after multiple rounds of IL-3 withdrawal and recovery.

1 million FL5.12 cells were infected to ~30% GFP positivity with the 300,000 colony library of Example 8; GFP expression after expression is depicted in FIG. 14. IL-3 was withdrawn to select for shRNAs that enhance survival. After 3 days in IL-3-negative medium, cells were transferred back to regular growth medium with 0.3 ng/ml IL-3 for 3 days. To enrich for true positives, the process of withdrawal and return to regular medium was repeated. After 4 rounds of IL-3 withdrawal and recovery, the percentage of GFP-positive cells in the library-infected wells (but not in the control-infected wells) rose to 60%, indicating the presence of RNA molecules that conferred a relative survival advantage (FIG. 15).

Figure 16:
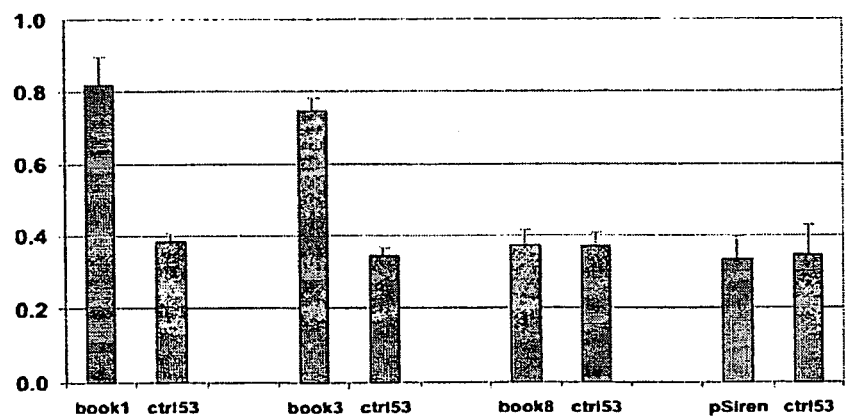
FIG. 16. Percent survival of FL5.12 cells (y-axis) infected with selected shRNA sequences ("books") after 15 hours of IL-3 withdrawal. Similar 2:1 survival ratios were seen after 2 days, though at lower levels. Ctrl53, random book; pSiren, vector.

10 shRNA-encoding sequences ("books") were retrieved by PCR, cloned back into pSiren, and sequenced. Of the 10, two were the same (books 1 and 7), indicating selective enrichment. FL5.12 cells were infected with 3 of the putative shRNA molecules separately (books 1, 3, and 8), each one assayed in 6 independent infections. The cells were subjected to 1 round of IL-3 withdrawal and recovery and subjected to a second withdrawal from IL-3. After 15 hours, cells were analyzed by flow cytometry, identifying infected cells by GFP fluorescence and dead cells by propidium iodide (PI) staining. Fractions of GFP-positive (infected), PI-negative (live) cells relative to the start of the experiment (just prior to the first IL-3 withdrawal) are depicted in FIG. 16. Books 1 and 3 conferred a statistically significant improvement in survival relative to cells infected with a random book (ctrl53) or with vector alone (pSiren) ($p<0.0001$ in each case by Student's t-test). The improved survival with books 1 and 3 correlated with a decrease in caspase 3 enzymatic activity. Because the cycling of IL-3 withdrawal included a recovery segment, books 1 and 3 were tested for effects on growth rate and none were seen. The stem sequences of books 1 and 3 are as follows:

```
                                        (SEQ ID No: 1)
Book 1:   5'-GGGTAGCTACATTTGCATATGTGGATATG-3'.
                                        (SEQ ID No: 2)
Book 3:   5'-GTGGATCAGTGTGTTATAGCTCGGGCAGG-3'
```

Thus, methods of the present invention are efficacious for identification of recombinant RNA molecules with therapeutic activity.

In other experiments, G1E, 293T, or FRDA cells are used to identify RNA molecules that protect against apoptosis, using methods analogous to the above method.

Example 8

Confirmation of Function of RNA Molecules of the Present Invention

In other experiments, following an RNAi library screening described in the above Example or one of the other Examples, the cell or cells in which the desired effect occurred are isolated, and the effective vector(s) are isolated and re-added to another population of cells. In another embodiment, positive-scoring RNAi sequences are retrieved by PCR (e.g, in the above method, by using primers overlapping the Mfe I and Blp I sites flanking the shRNA insertion site in the retroviral vector), and the same or another form of inhibitory RNA containing the same random sequence (in other embodiments, shRNA, microRNA, or siRNA) is administered to an additional population of cells. Recapitulation of the phenotype in the additional population of cells confirms the ability of the inhibitory RNA molecule to elicit the desired phenotype. In other experiments, the new form of RNAi is a reversible form of RNAi (in another embodiment, siRNA synthesized in vitro; in another embodiment, a form whose effects are reversed by removing it from the media), and the new form of RNAi is shown to confer the phenotype of interest in a reversible fashion. In other experiments, candidate positive shRNA are tested in model systems other than the one from which they were originally identified.

Example 9

Iterative Pooling and Re-Testing to Enrich for True Positives

In other experiments, 100% loss of viability is not observed in the control cultures of one of the above apoptosis assays. In this case, surviving cells in the library-infected culture are pooled, and the putatively effective shRNA sequences are retrieved by PCR, re-cloned into the parent vector, and re-tested as a sub-library by iterative pooling and re-testing. The iterative pooling and re-testing achieves sequential enrichment of true positives.

For example, a screening assay with a 1% false-positive rate (i.e. that achieves 99% loss of viability) is used to screen an RNAi library of the present invention; 1 in 100,000 of the sequences in the library is a true-positive (e.g. confers significant resistance to apoptosis). 200,000 cells are infected, yielding, on the average, two true positives and 2000 false positives. Surviving cells in the library-infected culture are pooled, and the putatively effective shRNA sequences are retrieved by PCR, re-cloned into the parent vector, and re-tested as a sub-library by iterative pooling and re-testing (e.g., in the above method, using primers that introduce Bgl II and Not I sites), yielding 200 true positives (2/2000×200,000) and 2000 false-positives. After a second round of pooling and re-testing, 20,000 true positives (200/2000×200,000) and 2000 false-positives are attained. Thus, after only two rounds of pooling and re-testing, the percentage of true positives (among all positives) can be increased from ~1% to more than 90%. For any of the above selection assays in which the numbers of surviving clones among library-infected cells and among control-infected cells are comparable, an increase in the numbers of surviving clones after re-introduction of pooled positives indicates the presence of true hits.

Thus, screening methods of the present invention can be used even in assays with a significant false-positive rate.

Example 10

Use of Additional Apoptosis Assays to Identify RNA Molecules with Ability to Inhibit Apoptosis In other experiments, the shRNA library is used in conjunction with the murine pro-B cell line, FL.5.12, to identify apoptosis-inhibiting RNA molecules. Conditions have been well established (IL-3 withdrawal) under which 100% of FL.5.12 cells die by apoptosis and >90% of cells are rescued (by Bcl-xL). In other embodiments, a variety of other cell types can be used by trivial modification of this technique.

In other experiments, staurosporine or another oxidant is used to induce apoptosis in 293T cells. In other experiments, a different IL-3-dependent cell line (e.g. 32D or Ba/F3) is used in place of FL5.12 cells. In other experiments, highly infectable sub-lines of 32D cells (obtainable from Dr. Warren Pear) are utilized. In other experiments, a VSV-G-expressing plasmid, pVSV-G, is used as an alternative to pHIT123. As an alternative to selection for survival selection by flow-sorting, for a surface marker or sortable reporter, is used. In other experiments, a cell line with tet-induced GFP is infected or transfected with the library in the presence of tet, and cells still positive for GFP after removal of tet are sorted and cloned. In other experiments, G1E cells (a murine proerythroblast line) are subjected to apoptosis by withdrawal of stem-cell factor (SCF).

In other experiments, RNAi selection is used in model systems that allow for selection of cells that survive a normally lethal condition. For example, in some genetic diseases, the disease-causing mutation causes cells to die in conditions that normal cells tolerate. By introducing a random shRNA library into the mutant cells, culturing the cells under the selective condition, and then selecting survivors, RNAi sequences that rescue the cells are identified.

Example 11

Definition of an In Vitro Model System for Selection of Friedreich Ataxia Cells with Enhanced Survival Capabilities Primary FRDA fibroblasts are far more sensitive to oxidative stress than normal control fibroblasts. (Jauslin et al. (Hum Molec Gen 11: 3055, 2002) used L-buthionine (S,R)-sulfoximine (BSO) to block the rate-limiting enzyme in glutathione synthesis, and found a concentration (0.05 mM) at which virtually all primary FRDA fibroblasts lose viability, but more than 90% of normal control fibroblasts retain viability.)

In other experiments, a time range of 16-48 h was used, and concentrations of 0.001, 0.05, and 0.1 mM BSO were tested. Glutathione depletion of these cells with BSO at 1 mM in media supplemented with 0.3 mg/ml fully saturated human transferrin, which exacerbates the tendencies of these cells to accumulate mitochondrial iron, rendered all the cells in a 6-well plate nonviable after 48 hours; while the majority of age- and passage-matched controls remained viable. By washing the cells, adding back their normal medium, and looking for colony formation, the minimum conditions under which 100% of the cells die were confirmed.

Example 12

Use of the shRNA Library to Identify RNA Molecules with Ability to Inhibit Death of FRDA Fibroblasts A random RNA library of the present invention is packaged as a retroviral vector. To produce high-titer retrovirus for the infection of human cells, 293T cells are co-transfected with the library of retroviral vectors, pHIT456 (amphotropic for human cells), and pCPG (gag-pol expressing plasmid), and culture supernatant is harvested after 36 hours. The library is added to primary FRDA fibroblasts, and fibroblast clones are selected for those that survive in the presence of oxidants at concentrations lethal to FRDA cells but non-lethal to normal control cells, in a similar manner to that described in the above Examples for 293T cells, which are also adherent. Effective sequences are retrieved by PCR and confirmed by re-contacting primary FRDA fibroblasts with positive vectors, as described in Examples 7-9.

Example 13

Use of the shRNA Library to Identify RNA Molecules with Ability to Induce Long-Term Proliferation of Stem Cells The cell-surface marker CD34 is known to be lost from hematopoietic stem cells, as the cells differentiate. In other experiments, these cells are infected or transfected with a random shRNA library, cultured, and then sorted for cells that retain CD34, even after cells in a control culture lose CD34 expression completely, thus enabling determination of RNAi sequences that allow the culturing of hematopoietic stem cells without differentiation. In other experiments, for confirmatory testing, another, reversible form of inhibitory RNA (e.g. siRNA synthesized in vitro) that contains the identified RNAi sequences is generated, as described in Example 8. The new form of RNAi is added to hematopoietic stem cells and shown to maintain CD34 expression in a reversible fashion Example 14

Use of the shRNA Library to Identify RNA Molecules with Ability to Sustain Pluripotency of Stem Cells In other experiments, random RNA libraries of the present invention are used to identify RNA sequences that can sustain pluripotency of stem cells. A stem cell line (e.g. LRK1 cells) is infected or transfected with a random shRNA library and incubated under conditions under which it differentiates (in the case of LRK1 cells, in the absence of IL-6), and formation of stem cell colonies is detected. The vector carried by stem cell colonies is obtained and sequenced to identify RNA sequences that can sustain pluripotency of stem cells. In other experiments, for confirmatory testing, another, reversible form of inhibitory RNA that contains the identified RNAi sequences is generated, as described in Example 8. The new form of RNAi is added to LRK1 cells and shown to maintain self-renewal and/or an undifferentiated state in a reversible fashion.

In other experiments, LRK1 cells are used to identify pluripotency-sustaining sequences using the method described by Chambers et al (Functional expression cloning of Nanog, a pluripotency sustaining factor in embryonic stem (ES) cells. Cell 113, 643-55 (2003)). LRK1 cells are transfected/infected with an RNAi library of the present invention, and self-renewing cells in the absence of cytokines are selected and pooled. shRNA sequences are then retrieved by PCR and re-ligated into the parent vector and the vectors are re-introduced into LRK1 cells one or more times, as necessary to enrich sufficiently for true positives before preparing plasmids from single, undifferentiated colonies. In other experiments, clones containing active sequences are confirmed by the formation of stem-cell colonies (which are identifiable by morphology and alkaline phosphatase staining) in the absence of cytokines.

Example 15

Use of the shRNA Library to Identify RNA Molecules with Ability to Induce Differentiation of Precursor Cells into Cell Types of Interest In other experiments, random RNA libraries of the present invention are used to identify RNA sequences that can induce differentiation of precursor cells into cell types of interest. For example, differentiation of promyeloid HL60 cells (e.g. into neutrophils), differentiation of the leukemic cell line U937 cells (e.g. into monocytes), or the differentiation of the erythroid cell line G1E is determined (e.g. into erythroid cells). Differentiation can be detected by expression of marker proteins (e.g. Ter-119 or CD11b) or by morphological criteria (e.g. adherence to plastic).

In another experiment, cells are incubated in non-differentiation media, and flow cytometry is performed for GFP and CD11b (HL60 and U937 cells) or GFP and Ter-119 (G1E cells). Cells that express both GFP (to confirm the presence of a vector) and the appropriate differentiation marker at levels higher than the highest evident in the control cells are "gated on" (selected). Differentiation of flow-sorted HL60 and U937 cells can be further confirmed by adherence of the cells to plastic. Other markers of differentiation include CD14 expression and cell morphology by Wright-Giemsa staining. G1E cells form small, hemoglobinized colonies, become benzidine- and band-3-positive, and shift to a pro-normoblast morphology.

In other experiments, random RNA libraries are used to identify RNA sequences that can induce differentiation of embryonic stem (ES) cells (in other embodiment, human ES cells or murine ES cells). In other embodiments, the transfected ES cells are introduced into mice, the mice are sacrificed several weeks later, and GFP-positive cells are isolated from various tissues, then sequences associated with the cells are retrieved. The sequences play a role in differentiation of the cells into the particular cell type.

In other embodiments, differentiation of ES cells into vascular endothelial, striated muscle, myocardial, skeletal, early embryonic mesoderm, endoderm-derived, primitive endoderm (e.g. hypoblast), yolk sac visceral endoderm, ectoderm derived, neuron-like cell types, or other known cell types is detected. In other experiments, cell sorting is used to select cells that have differentiated to or toward the desired cell type. Precursor cells are infected or transfected with a random shRNA library, and fully or partially differentiated cells are isolated. The vector carried by differentiated cells is obtained and sequenced to identify RNA sequences that can induce differentiation of precursor cells into cell types of interest. In other experiments, for confirmatory testing, another, reversible form of inhibitory RNA that contains the identified RNAi sequences is generated, as described in Example 8. The new form of RNAi is added to precursor cells and shown to induce differentiation.

Example 16

Use of the shRNA Library to Identify RNA Molecules with Ability to Prevent Viral Replication or Protect Cells Against Viral Infection or Cytopathicity In other experiments, random RNA libraries of the present invention are used to identify RNA sequences that can prevent viral replication or protect cells against viral infection or cytopathicity. Primary cells or cell lines are infected or transfected with an RNAi library of the present invention then infected with a cytopathic virus (in other embodiments, human lymphocytes and HIV-1 virus, or duck embryo fibroblast (DEF) cells and AHV-1 are utilized), then survivors are identified. In other experiments, for confirmatory testing, another, reversible form of inhibitory RNA that contains the identified RNAi sequences is generated, as described in Example 8. The new form of RNAi is added to the cells and shown to prevent viral replication or protect the cells against viral infection or cytopathicity in a reversible fashion.

Example 17

Further Improvement of RNA Molecules of the Present Invention

To identify improvements of sequences identified after RNAi library screening described in one of the above Examples, random mutagenesis is used. In other experiments, an error-prone copying method is utilized. In another embodiment, error-prone PCR is utilized. Random mutagenesis by error-prone PCR takes advantage of the low fidelity of Taq polymerase in the presence of $Mn^{2+}$, high $Mg^{2+}$, and unequal dNTP concentrations, and is well known in the art. Because a randomly mutagenized RNAi sequence requires, under some conditions, a matched reverse complement for shRNA, iterative selection requires a recapitulation of the library synthesis protocol described in above Examples. The cell or cells in which the desired effect occurred are isolated, and using error-prone PCR, the sequence corresponding to that of the oligonucleotide at the top of FIG. 3 or FIG. 6 is amplified, e.g. by using perfectly matched primers that extend from the edge of the N28 sequence, plus one nucleotide on the downstream side (so that the 29th nucleotide in the final shRNA stem is mutagenized as well), all the way to the ends of the oligonucleotide sequence, this creates a library of "half-books."

After random mutagenesis, library construction is performed as described in one of the above Examples. The first, mismatched extension primer is, in another embodiment, an equimolar mix of four primers, each ending in a different nucleotide (complementary to the random nucleotide just downstream of the N28), (without the need for mixing four sub-libraries as done in the initial library generation), each with a different "29th" nucleotide. Although the strand of DNA complementary to the equivalent of the oligonucleotide at the top of FIG. 4 is present in the single-extension reaction, only single-extension products of the recessed, first extension primer anneal to the hairpin-loop linker.

The sub-library for a given sequence is introduced into target cells as described in one of the above Examples, except that the original sequence is included among the controls. In some experiments, increased effectiveness of an shRNA construct in this context is defined as (1) a larger number of surviving cells under the original conditions used for selection, (2) longer survival under the original conditions used for selection, or (3) survival under more stringent conditions. For initially identified RNA molecules that show subtle improvement over the control shRNAs (such as survival for slightly longer under the original conditions used for selection), the second criterion will likely be the most important for selecting more effective sequences. For RNA molecules that rescue cells for extended periods in the initial confirmatory assay, the third criterion will be the most important for selecting more effective sequences; for such sequences, more stringent conditions are tested to establish new minimum conditions for 100% loss of viability.

In other experiments, the entire gene encoding the RNAi molecule of the present invention (i.e. both halves of the double-stranded region, and the intervening region; or "whole books") is copied by a low-fidelity method, then the sub-library of whole-books is inserted or subcloned into an expression vector, etc, and the resulting sub-library is introduced into target cells as described for the above method.

In other experiments, for HL60, U937, and G1E cells, increased effectiveness of an shRNA construct is defined as higher expression of differentiation markers, a larger number of cells expressing differentiation markers, or expression of a wider range of differentiation markers. For LRK1 cells, increased effectiveness of an shRNA construct is defined as a larger number of undifferentiated colonies, or maintenance of undifferentiated cells over more passages.

In other experiments, cells infected or transfected with vectors encoding the RNA molecules are followed and compared closely by microscopic examination to cells infected or transfected with the sub-library for that sequence. In another embodiment, sequences identified are retrieved by PCR. In another embodiment, the correctness and activity of the sequences is confirmed by re-introduction into cells, as described in Example 8.

In another embodiment, in cases wherein a secondary sequence significantly improves upon a primary sequence, another round of iterative selection is performed on the secondary sequence. In another embodiment, improved sequences are tested in other ways, for example with a tetrazolium dye reduction assay. Although the selection assay described herein for FRDA cells is based on oxidant stress, this assay can also be used to obtain RNA molecules that improve aspects of FRDA cells unrelated to anti-oxidant defenses per se. The reason for this is that the selection assay is performed under oxidant stress conditions that allow survival of normal, control fibroblasts; therefore, an intervention that makes FRDA cells more like normal cells will, in another embodiment, improve survival in the assay. Some shRNA are found to affect the tri-nucleotide repeat expansion that inhibits frataxin expression, or the triplex DNA that is formed by the tri-nucleotide repeat expansion, which is measured by an increase in frataxin expression, either using Northern or Western blots. In another embodiment, the above process identifies improved sequences.

Example 18

Use of RNA Molecules of the Present Invention to Identify Drug Targets for Disease States and Stem Cell Applications In another embodiment, improved sequences implicate individual genes, which in turn suggest potential drug targets. Candidate genes are identified by homology searching the human genome database (with the first 22 nt of improved sequences in particular). Candidate genes are confirmed by using independent shRNAs targeting different mRNA sequences from the same gene. Additional confirmation is performed by Western analysis, Northern analysis, and/or quantitative RT-PCR, in comparison with control shRNAs to rule out non-specific effects. Optional, final confirmation involves reversing the phenotype (rescue from oxidant stress, for example) by re-expressing the target gene with mutations that abrogate the shRNA effect but do not change the encoded amino acids.

In other experiments, improved sequences implicate multiple target genes, which are confirmed by microarray analyses.

In other experiments, follow-up experiments are performed to determine the mechanism of action of the RNAi molecule, thereby identifying drug targets, e.g. in the case of FRDA cells, increasing mitochondrial iron export or decreasing mitochondrial iron import; stabilizing iron-sulfur clusters or otherwise increasing frataxin stability or function; enhancing antioxidant defenses; partially bypassing the need for mitochondrial function through a metabolic effect; or affecting the triplex DNA formed by the tri-nucleotide repeat expansion in the first intron of the FRDA gene, thereby increasing frataxin expression.

Example 19

Use of a Computer-Generated shRNA Library to Identify Therapeutic RNA Sequences

A computer and oligonucleotide synthesizer are used to generate an shRNA library containing 65,500 random shRNA molecules, as follows:

A set of 65,500 sequences is generated, having appropriate flanking sequences for subcloning and an internal portion comprising a gene encoding an RNA molecule with the following components: (a) residues 1-22 are randomly generated; (b) the next 3-20 residues are constant and non-palindromic; (c) the next 22 residues are complementary to the first 22 residues. Alternatively, the encoded RNA molecule has the following components (a) residues 1-8, which are random; (b) residues 9-22 are constant; (c) the next 5-20 residues are constant and non-palindromic; (d) the next 22 residues are complementary to the first 22 residues. Alternatively, residues 1 and 9-22 of the ds region are held constant, while the others are randomized. Alternatively, any other portion of the ds region is held constant, while the remaining portion is randomized. In some experiments, loop sequences from known and/or naturally occurring RNAi molecules are utilized; however, it will be understood to those skilled in the art that a variety of loop sequences, including previously unrecognized ones, are suitable for this method. In addition, it will be understood to those skilled in the art that the ds region of the RNA molecule need not be 22 nucleotides, but could be any length from 6-30 nucleotides, inclusive. In other experiments, wherein a ds region of 29 nucleotides is utilized, the entire 29 nucleotides region is mutagenized.

An oligonucleotide synthesizer is programmed with the computer-generated sequences. Each of the 65,500 shRNA-encoding sequences is annealed with its complement and then ligated as a pool into an appropriate expression vector, thus creating a library of 65,500 random shRNA-encoding sequences that represent a random sampling of the 18 trillion possible 22-mer shRNA-encoding sequences.

In other experiments, this library is tested a cell model of a disease or phenotype of interest, as described for Examples 7-16. Effective sequences are retrieved by PCR and confirmed by re-contacting cells with positive vectors, as described in Examples 7-13.

Example 20

Further Improvement of RNA Molecules

To identify improvements of sequences identified after RNAi library screening described in the above Example, the sequences are mutagenized. In other experiments, an error-prone copying method is utilized. In another embodiment, error-prone PCR is utilized. Random mutagenesis by error-prone PCR takes advantage of the low fidelity of Taq polymerase in the presence of $Mn^{2+}$, high $Mg^{2+}$, and unequal dNTP concentrations, and is well known in the art. Because a randomly mutagenized RNAi sequence requires, under some conditions, a matched reverse complement for shRNA, iterative selection requires a recapitulation of the library synthesis protocol described in above Examples. The cell or cells in which the desired effect occurred are isolated, and using error-prone PCR, the sequence corresponding to that of the oligonucleotide at the top of FIG. 3 or FIG. 6 is amplified, e.g. by using perfectly matched primers that extend from the edge of the N28 sequence, plus one nucleotide on the downstream side (so that the 29th nucleotide in the final shRNA stem is mutagenized as well), all the way to the ends of the oligonucleotide sequence, this creates a library of "half-books."

After random mutagenesis, library construction is performed as described in one of the above Examples. The first, mismatched extension primer is, in another embodiment, an equimolar mix of four primers, each ending in a different nucleotide (complementary to the random nucleotide just downstream of the N28), (without the need for mixing four sub-libraries as done in the initial library generation), each with a different "29th" nucleotide. Although the strand of DNA complementary to the equivalent of the oligonucleotide at the top of FIG. 4 is present in the single-extension reaction, only single-extension products of the recessed, first extension primer anneal to the hairpin-loop linker.

In other experiments, variants of the sequence identified in the above Example are generated using a computer and oligonucleotide synthesizer as follows:

A set of sequences is generated, having appropriate flanking sequences for subcloning and an internal portion comprising a gene encoding an RNA molecule with the following components: (a) a portion of residues 1-22 are kept constant, based on the RNA sequence identified in the above Example, while the remainder are randomized; (b) the next 3-20 residues are constant and non-palindromic; (c) the next 22 residues are complementary to the first 22 residues. In other experiments, the seed sequence (approximately residues 1-8 of the ds region) is kept constant, while the remainder of the ds region is varied. In other experiments, the seed sequence is varied, while the remainder of the ds region is kept constant. In other experiments, residues 2-8 of the seed sequence are kept constant, while residues An oligonucleotide synthesizer is programmed with the computer-generated sequences. Each of the 65,500 shRNA-encoding sequences is annealed with its complement and then ligated as a pool into an appropriate expression vector, thus creating a library of 65,500 random shRNA-encoding sequences that represent a random sampling of the 18 trillion possible 22-mer shRNA-encoding sequences.

After randomization of the shRNA by either mutagenesis or computer randomization, the sub-library for a given sequence is introduced into target cells as described in one of the above Examples, except that the original sequence is included among the controls. In some experiments, increased effectiveness of an shRNA construct in this context is defined as (1) a larger number of surviving cells under the original conditions used for selection, (2) longer survival under the original conditions used for selection, or (3) survival under more stringent conditions. For initially identified RNA molecules that show subtle improvement over the control shRNAs (such as survival for slightly longer under the original conditions used for selection), the second criterion will likely be the most important for selecting more effective sequences. For RNA molecules that rescue cells for extended periods in the initial confirmatory assay, the third criterion will be the most important for selecting more effective sequences; for such sequences, more stringent conditions are tested to establish new minimum conditions for 100% loss of viability.

In other experiments, the sub-library is tested using one of the protocols described for Example 17, in order to identify improved sequences.

What is claimed is:

1. A set or library of recombinant expression vectors, wherein said set or library of recombinant expression vectors expresses a set or library of short hairpin ribonucleic acid (shRNA) molecules, each shRNA molecule comprises contiguously:

(a) a variable region 17-30 nucleotides long, consisting of a sequence, wherein said sequence is either (i) substantially random; or (ii) comprises a first sub-region and a second sub-region, wherein said first sub-region is substantially random and said second sub-region has a first sequence common to said set or library of shRNA molecules;

(b) a non self-complementary region 3-20 nucleotides long, consisting of a second sequence common to said library; and (c) a complementary region consisting of a sequence, wherein said sequence is the reverse complement of the variable region;

wherein the substantially random sequence in the variable region has minimal sequence bias, wherein the variable and complementary regions form a double-stranded region and the non self-complementary region forms a loop that connects the two strands of the double-stranded region.

2. The set or library of recombinant expression vectors of claim 1, wherein individual recombinant expression vectors each further comprises a promoter of an RNA polymerase.

3. The set or library of recombinant expression vectors of claim 1, wherein individual recombinant expression vectors each further comprises a gene encoding an RNA inhibitory (RNAi) molecule of known function.

4. The set or library of recombinant expression vectors of claim 1, wherein said variable region is 8-30 nucleotides long.

5. The set or library of recombinant expression vectors of claim 1, wherein said first sub-region is 8-29 nucleotides long.

6. A method for identifying an RNA molecule that is capable of affecting a biological parameter of interest, comprising the steps of:
   a. contacting a cell population with the set or library of recombinant expression vectors of claim 1, wherein said set or library of said expression vectors, or a fraction thereof, is taken up by individual cells of said cell population; and
   b. determining or measuring said biological parameter of interest or a readout thereof in said cell population;
   whereby, if a particular cell in said cell population exhibits an alteration of said biological parameter of interest or readout thereof, then said particular cell carries a particular recombinant expression vector that encodes a particular RNA molecule that is capable of affecting said biological parameter of interest.

7. The method of claim 6, wherein said biological parameter of interest or readout thereof is an expression of a protein of interest.

8. The method of claim 6, wherein said biological parameter of interest or readout thereof is an ability of a cell to survive or maintain growth under adverse conditions.

9. The method of claim 6, wherein said biological parameter of interest or readout thereof is a susceptibility of a cell to an intracellular pathogen or an ability of an intracellular pathogen to replicate in a cell.

10. The method of claim 9, wherein said intracellular pathogen is a virus.

11. The method of claim 6, wherein said biological parameter of interest or readout thereof is a differentiation of a cell into a cell type of interest.

12. The method of claim 6, wherein said biological parameter of interest or readout thereof is an ability to induce long-term proliferation or sustain pluripotency of a cell.

13. The method of claim 6, further comprising the step of isolating or amplifying said particular expression vector, its insert, or a fragment thereof, and sequencing either:
   a. said particular expression vector; or
   b. a fragment of said particular expression vector, wherein said fragment comprises the coding sequence for said particular RNA molecule.

14. The method of claim 6, further comprising the steps of contacting an additional cell with said particular expression vector and determining or measuring said biological parameter of interest or readout thereof in said additional cell.

15. The method of claim 6, further comprising the steps of generating a copy of said particular RNA molecule, contacting an additional cell with said copy of said particular RNA molecule, and determining or measuring said biological parameter of interest or readout thereof in said additional cell.

16. The method of claim 6, further comprising the steps of
   a. inserting into a second expression vector backbone a sequence that encodes either: (a) said particular RNA molecule or (b) a fragment of said particular RNA molecule, thereby generating a second recombinant expression vector, wherein said second recombinant expression vector encodes either:
      i. said particular RNA molecule; or
      ii. an altered version of said particular RNA molecule, wherein said altered version of said particular RNA molecule comprises a region that shares homology with a double-stranded region of said particular RNA molecule;
   b. contacting an additional cell with said second expression vector; and
   c. determining or measuring said biological parameter of interest or readout thereof in said additional cell.

17. The method of claim 6, further comprising the steps of
   a. inserting into a second expression vector backbone a sequence that encodes said particular RNA molecule; or that encodes a fragment of said particular RNA molecule, thereby generating a second expression vector, wherein said second expression vector encodes an altered version of said particular RNA molecule, wherein said altered version of said particular RNA molecule comprises a region that shares homology with a double-stranded region of said particular RNA molecule;
   b. producing a copy of said altered version of said particular RNA molecule;
   c. contacting an additional cell with said copy of said altered version of said particular RNA molecule; and
   d. determining or measuring said biological parameter of interest or readout thereof in said additional cell.

18. The method of claim 6, further comprising the steps of:
   a. isolating or amplifying either: (i) said particular expression vector; (ii) the insert of said particular expression vector; or (iii) a fragment of said particular expression vector, wherein said fragment comprises a region encoding the particular RNA molecule;
   b. mutagenizing a fragment of said particular expression vector, thereby generating a sub-library of nucleotide molecules, said sub-library of nucleotide molecules comprising variants of said fragment of said particular expression vector;
   c. generating a sub-library of recombinant expression vectors containing said sub-library of nucleotide molecules;
   d. contacting a second population of cells with said sub-library of recombinant expression vectors, wherein said sub-library of recombinant expression vectors, or a fraction thereof, is taken up by individual cells of said second population of cells; and
   e. determining or measuring said biological parameter of interest or a readout thereof in said second population of cells,
   whereby, if said biological parameter of interest or readout thereof is further altered in a particular cell in said second set of cells, then said particular cell carries an improved expression vector, wherein said improved expression vector encodes an improved RNA molecule that affects said biological parameter of interest or readout thereof more than the particular RNA molecule of claim 6.

19. The method of claim 18, wherein the step of mutagenizing comprises copying a fragment of said particular expression vector by a low-fidelity method.

20. The method of claim 19, wherein said low-fidelity method is an error-prone polymerase chain reaction (PCR).

21. The method of claim 18, further comprising the step of isolating or amplifying said improved expression vector or a fragment thereof, wherein said fragment comprises the coding sequence for said improved RNA molecule, and sequencing either (a) said improved expression vector or (b) said fragment thereof.

22. The method of claim 18, further comprising the step of contacting an additional cell with said improved expression vector and determining or measuring said biological parameter of interest or readout thereof in said additional cell.

23. A method of identifying a drug target for a disease or disorder of interest, comprising the steps of
   a. identifying an RNA molecule that affects a biological parameter of interest by the method of claim 6, wherein said biological parameter of interest is altered in said disease or disorder of interest; and
   b. identifying a cellular RNA molecule whose expression is altered by said RNA molecule,
   whereby said cellular RNA molecule is identified as a drug target for said disease or disorder of interest.

24. The set or library of recombinant expression vectors of claim 1 generated by a method, said method comprising the steps of:
   a. obtaining a nucleic acid intermediate II from a single-stranded nucleic acid intermediate I, wherein said single-stranded nucleic acid intermediate I consists of:
      (i) a first constant region;
      (ii) said variable region; and
      (iii) a second constant region;
         wherein the step of obtaining said nucleic acid intermediate II comprises the steps of (a) annealing a primer to the second constant region of the single-stranded nucleic acid intermediate I, said primer comprising one or more mismatched residues with respect to the second constant region and (b) extending said primer to obtain a double-stranded intermediate I B, and (c) obtaining the nucleic acid intermediate II from the double-stranded intermediate I B by ligating a linker nucleic acid molecule to the 3' end of the single-stranded nucleic acid intermediate I and the 5' end of the additional single-stranded nucleic acid molecule;
      and wherein said nucleic acid intermediate II comprises:
         (i) said single-stranded nucleic acid intermediate I;
         (ii) an intervening region; and
         (iii) a region that hybridizes with said single-stranded nucleic acid intermediate I;
   b. obtaining a double-stranded intermediate III from nucleic acid intermediate II, comprising said nucleic acid intermediate II and an additional nucleic acid molecule that hybridizes with said nucleic acid intermediate II, and wherein said double-stranded intermediate III comprises:
      (i) a first, double-stranded copy of said first constant region or a fragment thereof;
      (ii) a first, double-stranded copy of said variable region;
      (iii) a first, double-stranded copy of said second constant region;
      (iv) a double-stranded copy of said intervening region;
      (v) a second, inverted double-stranded copy of said second constant region;
      (vi) a second, inverted double-stranded copy of said variable region; and
      (vii) a second, inverted double-stranded copy of said first constant region or a fragment thereof;
      wherein said first, double-stranded copy of said second constant region and said second, inverted double-stranded copy of said second constant region have a restriction enzyme site asymmetry created by said mismatched primer used to obtain the double stranded intermediate II, such that:
         (i) said first, double-stranded copy of said second constant region, but not said second, inverted double-stranded copy of said second constant region, is a substrate for a first restriction enzyme, and;
         (ii) said second, inverted, double-stranded copy of said second constant region, but not said first double-stranded copy of said second constant region, is a substrate for a second restriction enzyme;
      said method further comprising the step of obtaining a circular intermediate IV from said double-stranded intermediate III, said circular intermediate IV comprising an expression vector backbone and, as an insert, either:
         (a) said double-stranded intermediate III; or
         (b) a fragment of said double-stranded intermediate III, wherein said fragment comprises said first, double-stranded copy of said variable region and said second, inverted double-stranded copy of said variable region;
   thereby generating a set or library of recombinant expression vectors, wherein said set or library of recombinant expression vectors is capable of expressing said set or library of shRNA molecules.

25. The set or library of recombinant expression vectors of claim 24, wherein said set or library of recombinant expression vectors is a set or library of recombinant viruses.

26. The set or library of recombinant expression vectors of claim 1, wherein the non self-complementary region has a sequence selected from (i) CCTCCCGC, (ii) CCCC, (iii) AGGC, (iv) CCTCAC, (v) CCTCAC, (vi) TCTTCCGC, (vii) GTTTAG, and (viii) CTAAAC.

27. The set or library of recombinant expression vectors of claim 26, wherein the sequence of the non self-complementary region is GTTTAG or CTAAAC.

\* \* \* \* \*